United States Patent
Williams et al.

(10) Patent No.: US 10,279,094 B2
(45) Date of Patent: May 7, 2019

(54) ENDOVASCULAR VARIABLE AORTIC CONTROL CATHETER

(71) Applicant: The United States of America, as represented by the Secretary of the Air Force, Washington, DC (US)

(72) Inventors: Timothy K. Williams, Davis, CA (US); Lucas Paul Neff, Davis, CA (US); James B. Sampson, Davis, CA (US)

(73) Assignee: United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 14/990,465

(22) Filed: Jan. 7, 2016

(65) Prior Publication Data
US 2016/0206798 A1 Jul. 21, 2016

Related U.S. Application Data

(60) Provisional application No. 62/105,887, filed on Jan. 21, 2015, provisional application No. 62/235,087, filed on Sep. 30, 2015.

(51) Int. Cl.
*A61M 1/12* (2006.01)
*A61M 1/10* (2006.01)

(52) U.S. Cl.
CPC .......... *A61M 1/125* (2014.02); *A61M 1/1018* (2014.02); *A61M 1/1037* (2013.01);
(Continued)

(58) Field of Classification Search
CPC .. A61M 1/125; A61M 1/1018; A61M 1/1037; A61M 1/1086; A61M 1/1008; A61M 1/12; A61M 2205/3334
(Continued)

(56) References Cited

U.S. PATENT DOCUMENTS

| 4,456,011 A | 6/1984 | Warnecke |
| 5,320,604 A | 6/1994 | Walker et al. |

(Continued)

OTHER PUBLICATIONS

Brenner, M.L., et al. "A clinical series of resuscitative endovascular balloon occlusion of the aorta for hemorrhage control and resuscitation," J. Trauma Acute Care Surg., vol. 75, No. 3, 506-511, 2013 (6 pages).
(Continued)

*Primary Examiner* — Carl H Layno
*Assistant Examiner* — Erin M Piateski
(74) *Attorney, Agent, or Firm* — AFMCLO/JAZ; Chastity Whitaker

(57) ABSTRACT

Endovascular variable aortic control catheters (EVACC) are provided that are adapted to augment upstream blood pressure and regulate downstream blood flow for patients in shock. The EVACC devices provide improved treatment for truncal wounds, which may be used for example on a battlefield, thereby increasing survivability of injured soldiers. The devices are a catheter-based system having a proximal hand piece for controlled deployment of the device through a delivery sheath. A collapsible, wire framework supports an expandable and collapsible occlusion barrier. The wire basket and occlusion barrier expand to fit within the lumen of the aorta. Various movable elements are used to adjust an adjustable passageway to regulate controlled anterograde blood flow.

8 Claims, 47 Drawing Sheets

(52) U.S. Cl.
CPC ......... *A61M 1/1086* (2013.01); *A61M 1/1008* (2014.02); *A61M 1/12* (2013.01); *A61M 2205/3334* (2013.01)

(58) Field of Classification Search
USPC .......................................................... 600/17
See application file for complete search history.

(56) References Cited

U.S. PATENT DOCUMENTS

| | | | |
|---|---|---|---|
| 6,135,981 | A | 10/2000 | Dyke |
| 6,743,196 | B2 | 6/2004 | Barbut et al. |
| 6,743,208 | B1 | 6/2004 | Coyle |
| 7,198,632 | B2 | 4/2007 | Lim et al. |
| 7,220,269 | B1 | 5/2007 | Ansel |
| 7,771,448 | B2 | 8/2010 | Ravikumar |
| 7,927,346 | B2 | 4/2011 | VanCamp et al. |
| 8,257,421 | B2 | 9/2012 | Berez et al. |
| 2002/0188344 | A1 | 12/2002 | Bolea et al. |
| 2003/0083617 | A1 | 5/2003 | Germain et al. |
| 2003/0195382 | A1* | 10/2003 | Barbut .................. A61B 5/0215 600/16 |
| 2003/0212361 | A1 | 11/2003 | Boyle et al. |
| 2004/0010282 | A1 | 1/2004 | Kusleika |
| 2004/0172055 | A1 | 9/2004 | Huter et al. |
| 2006/0282115 | A1 | 12/2006 | Abrams et al. |
| 2009/0082800 | A1 | 3/2009 | Janardhan |
| 2012/0078343 | A1 | 3/2012 | Fish |
| 2013/0102926 | A1 | 4/2013 | Eliason et al. |
| 2014/0243873 | A1 | 8/2014 | Franklin |
| 2014/0350523 | A1* | 11/2014 | Dehdashtian .... A61B 17/12109 604/509 |
| 2015/0104331 | A1* | 4/2015 | Dye ....................... A61M 1/101 417/53 |

OTHER PUBLICATIONS

Scott, D.J., et al. "A novel fluoroscopy-free, resuscitative endovascular aortic balloon occlusion system in a model of hemorrhagic shock," J. Trauma Acute Care Surg., vol. 75, No. 1, 122-128, 2013 (7 pages).
White, J.M., et al., "Endovascular balloon occlusion of the aorta is superior to resuscitative thoracotomy with aortic clamping in a porcine model of hemorrhagic shock," Surgery, vol. 150, No. 3, 400-409, 2011 (10 pages).
Saito, N., et al. "Evaluation of the safety and feasibility of resuscitative endovascular balloon occlusion of the aorta," J. Trauma Acute Care Surg., vol. 78, No. 1, 122-128, 2015 (8 pages).
Markov, N.P., et al. "Physiologic tolerance of descending thoracic aortic balloon occlusion in a swine model of hemorrhagic shock," Surgery, vol. 153, No. 6, 848-856, 2013 (9 pages).
Stannard, A., et al. "Resuscitative Endovascular Balloon Occlusion of the Aorta (REBOA) as an Adjunct for Hemorrhagic Shock," J. Trauma, Injury, Infection, and Critical Care, vol. 71, No. 6, 1869-1872, 2011 (4 pages).
PCT/US16/14080 International Search Report and Written Opinion (4 pages).
U.S. Search Authority, International Search Report and Written Opinion in PCT/US16/14080, dated Mar. 11, 2016, 2 pages total.

* cited by examiner

ENDOVASCULAR VARIABLE AORTIC CONTROL CATHETER

CROSS-REFERENCE TO RELATED APPLICATIONS

The present application claims priority to U.S. Provisional Patent Application Ser. No. 62/105,887 filed Jan. 21, 2015, and 62/235,087 filed Sep. 30, 2015, each of which is hereby incorporated herein by reference in its entirety.

RIGHTS OF THE GOVERNMENT

The invention described herein may be manufactured and used by or for the Government of the United States for all governmental purposes without the payment of any royalty.

FIELD OF THE INVENTION

This disclosure relates generally to endovascular aortic occlusion devices deployed within the aorta. More particularly, the invention relates to endovascular aortic occlusion devices adapted for augmenting blood pressure and controlling blood flow downstream of the occluded region.

BACKGROUND

Death from the complications of truncal hemorrhage continues to exist as a high probability in an overwhelming number of cases in both the military and civilian medical spheres. Existing systems and procedures used to control truncal hemorrhage frequently contribute to a patient's ultimate death through inability to maintain adequate blood flow to vital organs. It is well recognized that without controlled distal reperfusion, hemodynamic collapse is common, particularly where open aortic cross-clamping is used to stop hemorrhage. The ability to rapidly deliver effective, variable, and adaptive control of aortic flow for hemorrhaging patients will save innumerable lives.

Mitigation of battlefield injury and hemorrhage is a high priority of U.S. military trauma surgeons and researchers. Uncontrolled blood loss is recognized as the leading cause of death in 90 percent of the potentially survivable battlefield cases and in 80 percent of those who died in a military treatment facility. "Bleed-outs," especially those caused by groin or neck wounds, challenge medics, corpsmen and physicians who can do little to stop blood loss caused by major arterial injuries.

Two devices, the Combat Ready Clamp and Abdominal Aortic Tourniquet, have been built to treat truncal injuries. The Combat Ready Clamp is primarily for treating junctional hemorrhage (i.e. between the trunk and an extremity). The Combat Ready Clamp is ineffective against wounds involving the genital region or the loss of both legs. The Abdominal Aortic Tourniquet functions as a large blood pressure cuff which wraps around the lower torso to minimize extremity bleeding.

Limiting or stopping blood flow through the major blood vessel of the body, the aorta, is an established method for slowing the rate of blood loss in a severely injured patient with ongoing bleeding. In the military, this aortic occlusion has traditionally been achieved using a large aortic clamp inserted into the chest cavity via a large incision between the ribs. This dramatic and extremely invasive maneuver is typically a "last ditch" effort. The clamping of the aorta excludes the systemic circulation, by definition, thus causing an ischemia. The goal of the aortic clamping procedure is to keep the patient's remaining blood circulating to the heart, lungs, and brain for precious minutes until bleeding below the aortic clamp is controlled and the patient can be resuscitated and systemic circulation restored. Because of the inherent morbidity of the aortic clamp maneuver, it is often reserved for only the sickest or moribund patients who have lost vital signs and are essentially already dead.

Recently, balloon catheters used in endovascular surgery have been repurposed to fully occlude the aorta by inflation of a balloon in the lumen of the aorta, as an alternative to aortic clamping. This procedure is referred to as Resuscitative Endovascular Balloon Occlusion of the Aorta (REBOA). REBOA has the potential to achieve effective aortic occlusion with less morbidity. Therefore, REBOA may be used earlier in the clinical course of the bleeding patient.

As with aortic clamping, REBOA can be used to increase blood pressure to vital organs while slowing ongoing blood loss. However, currently available FDA-approved balloon catheters used for REBOA can only reliably achieve complete occlusion or no occlusion. As such, attempting to wean a patient from complete balloon occlusion by slowly deflating the balloon is not achievable. When aortic occlusion is used in the course of treatment of a hemorrhaging patient, the physician must begin to wean the patient off complete occlusion as early as possible. Using REBOA, when the balloon is inflated, everything below the balloon quickly starts to die due to lack of blood flow. When the balloon is deflated to initiate flow, hemodynamic collapse is a possibility. Additionally, variation in patient size (height, weight, aortic diameter) limits the ability of a single REBOA catheter to effectively occlude aortic flow in all patients.

Currently, REBOA is performed utilizing devices largely intended for other purposes, specifically the FDA-approved CODA® balloon catheter (Cook Medical Technologies, LLC, Bloomington, Ind.) for occluding large blood vessels and molding of aortic endoprostheses. While effective at complete aortic occlusion, the CODA® balloon catheter is not ideally suited for partial vessel occlusion or controlled distal reperfusion during gradual deflation based on its inherent design characteristics, particularly an inability to create a variable and sustained pressure gradient across the balloon. An example of this type of device is disclosed by Eliason et al., U.S. Patent Application Publication No. 2013/0102926, published Apr. 25, 2013, which is incorporated by reference herein in its entirety. The invention of Eliason et al. is directed to a method for placing an aortic occlusion device without having to rely on fluoroscopy to ensure proper placement. The system of Eliason et al. relies on the use of an inflatable balloon to provide occlusion, and thus, has only marginal ability to control variability in flow from upstream to downstream of the occlusion device. Moreover, the system of Eliason et al. is unable to provide controlled anterograde blood flow (i.e., distal reperfusion).

It is well recognized that without controlled distal reperfusion, hemodynamic collapse is common. In particular, hemodynamic collapse has a high probability of occurrence when open aortic cross-clamping is used to staunch blood flow. Although complete occlusion can stop distal blood loss, complete occlusion also causes supraphysiologic blood pressure spikes to everything upstream of the occlusion balloon. These blood pressure spikes can worsen concomitant injuries to tissue beds proximal to the balloon (e.g. traumatic brain injury, pulmonary contusions and hemorrhage, or traumatic amputations of the upper extremities). Additionally, upon uncontrolled release of complete occlusion, the blood volume supplying the heart, lungs, and brain is rapidly redistributed to the lower half of the body effectively reducing the circulating blood volume. Additionally, peripheral vasodilation and the washout of toxic metabolites, which have built up in the ischemic tissues, can result in myocardial suppression and further deterioration of hemodynamics. As a result, the growing clinical experience with REBOA in its current form reveals negative physiologic effects.

The current compliant balloon architecture poses technical challenges for incremental restoration of distal reperfusion necessary to prevent hemodynamic collapse following complete aortic occlusion. As an alternative to compliant balloon architectures, there exist fixed-diameter, non-compliant balloon catheter designs (e.g., ARMADA® by Abbott Laboratories Corp., North Chicago, Ill.). However, these catheters are intended and approved for vessel dilation (angioplasty), typically for narrowed vessels (e.g., atherosclerosis). Additionally, a fixed-diameter, non-compliant balloon catheter must be sized appropriately to properly occlude each patient's aorta. Consequently, although the non-compliant balloon is less susceptible to change in shape due to blood pressure spikes, the inability to change diameter outside of a narrow range impedes its ability to serve as an adaptable device to support both complete occlusion and partial occlusion. Therefore, the relatively fixed diameter of non-compliant balloon catheters limits their real-world applicability across a range of normal aortic diameters.

Other efforts have been directed to development of potential alternative methods of providing aortic occlusion. For example, Barbut et al., U.S. Pat. No. 6,743,196, issued Jun. 1, 2004, describes a plurality of approaches to support aortic occlusion. Each approach described in Barbut et al. includes a catheter having a distally mounted constricting mechanism. Each constrictor is collapsed to facilitate insertion and then expanded once inserted to obstruct blood flow. Barbut et al. describes a constrictor comprising an outer conical shell and an inner conical shell, each having a distal open base and proximal apex. The outer shell further includes a pre-shaped ring to facilitate expansion. Both shells include ports or openings. Flow through the mechanism is controlled by rotating the inner conical shell such that the ports of each shell communicate.

More recently, VanCamp et al, in U.S. Pat. No. 7,927,346, issued Apr. 19, 2011, describes a device to provide temporary partial aortic occlusion to achieve diversion of blood flow to the brain in patients suffering from cerebral ischemia. The primary thrust of the VanCamp et al. invention is the provision of an occlusion device that does not require fluoroscopy to ensure proper placement. VanCamp's device includes an expandable frame with a planar membrane mounted on a first portion of the frame to occlude blood flow. In one embodiment disclosed in VanCamp et al., the membrane includes a fixed size opening in the center of the planar membrane to allow some blood to flow through the opening. Alternatively, VanCamp also discloses that the membrane itself may be somewhat permeable to blood flow to allow some flow. However, VanCamp is unable to provide variable control of blood flow during use.

In light of the aforementioned considerations and limitations of existing and proposed devices, there exists an urgent and unmet need for a viable solution to allow a physician to address hemorrhagic injuries and carefully regulate blood flow, from complete occlusion to sustained partial occlusion, with an ability to adjust the level of occlusion as the patient's vital signs dictate.

SUMMARY

The present invention, in its several embodiments, comprises a medical device to control blood flow and pressure in a patient having hemorrhagic blood loss from a traumatic truncal wound, hereinafter the endovascular variable aortic control catheter ("EVACC") or "EVAC device". The various embodiments of the EVACC enable adaptable and variable aortic occlusion for controlling anterograde blood flow and augmenting blood pressure to vital organs, particularly in patients suffering from significant blood loss. A relevant example is a patient presenting with a traumatic hemorrhagic event, such as a gunshot wound to the abdomen. The EVAC device provides variable levels of aortic occlusion to control distal aortic blood flow and pressure on either side of an occlusion barrier established by the device.

As used herein, the terms "proximal" and "distal" are from the perspective of the physician or other medical professionals, such that "proximal" describes a direction away from a patient, while "distal" describes a direction toward the patient. For example, the end of a device that is inserted into a patient would be considered the "distal end"; the end held by the physician would be considered the "proximal end".

Further, as used herein, the terms "upstream" and "downstream" describe portions of the vascular system located on either side of the occlusion barrier. "Upstream" is in a direction away from the occlusion barrier toward the heart and associated vascularity; and "downstream" is away from the occlusion barrier to the remaining vascularity, i.e., systemic circulation, in communication with the site of hemorrhage.

Each of the various embodiments described herein is able to achieve more precise regulation of the degree of aortic occlusion and controlled incremental restoration of downstream reperfusion. Accordingly, one object of the various embodiments of the invention is to quickly staunch a source of bleeding. Another object is to reinitiate blood flow to deprived areas of the body while maintaining adequate flow and pressure in the vascularity serving the brain, lungs, and other critical organs.

A further object of the various embodiments of the invention is to allow a physician to safely transition a patient from a state of complete aortic occlusion to a plurality of levels of partial aortic flow and back and forth between complete occlusion and a plurality of levels of partial flow. The invention will allow a physician to wean a patient between various states of partial aortic flow to promote a more effective process for promptly responding to the patient's varying physiologic and vascular conditions.

Yet another object of the various embodiments of the invention is to allow a physician to wean a patient dynamically in real-time to respond to a patient's changing physiologic conditions. A further object of the various embodiments of the invention is to allow controlled distal reperfusion as required to minimize the likelihood of reperfusion injury associated with tissue ischemia associated with aortic occlusion. Another object of the various embodiments of the invention is to support patients suffering from other non-hemorrhagic causes of shock including, but not limited to, sepsis, cardiogenic shock, and spinal shock.

Not all of the objects described above need be accomplished in aggregate by any one or more of the various embodiments of the invention. Each of the objects may be accomplished individually or in combination with other objects by any one of the embodiments according to the invention. Consequently, interpretation of the claims herein should not be limited by any one or more of the objects addressed above.

Thus, in accordance with embodiments of the present invention, an endovascular variable aortic occlusion device is provided that comprises a central guide wire; a distal end potion that includes a first wire framework and an occlusion barrier; a delivery sheath, and a proximal end portion that includes a hand piece having a stationary portion and a movable portion. The first wire framework of the distal end portion is radially expandable and collapsible. The wire framework is configured to radially expand to a sufficient radial circumference to engage with an aortic wall within a lumen of an aorta to secure the device within the aorta. The occlusion barrier surrounds at least a portion of the first wire framework and is attached thereto to provide a cup-shaped occlusion barrier, such that an upper perimeter of the occlusion barrier contacts the aortic wall when the wire framework is radially expanded. The occlusion barrier also includes at least one adjustable passageway therein to facilitate controlled anterograde blood flow. The delivery sheath is extensible and retractable, wherein a collapsed form of the first wire framework is contained therein during delivery of the device into the lumen of the aorta. The movable portion of the hand piece controls a translational movement of the delivery sheath relative to the wire framework to enable unsheathing and radial expansion of the first wire framework. The movable portion of the hand piece may also be configured to adjust the at least one adjustable passageway to regulate controlled anterograde blood flow.

Each of the various embodiments described herein have common elements that support the delivery of an effective occlusion barrier, but each of the embodiments has slightly different movable elements for controlling the adjustable passageway to regulate controlled anterograde blood flow. As appropriate, additional detail associated with each of the described embodiments will focus on the specific movable structural elements that provide control of anterograde (or downstream) blood flow rather than the common elements. Following is a listing of the various embodiments of the invention described herein, named in reference to their movable structural elements that enable flow control: 1) Fenestrated cylindrical conduit ("FCC"); 2) Single aperture reduction ("SAR"); 3) Captive balloon ("CB"); 4) Fenestrated cone ("FC"); 5) Peripheral internal constriction ("PIC"); 6) Lasso aperture closure ("LAC"); 7) Rotating cup ("RC"); and 8) Deformable cup ("DC").

In a first embodiment, identified herein as a Fenestrated Cylindrical Conduit (FCC), the EVACC comprises a catheter-based system having a proximal hand piece for controlled deployment and operation of a distal portion of the device, wherein the distal portion is used to both partially and completely occlude the aorta. The distal portion of the EVACC comprises the components necessary to create an occlusion barrier within a targeted blood vessel, e.g., the aorta. In this first embodiment, a cylindrical conduit having a plurality of orifices (i.e., a fenestrated cylindrical conduit) extends proximally from a bottom of the occlusion barrier. Regulation of anterograde blood flow is achieved by translational movement of the delivery sheath relative to the occlusion barrier to change a number of orifices in an uncovered state to adjust an available flow area for blood flow. In one aspect, the occlusion barrier may comprise an expandable and collapsible impermeable membrane that is supported by an expandable and collapsible egg-shaped memory wire architecture. When deployed to occlude a blood vessel, the memory wire architecture expands the impermeable membrane to form a cup-shaped occlusion barrier. The conduit and the occlusion barrier may be formed as a unitary body or may be discreet components joined together (e.g., by glue, thermal fusion, or a mechanical mating arrangement, for example).

The collapsible membrane and associated memory wire architecture are deployed into a vessel through a delivery sheath. During use, when deployed out the end of the delivery sheath, the memory wire architecture and an upper perimeter of the cup of the collapsible membrane expand to the size of the lumen of the blood vessel, e.g., the aorta, creating a barrier or restriction to flow. The cup-shaped occlusion barrier funnels flow into the cylindrical fenestrated conduit. The fenestrated conduit has a plurality of orifices or perforations that can be exposed or covered to support variable downstream flow to systemic circulation. Linear translation of the delivery sheath causes the orifices in the fenestrated conduit to be exposed or covered. Thus, the EVACC is able to control the rate of blood flow through the orifices or fenestrations below the occlusion barrier as well as the blood pressure on either side of the occlusion barrier. Once the occlusion barrier is fully deployed within the aorta, the delivery sheath may be retracted in a controlled and graded fashion to uncover one or more orifices in the fenestrated conduit, thereby allowing blood to flow from a higher-pressure upstream vascular region to a lower pressure downstream systemic vascular region.

In a second embodiment of the invention, identified herein as a Singled Aperture Reduction (SAR), the movable elements for controlling the adjustable passageway to regulate controlled anterograde blood flow is based on aperture reduction and/or enlargement via linear translation of the delivery sheath over a neck of the wire basket architecture. From its top perimeter, the cup of the occlusion barrier narrows to a single circular aperture whose size is variably adjusted by the advancement or retraction of the delivery sheath toward or away from the aperture. As the delivery sheath is moved towards the aperture, the wires of the supporting wire basket architecture are drawn close together to converge, and the diameter of the aperture is likewise reduced, restricting flow through the aperture, and reducing downstream systemic circulation. To increase flow, the delivery sheath is moved away from the aperture, enlarging the aperture and hence, the flow area.

In a third embodiment, identified herein as Captive Balloon (CB), the movable elements for controlling the adjustable passageway to regulate controlled anterograde blood flow include an inflatable obstructive member (e.g., a captive balloon) extending into a single circular orifice, where inflation or deflation of the inflatable obstructive member adjusts a diameter of the portion of the inflatable obstructive member extending into the orifice to change an available flow area for anterograde blood flow. In one aspect, the single orifice may extend into an impermeable cylindrical conduit, such that the captive balloon is within the conduit. Rather than tapering down to a fenestrated conduit, the impermeable cylindrical conduit is internally occupied by a corresponding cylindrical balloon. The cylindrical conduit may have limited expansion. The balloon may be inflated to varying degrees within the conduit to variably occlude the lumen of the conduit, thus increasing resistance to flow and flow restriction. Complete occlusion is accomplished by full inflation of the balloon within the cylindrical conduit.

In a fourth embodiment, identified herein as Fenestrated Cone (FC), the movable elements for controlling the adjustable passageway to regulate controlled anterograde blood flow include a conical conduit having a plurality of orifices (i.e., a fenestrated cone) extends proximally from a bottom of the occlusion barrier. Regulation of anterograde blood flow is achieved by translational movement of the delivery sheath relative to the occlusion barrier to change a number of orifices in an uncovered state to adjust an available flow area for blood flow. The proximal region of the cup of the occlusion barrier tapers to a conically-shaped fenestrated conduit, rather than the cylindrical fenestrated conduit described above. As with the first embodiment, retraction or deployment of the conical portion out of the sheath regulates flow by causing the fenestrations to be covered or exposed and the diameter of the conical portion to be reduced as the sheath is linearly translated to cover more of the conically-shaped conduit.

In a fifth embodiment, identified herein as Peripheral Internal Constriction (PIC), movable elements for controlling the adjustable passageway to regulate controlled anterograde blood flow include a conduit portion comprising an elastomeric wall that extends proximally from the occlusion barrier; and a wire mesh structure comprising a cylindrical, helically-wound braid that is surrounded by the elastomeric wall of the conduit portion. This configuration is akin to a "finger trap" design. The proximal region of the cup of the occlusion barrier tapers to this conduit portion, whose interior incorporates a wire mesh structure (e.g., a helically-wound braid) anchored to a central structural wire. The proximal portion of this conduit portion is open to allow downstream flow. The wire mesh structure or architecture may be constructed of a shape memory material, such that in its native state, the conduit portion is open. Retraction on the cylindrical conduit portion results in elongation and diameter reduction, but does not disrupt the upper perimeter of the occlusion barrier's apposition to the aortic wall. Instead, mechanical retraction of the conduit pulls against a point of fixation on a central structural wire. By elongating and narrowing the conduit portion, flow through the device is variably restricted.

In a sixth embodiment, identified herein as lasso aperture closure (LAC), the movable elements for controlling the adjustable passageway to regulate controlled anterograde blood flow include a lasso aperture constriction. The proximal region of the cup-shaped occlusion barrier narrows to an aperture or orifice that is variably restricted in diameter by the retraction of wires. In one embodiment, a lasso wire is provided that includes a distal end wire segment configured in a semi-circle having two end portions, and a wire portion extending from each end portion and terminating at the movable portion of the hand piece. The first wire framework passes through the semicircle of the distal end wire segment. An overlapping portion extending from the proximal terminal end of the occlusion barrier conforms to the distal end wire segment and thereby forms a single circular orifice at the proximal terminal end of the occlusion barrier. Retraction (or possibly rotation) of the wire portions extending from the end portions controls the size of the orifice. This function is similar to closing of a noose in a lasso.

In a seventh embodiment, identified herein as rotating cup (RC), movable elements for controlling the adjustable passageway to regulate controlled anterograde blood flow include two cup-shaped membranes where a first cup-shaped membrane has a first set of openings and a second cup-shaped membrane has a second set of openings. The adjustable passageway is formed by rotational alignment of the first and second set of openings to coincide, where at least one of the first or the second cup-shaped membrane is coupled to the movable portion of the hand piece. A rotational motion of the movable portion of the hand piece causes a relative rotation between the first and the second cup-shaped membrane to vary a degree of coincidence between the first and second set of openings. In one embodiment, the second (downstream) cup membrane includes a set of openings (e.g., two slots) to allow flow when the openings are uncovered, and is supported by the first wire framework. The first (upstream) cup membrane also includes a set of openings, and is supported by a second wire framework and may be rotated in either direction to cover or uncover the openings in the second cup membrane to restrict or increase blood flow, respectively.

In an eighth embodiment, identified herein as deformable cup (DC), the movable elements for controlling the adjustable passageway to regulate controlled anterograde blood flow include two mating cup-shaped membranes, where an inner cup is deformable. The occlusion barrier includes a first cup-shaped membrane bonded to the first wire framework, where interstitial openings are present around a perimeter of the first cup-shaped membrane; and a second cup-shaped membrane positioned upstream relative to the first cup-shaped membrane. The second cup-shaped membrane includes a central aperture in a bottom portion, and the second cup-shaped membrane conforms to a distal surface of the first cup-shaped membrane, and wherein the central aperture in the second cup and the interstitial openings in the first cup do not coincide when mated together. In one aspect, the two mating cups may be supported by a single wire basket architecture. The second cup-shaped membrane may include a flexible impermeable membrane having a central aperture. The aperture may be linearly reciprocated back and forth, creating various toroidal shapes and uncovering or covering the interstitial openings within the downstream cup. In a fully closed state, the second (upstream) cup-shaped membrane adapts to the shape of the first (downstream) cup-shaped membrane, such that the interstitial openings are fully covered by the upstream membrane and flow is occluded. Flow is increased by linear translation of a center wire to lift the center aperture, and a portion of the surrounding circumferential area, of the upstream membrane off the downstream occluding element, causing the interstitial openings between the petals of the first occluding element to be uncovered, thereby allowing flow to occur.

BRIEF DESCRIPTION OF THE SEVERAL VIEWS OF THE DRAWINGS

These and other features, aspects and advantages of various embodiments of the present invention will become better understood with regard to the following description, appended claims, and accompanying drawings where:

FIGS. 9A, 9B, and 9C show side enlarged side views of an embodiment of the variable and adaptable aortic occlusion apparatus in use inside a major blood vessel of the body, wherein FIG. 9A shows the apparatus prior to deployment, FIG. 9B shows the apparatus deployed for full occlusion, and FIG. 9C shows the apparatus deployed for partial occlusion;

Figure 1:
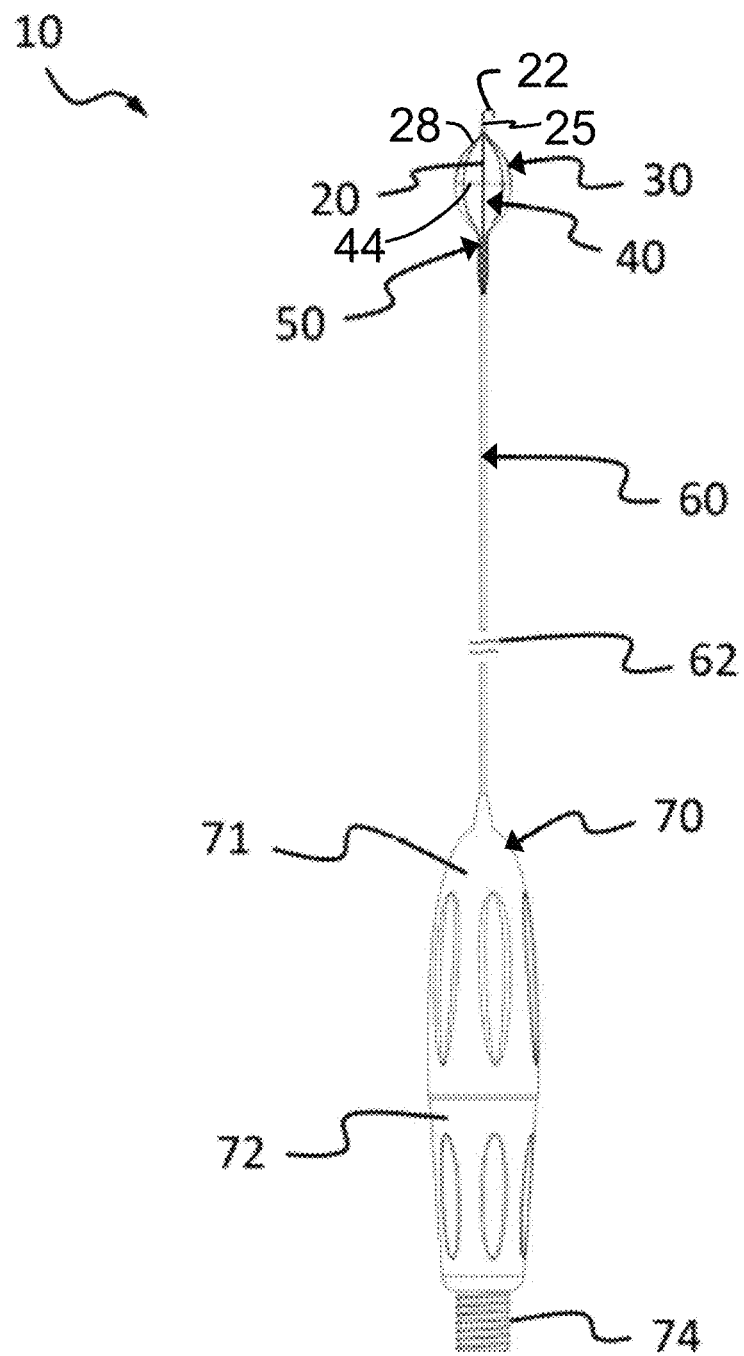
FIG. 1 is a rear elevation view of an embodiment of the variable and adaptable aortic occlusion apparatus.

The accompanying drawings numbered herein are given by way of illustration only and are not intended to be limitative to any extent. Commonly used reference numbers identify the same or equivalent parts of the claimed invention throughout the accompanying drawings.

DETAILED DESCRIPTION

Following is a listing of the various embodiments of the endovascular variable aortic control catheter (hereinafter, "EVACC") described herein, named in reference to movable elements used to control, regulate, and/or modulate anterograde blood flow and identified by their shortened acronym and associated reference numeral.

Fenestrated Cylindrical Conduit Embodiment (EVACC 10): FIGS. 1-6

Figure 2:
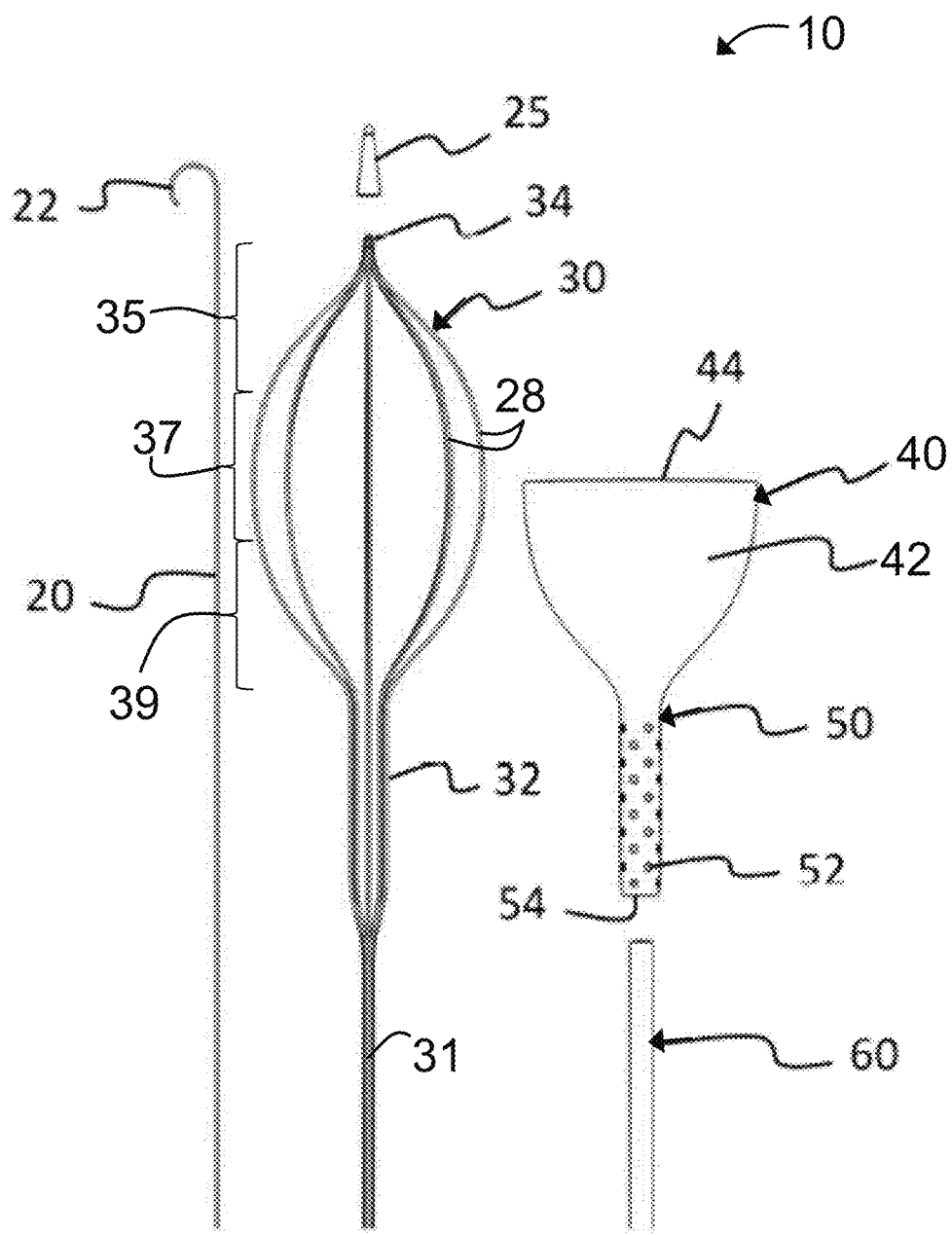
FIG. 2 is an enlarged front elevation view of the distal end portion of the apparatus shown in FIG. 1.
Figure 3:
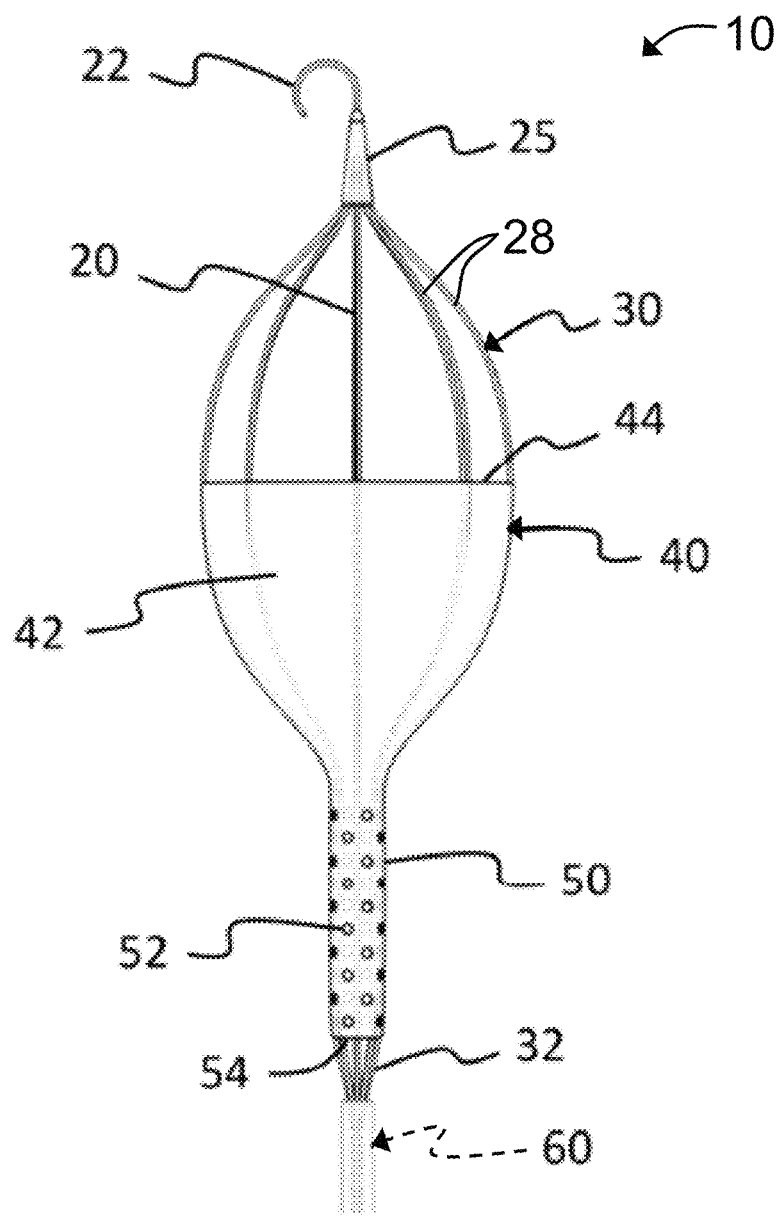
FIG. 3 is an enlarged front elevation view thereof.

Turning now to FIGS. 1-3, an endovascular variable aortic control catheter (EVACC) 10 according to a first embodiment of the present invention is illustrated, wherein anterograde blood flow is controlled or regulated using a fenestrated neck 50, hereinafter referred to as EVACC 10.

The EVACC 10 comprises a longitudinal body 31 having a proximal end (not shown) and a distal end 33, a supporting memory wire basket 30, and an occlusion barrier 40.

The wire basket 30 includes a plurality of ribs 28 that may be made of nitinol or other material having similar memory-shape properties. As illustrated, the wire basket 30 having a radially expanding distal end 35, a medial expanded portion 37, a radially collapsing proximal end 39, and a proximally-extending neck 32. The ribs 28 of the wire basket 30 are configured to be collapsible (see FIG. 8A) and further configured to assume an approximately egg-shape when fully deployed and released from a delivery sheath 60, as illustrated in FIGS. 1-3. It should be appreciated that other shapes, e.g., spherical or cylindrical, are further contemplated. The ribs 28 of the wire basket 30 expands when deployed out the end of the delivery sheath 60 and will collapse upon retraction back into the delivery sheath 60. According to some embodiments, a nose cone 25 may be coupled to the distal end 35 of the wire basket 30 to provide smooth advancement of the EVACC 10 through the arterial tree during deployment. The nose cone 25 may be constructed of a radiopaque materials to allow tracking during use with appropriate medical imaging equipment.

The occlusion barrier 40 comprises a membrane, preferably made of expanded polytetrafluoroethylene (hereinafter, "ePTFE"). Other materials, such as polyester, may also be used to form the occlusion barrier 40. The occlusion barrier 40 is configured to be collapsible (see FIG. 8A) and further configured to expand to form a cup-like body 42, as illustrated in FIGS. 1-3. The deployed occlusion barrier 40 includes a distal perimeter 44, the cup-like body 42 extending from the distal perimeter edge 44, and a proximally-positioned fenestrated neck 50.

The fenestrated neck 50 includes a plurality of orifices or perforations 52 distributed along its length and is configured to such blood may flow therethrough when the orifices or perforations 52 not covered by the delivery sheath 60. The fenestrated neck 50 is preferably made of ePTFE, but may be made of other materials to increase rigidity or elasticity during deployment. In one aspect, the occlusion barrier 40 comprising the cup-like body 42 and fenestrated neck 50 form one unitary piece. In another aspect, the occlusion barrier 40 may comprise a separate cup-like body 42 and fenestrated neck 50, which are joined or bonded by various means, such as glue, thermal fusion or a mechanical mating arrangement.

Figure 4:
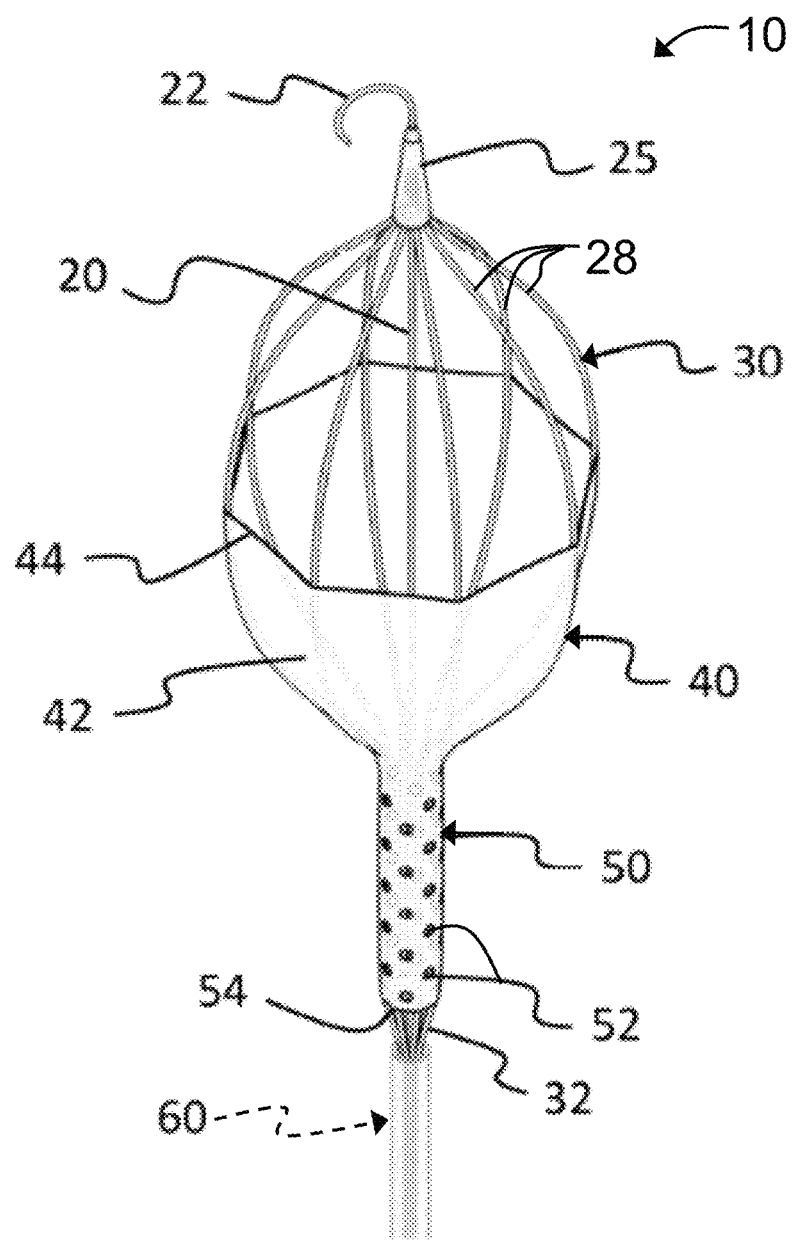
FIG. 4 is an enlarged fragmentary view taken from the view of FIG. 1.

FIG. 4 is a perspective view of the view of FIG. 3. As shown, the cup-like body 42 of the occlusion barrier 40 appears as being comprised of chords of membrane extending between ribs 28 of the wire basket 10. In practice, the perimeter 44 and the cup-like body 42 will blossom to appose an inner arterial wall. The blossoming effect occurs as a result of the memory-shape properties of the ribs 28 of the wire basket 10 and pressure differential caused by blood flow, which causes the occlusion barrier 40 to expand in the manner similar to a wind sock.

Figure 5:
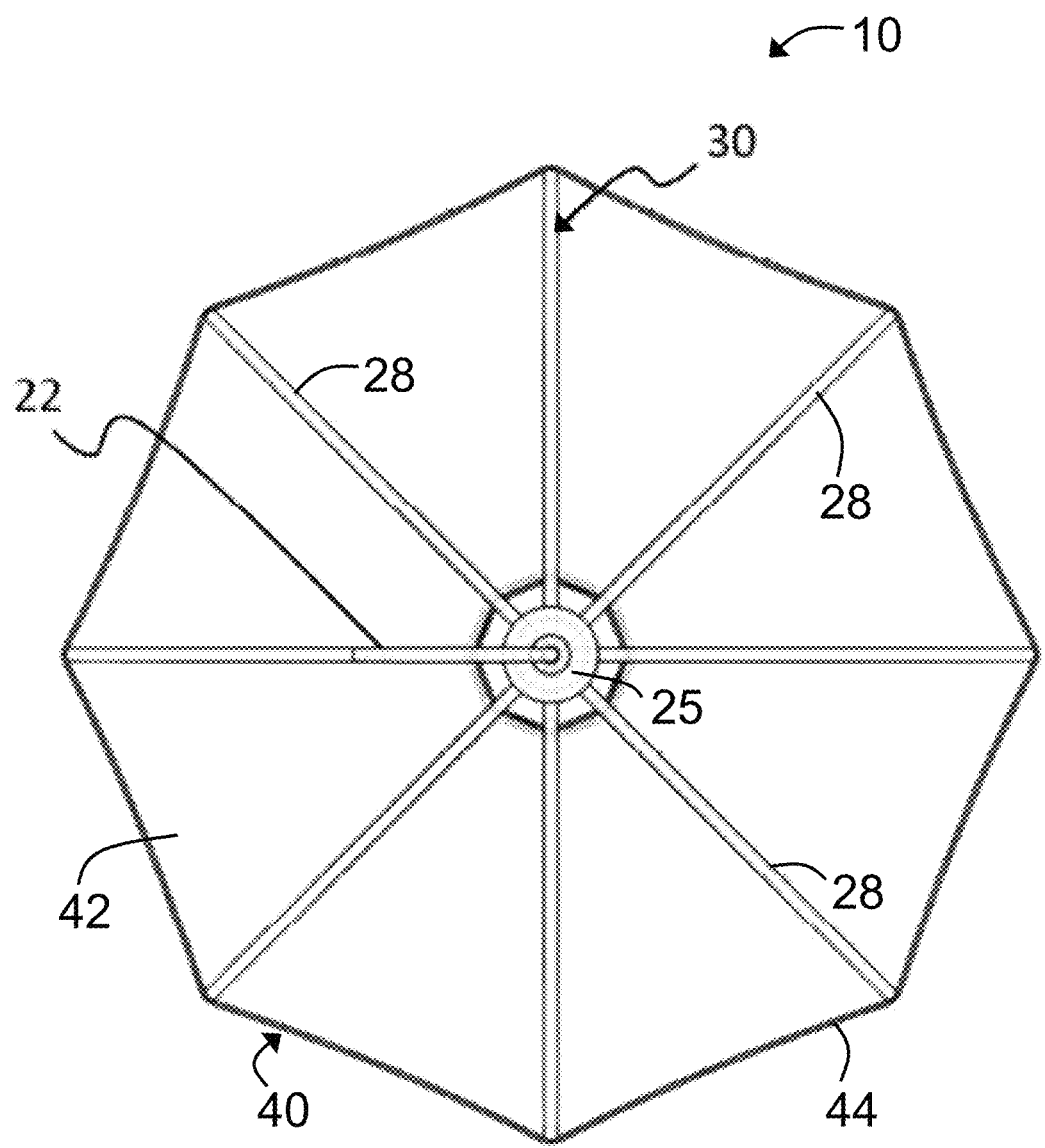
FIG. 5 is a top plan view thereof.
Figure 6:
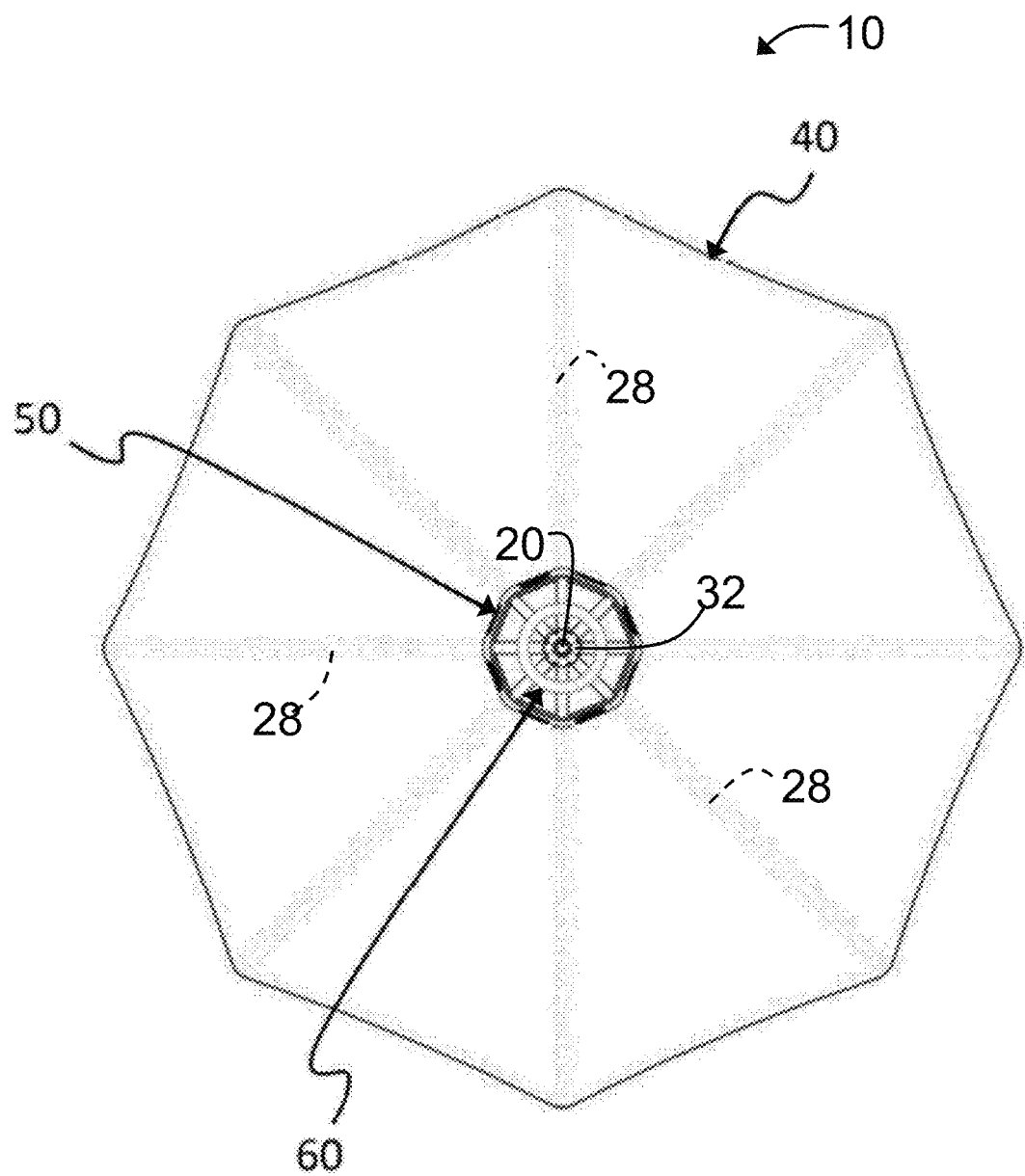
FIG. 6 is a bottom plan view thereof.

FIG. 5 is a top plan view of the EVACC 10, emphasizing the view into the cup-like body 42 of the occlusion barrier 40 in a fully deployed state with the J-tip 22, the conical tip 25 and the internal wire basket 30. FIG. 6 is a bottom plan view of the EVACC 10, emphasizing a lengthwise view from the distal end of the EVACC 10 in a fully deployed state.

The EVACC 10 may be used with a guide wire 20 and the delivery sheath 60. In that regard, the guide wire 20 may extend through a lengthwise central axis of the longitudinal body 31, the wire basket 30, and distally from the distal end 33 of the longitudinal body 31. The delivery sheath 60 is configured to surround and be in slidable relation with the guide wire 20, the wire basket 30, and the occlusion barrier 40.

Now, in greater detail, FIG. 2 is an enlarged view of the EVACC 10 of FIG. 1. The guide wire 20 is a self-centering rigid endovascular guide wire 20 used to reach a target occlusion location within a patient's vascular system. The endovascular guide wire 20 includes a J-tip 22 at a distal end 34 thereof. The J-tip 22 ensures that the distal components of the EVACC can be smoothly advanced or retracted within the arterial complex to reach a desired location for occlusion. The J-tip 22 provides centering of the guide wire 20 and the delivery sheath 60 within the lumen of the artery.

Turning now to FIG. 3, a side elevation view of the distal components of the EVACC 10 in an assembled and deployed state is shown. The ribs 28 of the wire basket 30 are fully deployed, expanding the occlusion barrier 40 to create the cup-like body. The neck 32 of the memory wire 30 is deployed beyond the end of the delivery sheath 60 to expand the fenestrated neck 50 and the proximal end 54 of the neck 52 and uncover the perforations 52.

Figure 7:
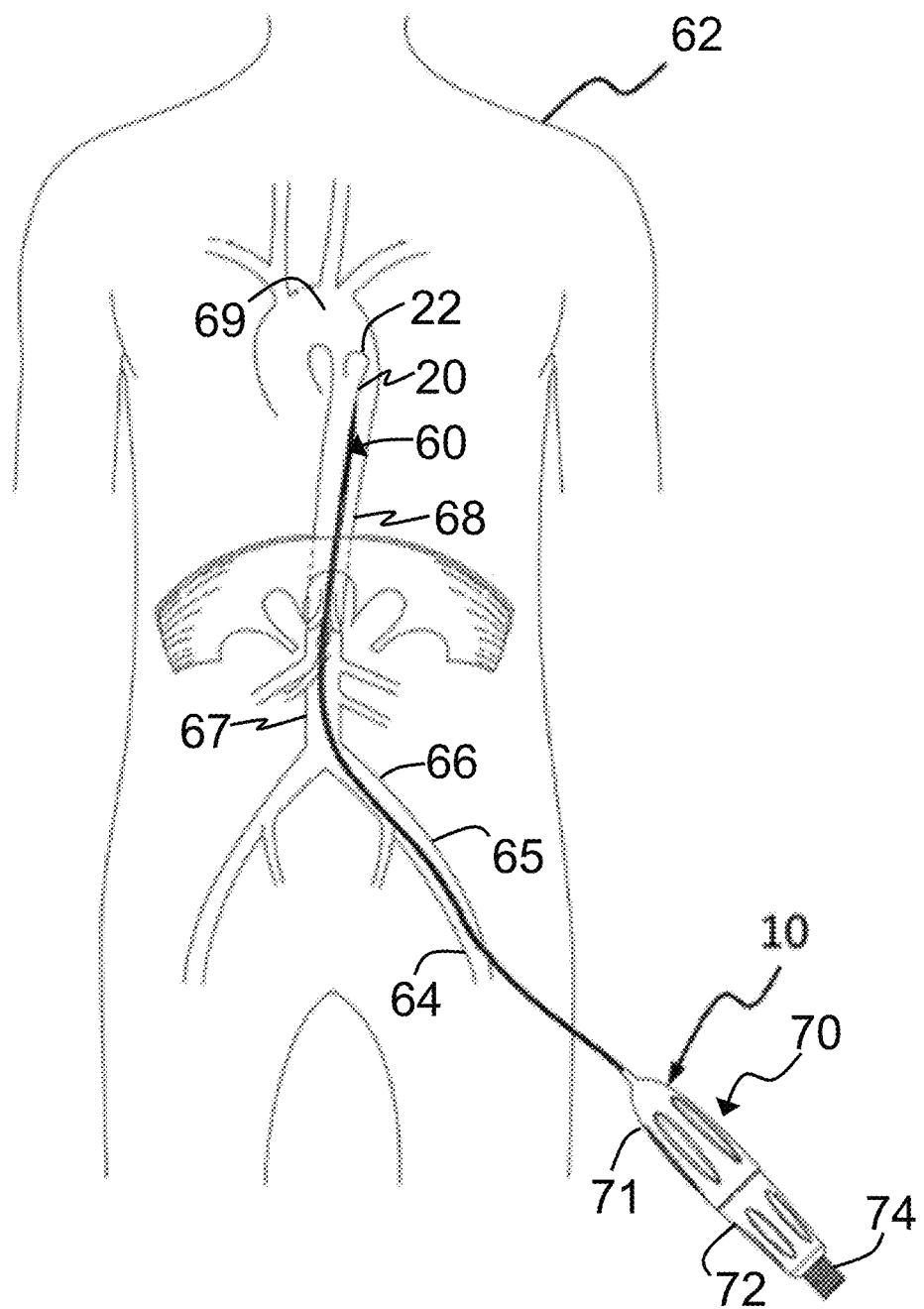
FIG. 7 shows the variable and adaptable aortic occlusion apparatus of FIG. 1 in use in a human body.

FIGS. 7-9 provide illustrations of the EVACC 10 in use and operation. The description provided regarding use and operation of this first embodiment, the EVACC 10, is applicable to the use and operation of the various additional embodiments described herein.

FIG. 7 is a simplified illustration of a method used to deploy the EVACC 10 in a patient 62. The central guidewire 20 and is inserted into an incision (not shown) in the femoral artery 64 and guided through the exterior iliac artery 65, the common iliac artery 66, the abdominal aorta 67, the thoracic aorta 68, and up to the aortic arch 69 or until reaching a targeted occlusion location (illustrated as being at about the thoracic aorta 68). The delivery sheath 60 with the EVACC 10 may then be directed over a proximal end of the guide wire 20, along the length of the guide wire 20 to the targeted occlusion location. The EVACC 10 is preferably inserted into the arterial tree through a 7-French sheath or smaller. According to some embodiments, delivery sheath 60 and EVACC 10 are preferably deployed through a percutaneous introducer catheter (not shown) directly into the femoral artery.

During initial insertion into the arterial tree and through advancement to the desired occlusion site within the thoracic aorta 68, the central guide wire 20, the wire basket 30, the occlusion barrier 40, and the fenestrated neck 50 are initially enclosed in the delivery sheath 60, in a manner similar to vena cava filter deployment catheters. Once so positioned at the occlusion, the guide wire 20 and the EVACC 10 may remain stationary while the delivery sheath 60 is retracted, thereby deploying the wire basket 30 and the occlusion barrier 40. With the wire basket 30 and occlusion barrier 40 unrestrained by the delivery sheath 60, the wire basket 30 and occlusion barrier 40 assume natural, opened positions within the lumen of the thoracic aorta 68 such that the cup-like body 42 of the occlusion barrier and ribs 28 of the radially expanding distal end 35 of the wire basket 30 (and possibly of the medial expanded portion 37 and the radially collapsing proximal end 39) appose the inner wall of the thoracic aorta 68, thereby creating a sealing portion buttressed by the unfurling of the occlusion barrier 40.

The degree to which the fenestrated neck 50 is opened to allow flow is controlled by a hand piece 70 connected to a proximal portion of the EVACC 10 (outside the patient 62). An exemplary version of a hand piece 70 used to manipulate and control the distal components of the EVACC 10 is shown in FIG. 1. The hand piece 70 comprises a stationary distal grip 71 and a rotatable proximal grip 72. Proximal grip 72 is rotatable on threaded guide 74 to manipulate the distal components of the EVACC during and after deployment. Additional wire assemblies (not shown) may be threaded through a center lumen (not shown) of the threaded guide 74 to provide additional methods for actuating the distal components.

The degree of occlusion and flow control may be manipulated by covering and exposing the perforations 52 of the fenestrated neck 50 via advancement and retraction of the delivery sheath 60. The advancement and retraction of the delivery sheath 60 may be accomplished by rotary manipulation of the rotatable grip 72 of hand piece 70 to advance a threaded guide 74 in either a proximal or a distal direction. The stationary distal grip 71 and rotatable proximate grip 72 of the hand piece 70 are rotated in opposite directions to linearly translate the threaded guide 74, which is attached via pull wires (not shown) to the sheath 60 and/or the fenestrated cylindrical conduit 50.

The EVACC 10 and the additional embodiments described herein may be equipped with blood pressure measuring capabilities proximal and distal to the occlusion barrier 40 for measuring downstream and upstream blood pressure, respectively. The blood pressure measuring capabilities may comprise a manometer mounted on the EVACC 10 or a channel communicating with a transducer at the proximal end and a port at the distal end of the EVACC 10. Blood pressure measuring may also be accomplished by use of a fiber optic in vivo pressure transducer as described in U.S. Pat. Nos. 5,392,117 and 5,202,939, each of which is incorporated herein by reference in its entirety, or a Radi PRESSUREWIRE as described in U.S. Pat. Nos. Re 35,648; 5,085,223; 4,712,566; 4,941,473; 4,744,863; 4,853,669; and 4,996,082, each of which is incorporated herein by reference in its entirety.

With the inclusion of upstream and downstream pressure sensors, upstream and downstream blood pressure measurements may then be recorded and displayed via a monitor at a proximal end of the EVACC 10. A control device or module (not shown) may be programmed with various preferred treatment and operational parameters. The control device may then provide automated control of the operational parameters including: 1) blood pressure, upstream and downstream of the occlusion barrier 40, and 2) flow diversion through the uncovered perforations 52 of the fenestrated neck 50. For example, the control device can include a set pressure threshold to maintain upstream blood pressure to a desired level.

Data communicated to the pressure monitor from pressure sensors may be transferred or transmitted to the control device, which then sends control signals to a separate electrically-powered rotary unit to linearly translate the threaded guide 74 and the delivery sheath 60. The translational movement of the delivery sheath 60 by the threaded guide 74 controls exposure of perforations 52 in the fenestrated cylindrical conduit 50. The threaded guide 74 retracts or extends the delivery sheath 60 to uncover or cover the perforations 52, thereby adjusting the diversion of flow from upstream to downstream and causing modification of blood pressure on each side of the occlusion barrier 40.

In the field, where a separate automated control device may not be available, the hand piece 70 can be manually rotated to obtain desired upstream and downstream blood pressures. An audible alarm may be incorporated into the pressure monitor to sound when blood pressures exceeds desired thresholds. In one aspect, the rotary unit, pressure monitor, and control device may be integrated into the hand piece 70 of the EVACC 10.

The EVACC 10, and the additional embodiments described herein, are configurable to provide adaptive control of the means for flow regulation. Adaptive control is described in the context of the EVACC 10, but is intended to extend to the functionality of the additional embodiments described herein. In each embodiment, adaptive control is accomplished via manipulation of the various movable elements used for anterograde blood flow control.

Hence, in the case of the EVACC 10, adaptive control may be accomplished via the exposure or covering of the perforations 52 based on continuous dual pressure measurements both upstream and downstream of the occlusion barrier 40. Estimates of systemic flow may be determined via algorithms correlated to each EVACC 10 based on the pressure measurements. The real-time availability of both flow measurements and pressure measurements may then be used to inform either physician decisions or automated adaptive control of the EVACC 10 according to specified operational parameters. For example, just as a tourniquet is periodically released to allow flow to avoid further tissue damage, the EVACC 10 may operate via the automated control device to periodically adjust flow downstream of the occlusion barrier 40 to avoid ischemia, or, to reduce downstream flow to divert flow to the brain and other vital organs upstream of the occlusion barrier 40.

Figure 8A:
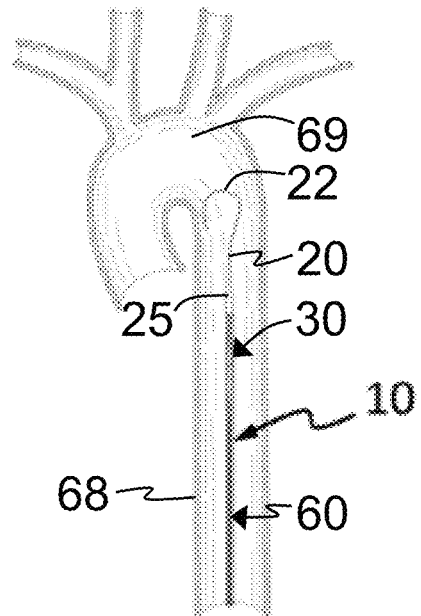
FIGS. 8A, 8B, and 8C show the variable and adaptable aortic occlusion apparatus of FIG. 1 in various stages of deployment inside an aorta.
Figure 8B:
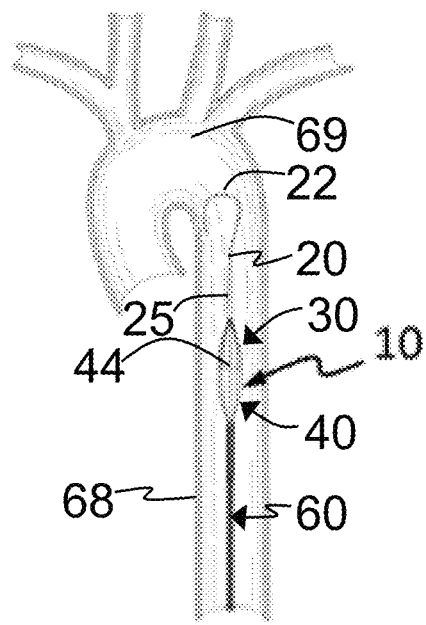
Figure 8C:
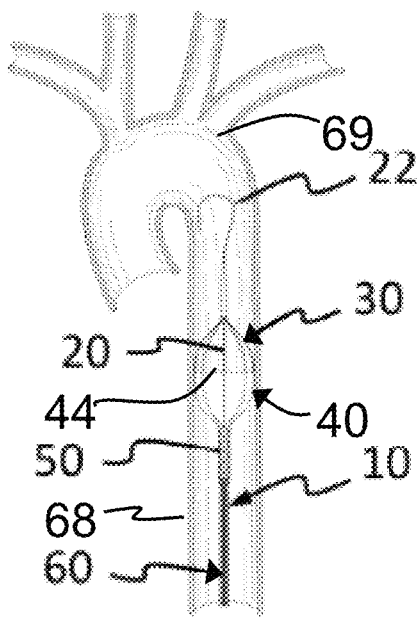
Figure 9C:
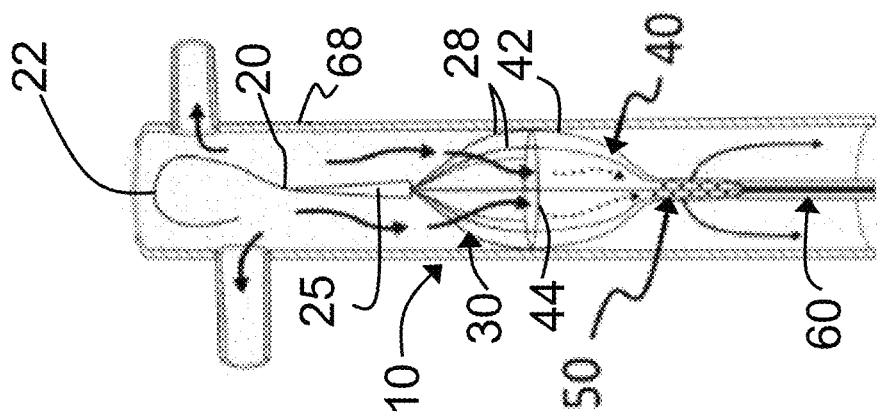
Figure 9B:
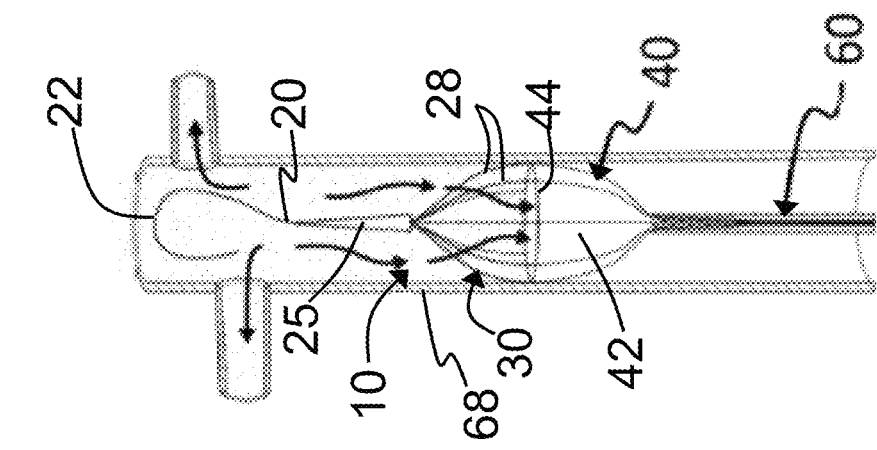

Turning now to FIGS. 8A through 8C, the deployment of the occlusion barrier 40 and wire basket 30 is shown. In FIG. 8A, the EVACC 10 has been positioned within the thoracic aorta 68 at a desired location. In FIG. 8B, the delivery sheath 60 has been retracted from over the wire basket 30, allowing the ribs 28 of the wire basket 30 and the cup-like body 42 of the occlusion barrier 40 to expand slightly. In FIG. 8C, the entire wire basket 30 and occlusion barrier 40 have been deployed out the delivery sheath 60 within the thoracic aorta 68 and the fenestrated neck 50 has been exposed outside the delivery sheath 60 providing an initial level of flow wherein the occlusion barrier 40 is operating in a full open state.

Figure 9A:
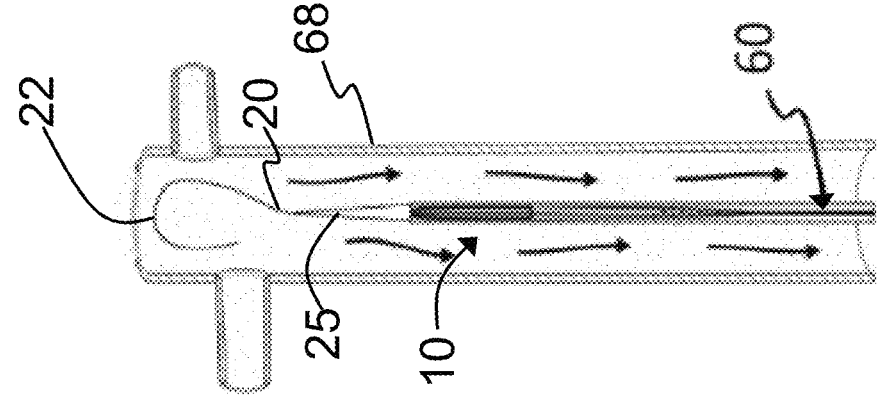

Turning now to FIGS. 9A though 9C, the manipulation of flow using the EVACC 10 is illustrated. In FIG. 9A, the wire basket architecture 30 and occlusion barrier 40 are both collapsed within the lumen of the delivery sheath 60 while positioned at a desired occlusion location. Note that the various arrows indicate the general distribution of blood flow during each of the described states, where blood is indicated by the dotted markings.

In FIG. 9A, with the EVAC 10 positioned at a desired location, flow continues to the site of hemorrhage with no occlusion or regulation of flow. Now, in FIG. 9B, the wire basket architecture 30 and occlusion barrier 40 are fully deployed out the distal end of the delivery sheath 60. In this configuration, the occlusion barrier 40 is deployed to appose the interior wall of the aorta A, but the fenestrated cylindrical conduit 50 is still fully covered by the delivery sheath 60, thereby causing full occlusion of downstream blood flow, with all existing flow redirected to upstream portions of the vascular. Now, in FIG. 9C, the delivery sheath 60 has been retracted to expose a portion of the fenestrated cylindrical conduit 50 and the perforations 52, providing an adjusted level of flow through the occlusion barrier 40, through the fenestrated conduit 50 and out the perforations 52 and downstream to support systemic circulation. Note that partial occlusion may distribute blood flow to other upstream elements of the vascular, while still allowing downstream flow.

The delivery sheath 60 may be advanced or retracted over the fenestrated cylindrical conduit 50 to continually adjust flow from fully occluded to various levels of partial occlusion. This ability to continually redistribute flow as required by a patient's physiologic status allows a surgeon to maximize the probability of survival and minimize potential negative outcomes, such as hemodyamic collapse, when weaning the patient off full or partial occlusion.

Now, several alternative embodiments are described in detail in the following paragraphs. In each alternative embodiment, the device is deployed and used in a similar fashion as described for the EVACC 10. However, in each alternative embodiment, the structure, configuration, and operation of movable elements used for flow control will differ to varying degrees.

Single Aperture Reduction Embodiment (EVACC 100): FIGS. 10-13

Figure 10:
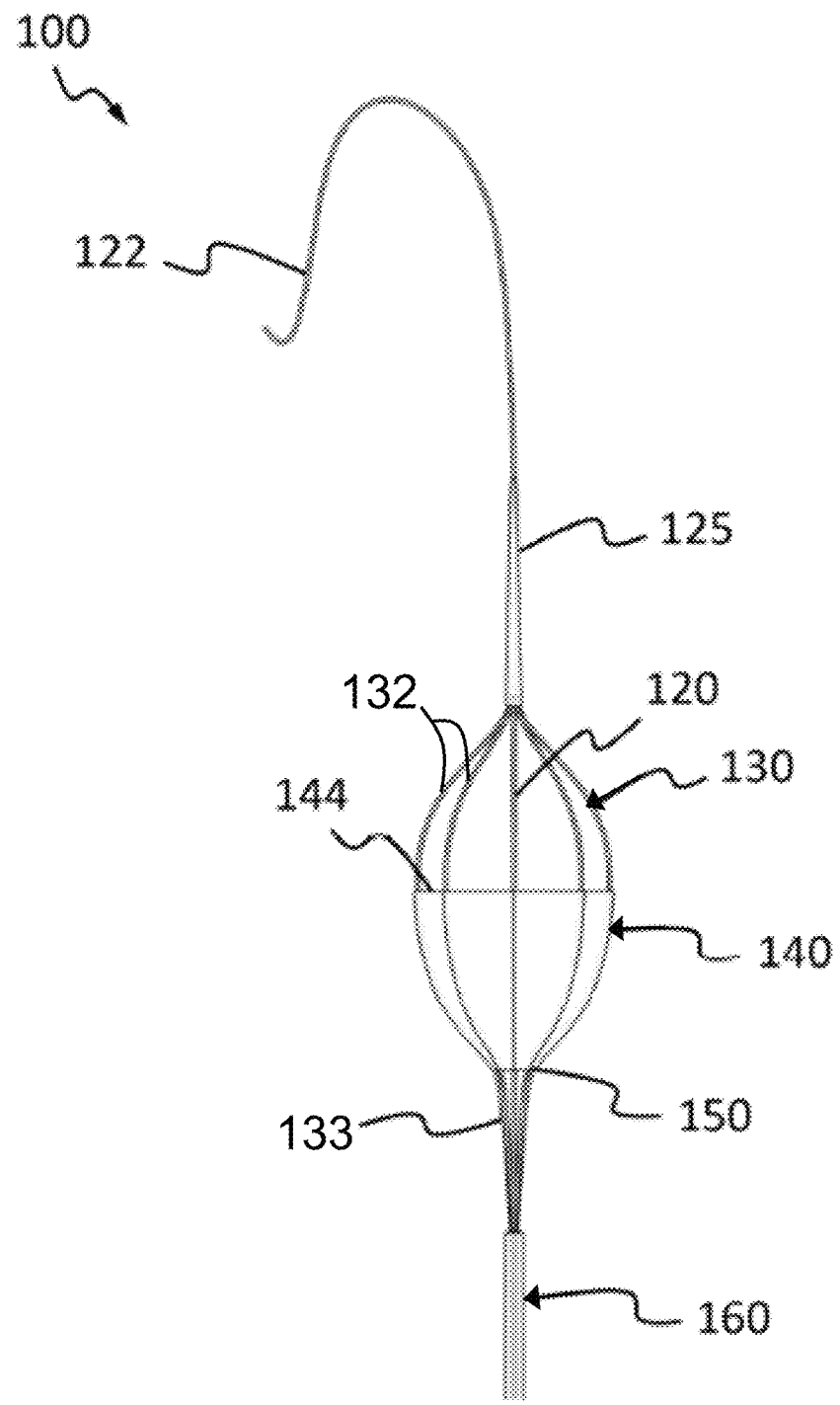
FIG. 10 is an enlarged front elevation view of an endovascular variable aortic control aperture device according to an embodiment of the present invention.

Referring now to FIG. 10, a second embodiment of the EVACC 100 is illustrated. The EVACC 100 comprises an anterograde blood flow control based on a single aperture reduction and includes a wire basket 130 and an occlusion barrier 140. The egg-shaped memory wire basket 130 supports a flexible cup-shaped occlusion barrier 140 having a perimeter 144 and a cup-shaped body 142 that narrows to a single aperture 150 having a maximum deployed diameter. The maximum deployed diameter of the single aperture 150 establishes the maximum flow rate through the occlusion barrier 140. The diameter of the single aperture 150 is reduced by the advancement of a delivery sheath 160 towards the single aperture 150, causing ribs 132 of the wire basket 130 to converge. As the ribs 132 converge, the diameter of the aperture 150 is reduced, thereby restricting flow through the aperture 150. As the delivery sheath 160 is retracted, the ribs 132 diverge to a deployed, memory state and the single aperture 150 is enlarged, thereby allowing increased flow. The EVACC 100 is fully occluded when the delivery sheath 160 is advanced to cover and envelop the single aperture 150.

Figure 11:
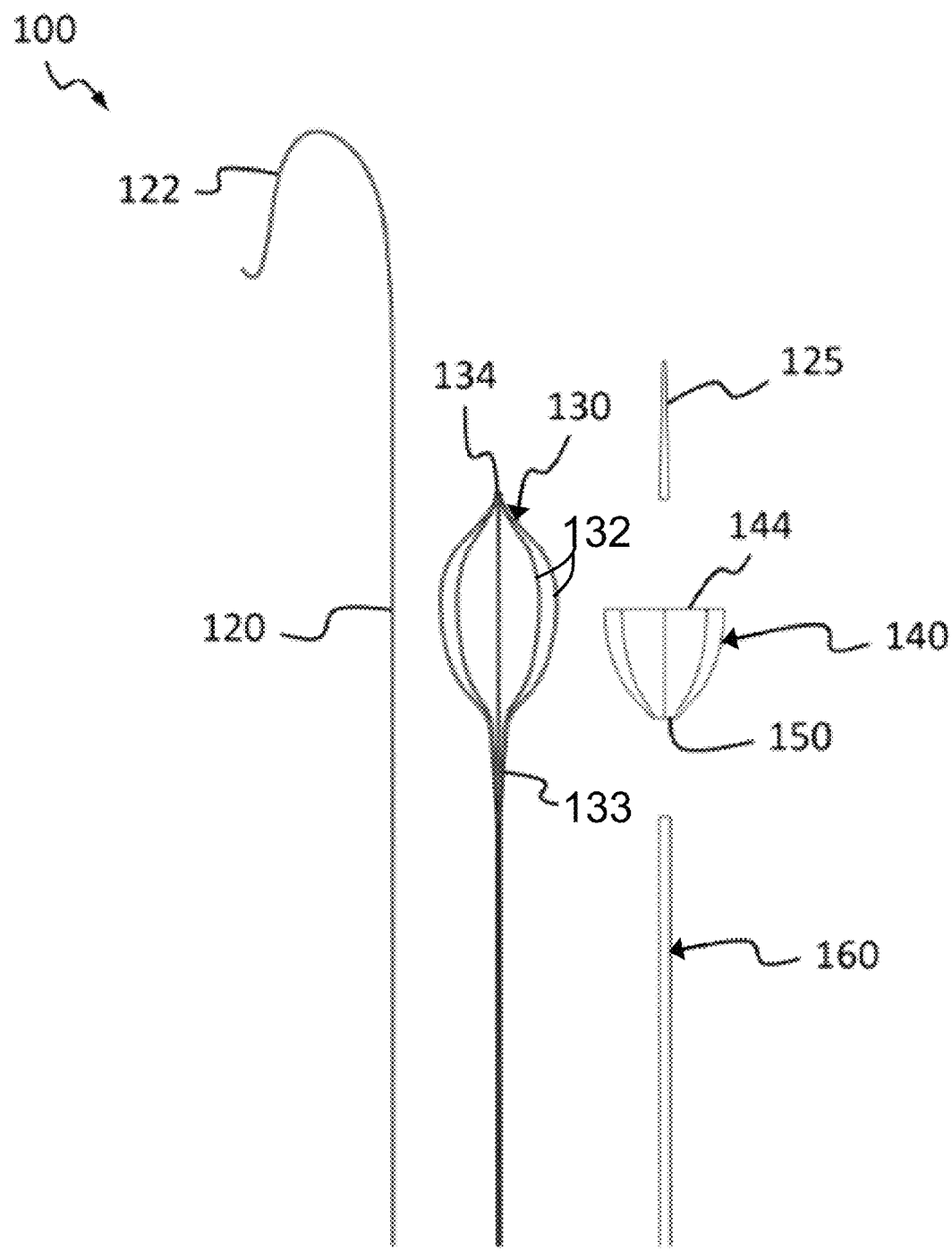
FIG. 11 is an enlarged front elevation view showing components of the device thereof.

Referring now to FIG. 11, an exploded view of the EVACC 100 with additional components are shown. The additional components may include a central guide wire 120 having J-tip 122, a tapered nose cone 125 for receiving the distal end 134 of a wire basket 130, and a delivery sheath 160. The wire basket 130 converges to a distal end 134, which is captured within a base of the tapered conical tip 125.

Figure 12:
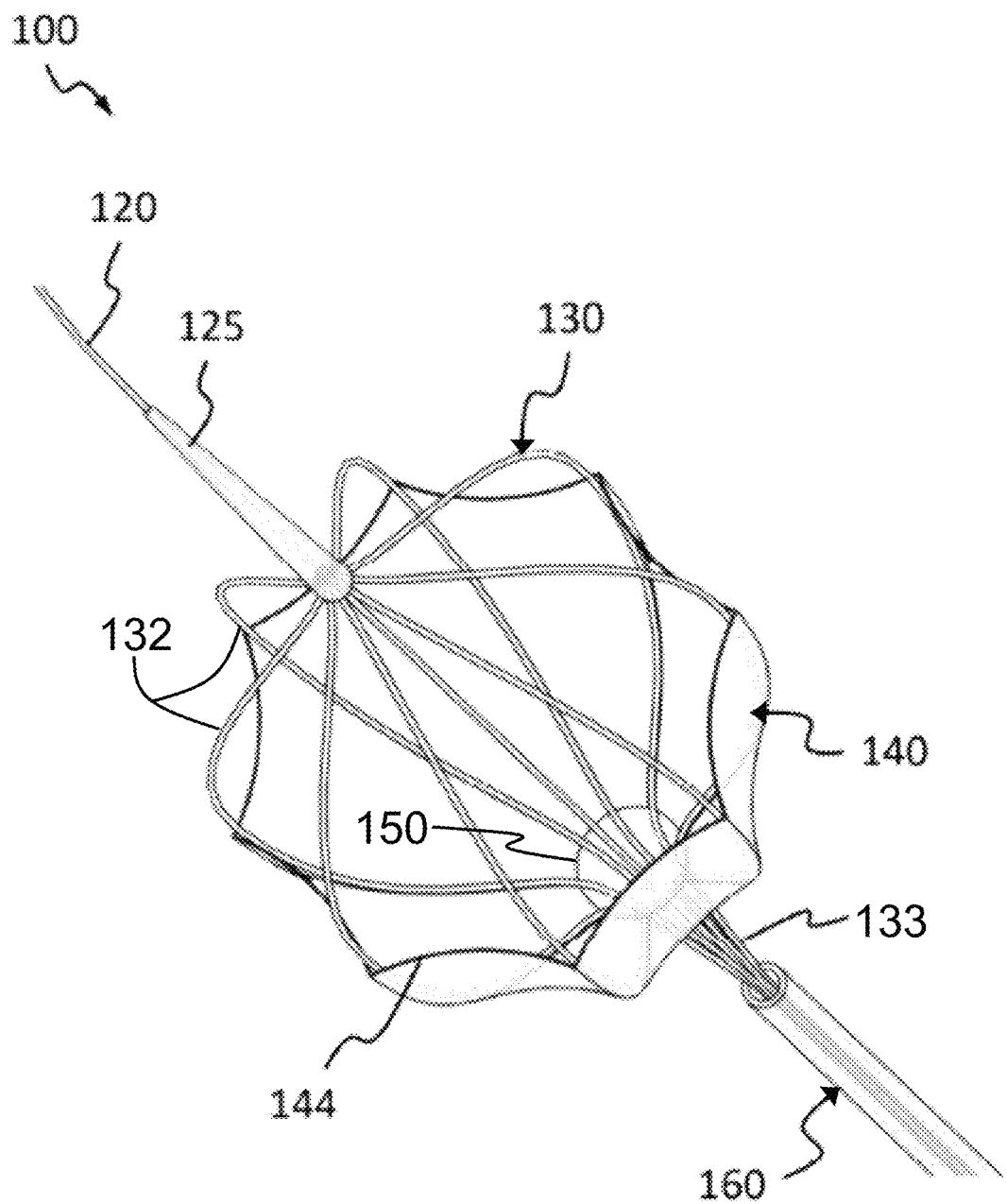
FIG. 12 is an enlarged fragmentary view thereof.

FIG. 12 is a perspective view of the EVACC 100 from the distal end to the proximal end. The ribs 132 extend through the single aperture 150 to deploy the occlusion barrier 140 via the wire basket 130. The occlusion barrier 140 is extended by the ribs 132 of the wire basket 130 to establish the perimeter 144 of the occlusion barrier 140.

Figure 13:
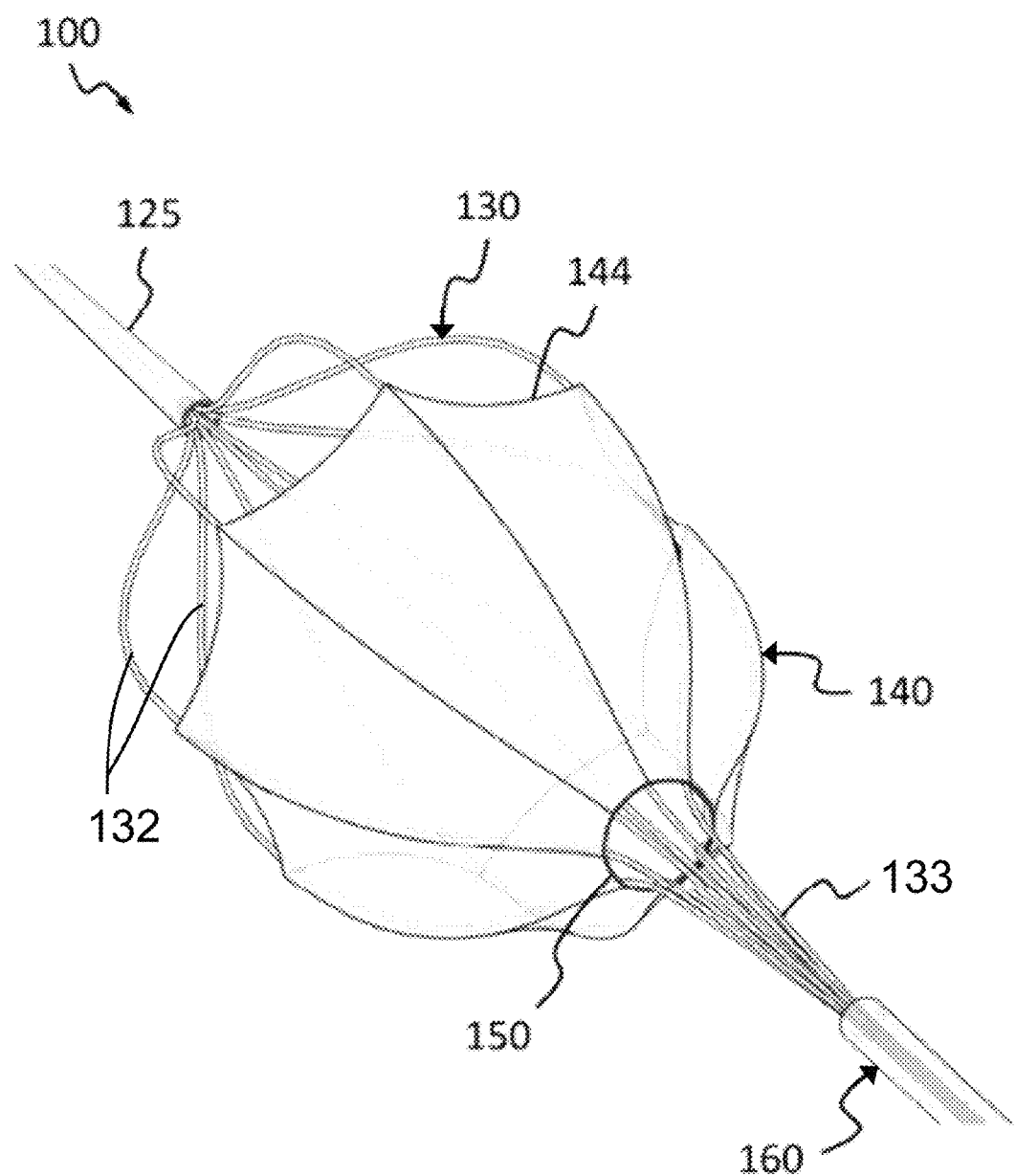
FIG. 13 is a second enlarged fragmentary view thereof.

FIG. 13 is another perspective view of the EVACC 100 from the proximal end to the distal end. The aperture 150 is joined to the supporting wires 133 so that as the supporting wires 133 are retracted into the sheath 160, the aperture 150 reduces in size. Once the supporting wires 133 have been fully retracted into the sheath 160 to up to the aperture 150, the aperture 150 is closed and flow is fully occluded. As with other embodiments, the amount of flow may be adjusted by advancing or retracting the sheath 160 over the aperture 150 and supporting wires 133 from a fully occluded state to a partially occluded state, thereby causing the aperture 150 to vary in size. In other versions of the EVACC 100, the aperture 150 may have a different size, which would modify the total flow through the aperture 150 in a fully deployed state.

Captive Balloon Embodiment (EVACC 200): FIGS. 14-17

Figure 14:
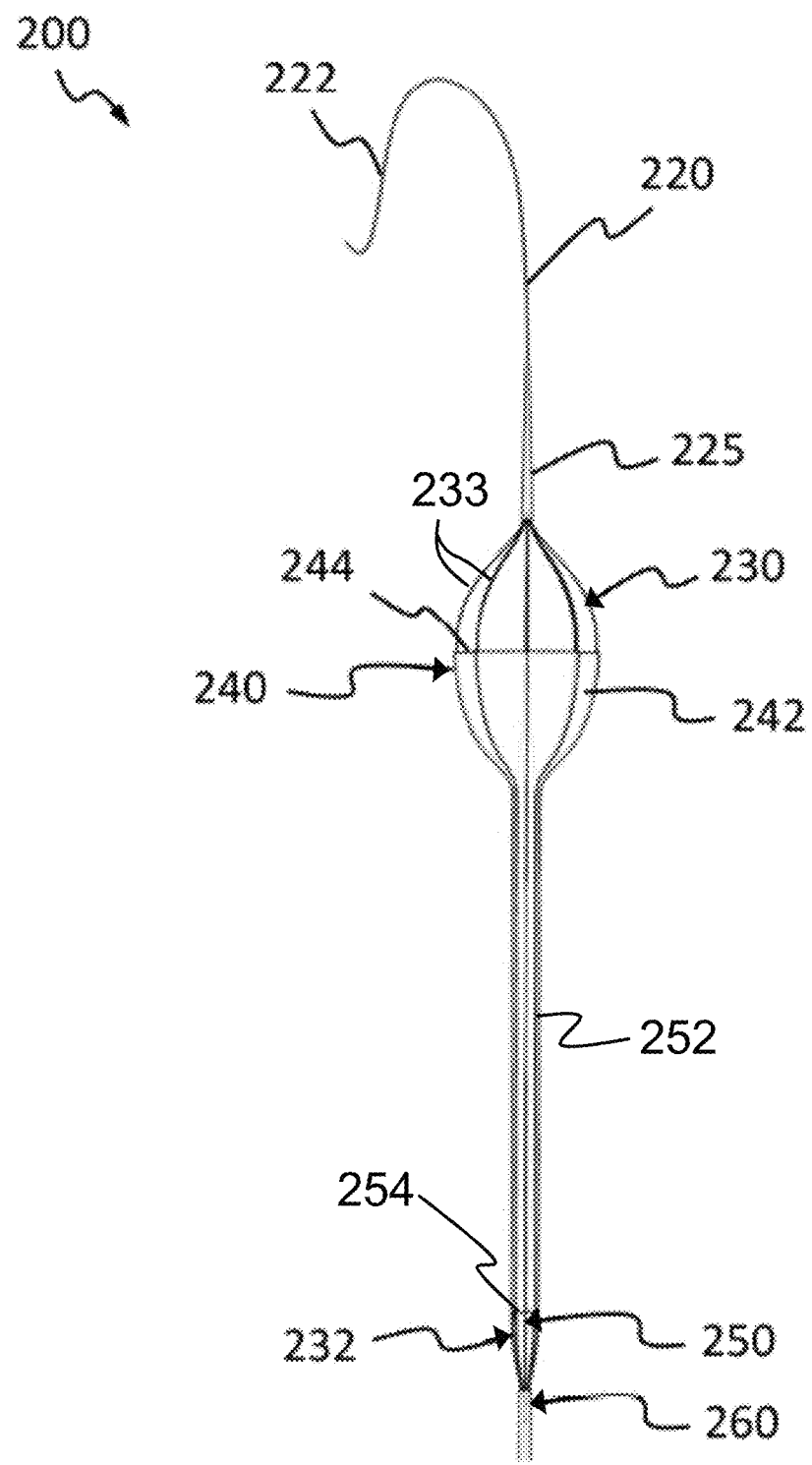
FIG. 14 is an enlarged front elevation view of an endovascular variable aortic control captive balloon device according to an embodiment of the present invention.

Referring now to FIG. 14, an EVACC 200 according to a third embodiment of the invention is shown and includes an anterograde blood flow control employing a captive balloon concept. FIG. 14 includes elements similar to those previously described in other embodiments including a central guide wire 220, a J-tip 222, a cone shaped tip 225, a wire basket 230, an occlusion barrier 240, and a delivery sheath 260. The wire basket 230 includes ribs 233 that extend proximally to form a throat 232; the occlusion barrier 240 includes a cup-like body 241, a distal perimeter 244, and an occlusion barrier neck 242 extending proximally from the cup-like body 241. The occlusion barrier neck 242 and extended throat 232 are sized to receive an inflatable balloon 250. The extended occlusion barrier neck 242 is sized to expand less than the perimeter 244 of the occlusion barrier 240. Consequently, the occlusion barrier neck 242 constrains expansion of the balloon 250 such that full expansion of the balloon 250 within the throat 232 and occlusion barrier neck 242 causes the lumen within the occlusion barrier neck 242 to be fully occluded by the balloon 250. Flow may be adjusted by deflating or inflating the balloon 250 within the occlusion barrier neck 242; this changes the available flow area.

Figure 15:
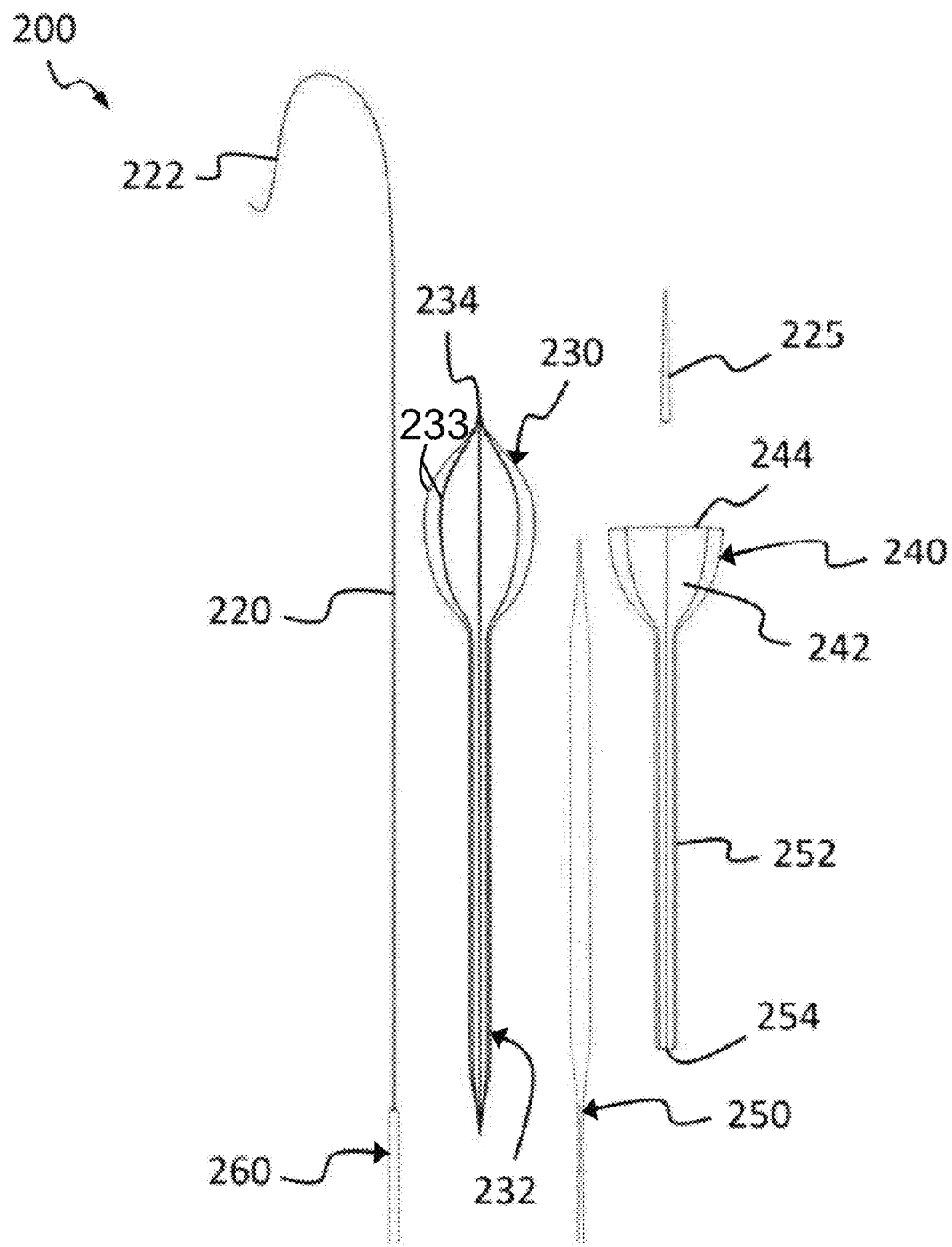
FIG. 15 is an enlarged front elevation view showing components of the device thereof.

Referring now to FIG. 15, individual components of the EVACC 200 with additional components are shown. Additional components include the endovascular guide wire 220 having J-tip 222, a tapered nose cone 225 for receiving the distal end of the wire basket 230, the extended throat 232, the occlusion barrier 240, the corresponding inflatable balloon 250, and the delivery sheath 260.

Figure 16:
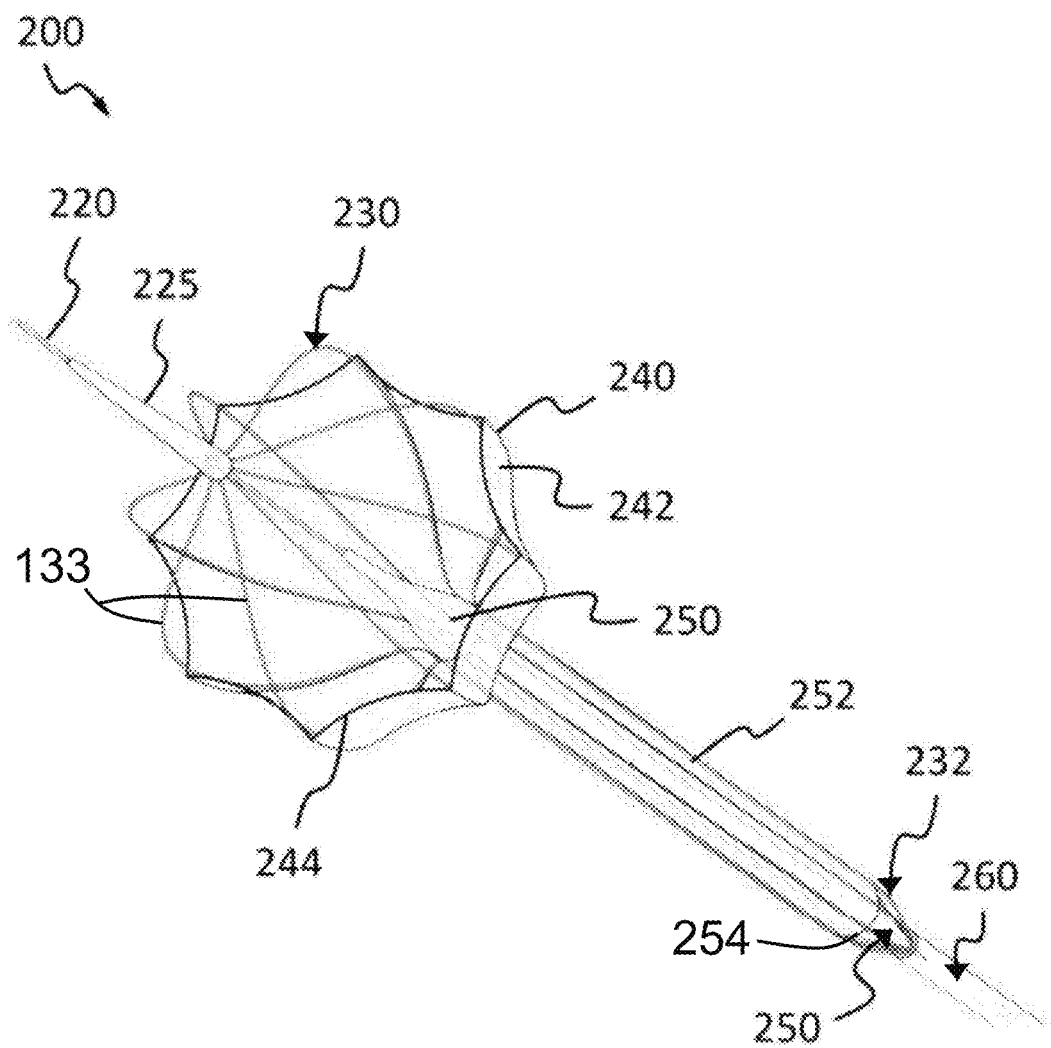
FIG. 16 is an enlarged fragmentary view thereof.

Referring now to FIG. 16, a perspective view from the distal end to proximal end of the EVACC 200 in a fully deployed state. The captive balloon 250 is fully inflated, creating full occlusion.

Figure 17:
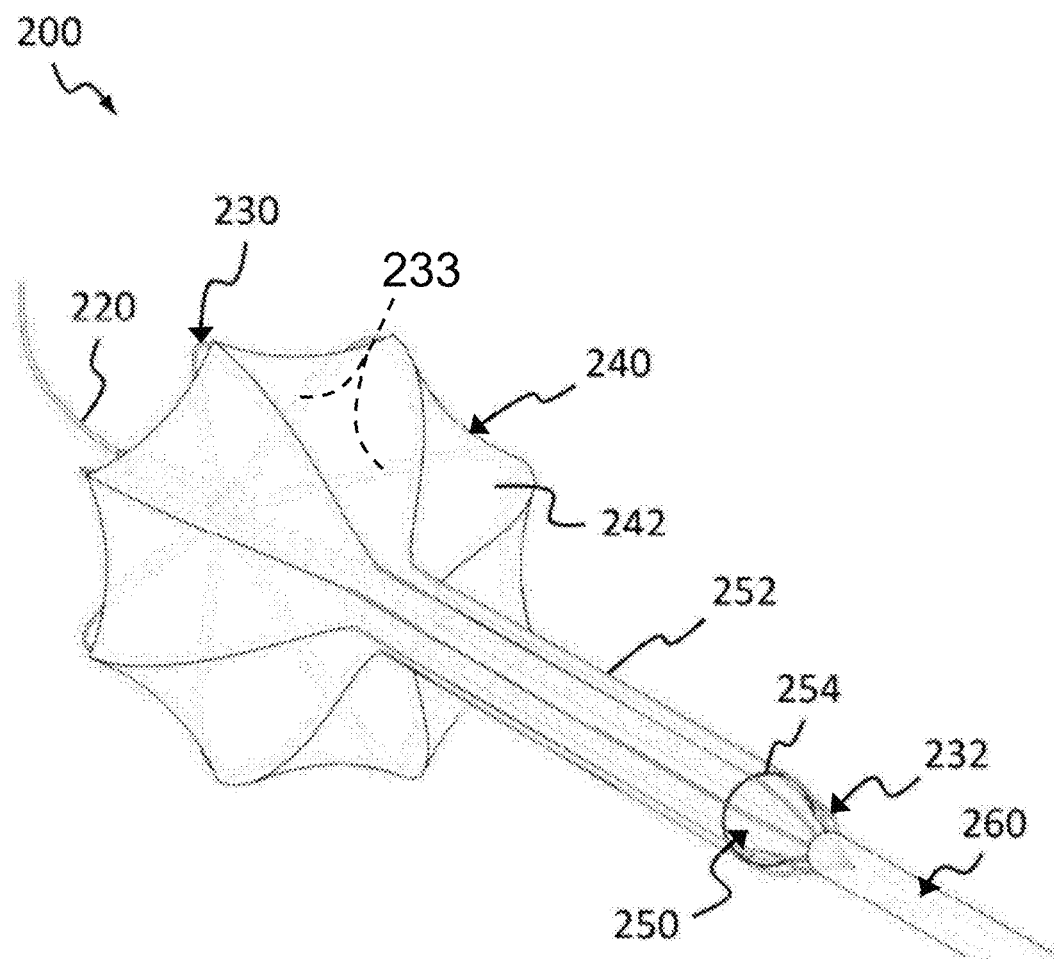
FIG. 17 is a second enlarged fragmentary view thereof.

Likewise, FIG. 17 is another perspective view of the EVACC 200 from the proximal end to the distal end of the extended occlusion barrier 240. The balloon 250 extends into the cup-like body 241 of the extended occlusion barrier 240. The balloon 250 resides within the throat 232, which resides within the extended occlusion barrier neck 252. Unlike other described embodiments, rather than adjusting flow by advancing and retracting the sheath 260, flow is adjusted by inflating or deflating the balloon 250. Hence, flow may be adjusted from a fully occluded state to a partially occluded state, and back.

Fenestrated Cone Embodiment (EVACC 300): FIGS. 18-21

Figure 18:
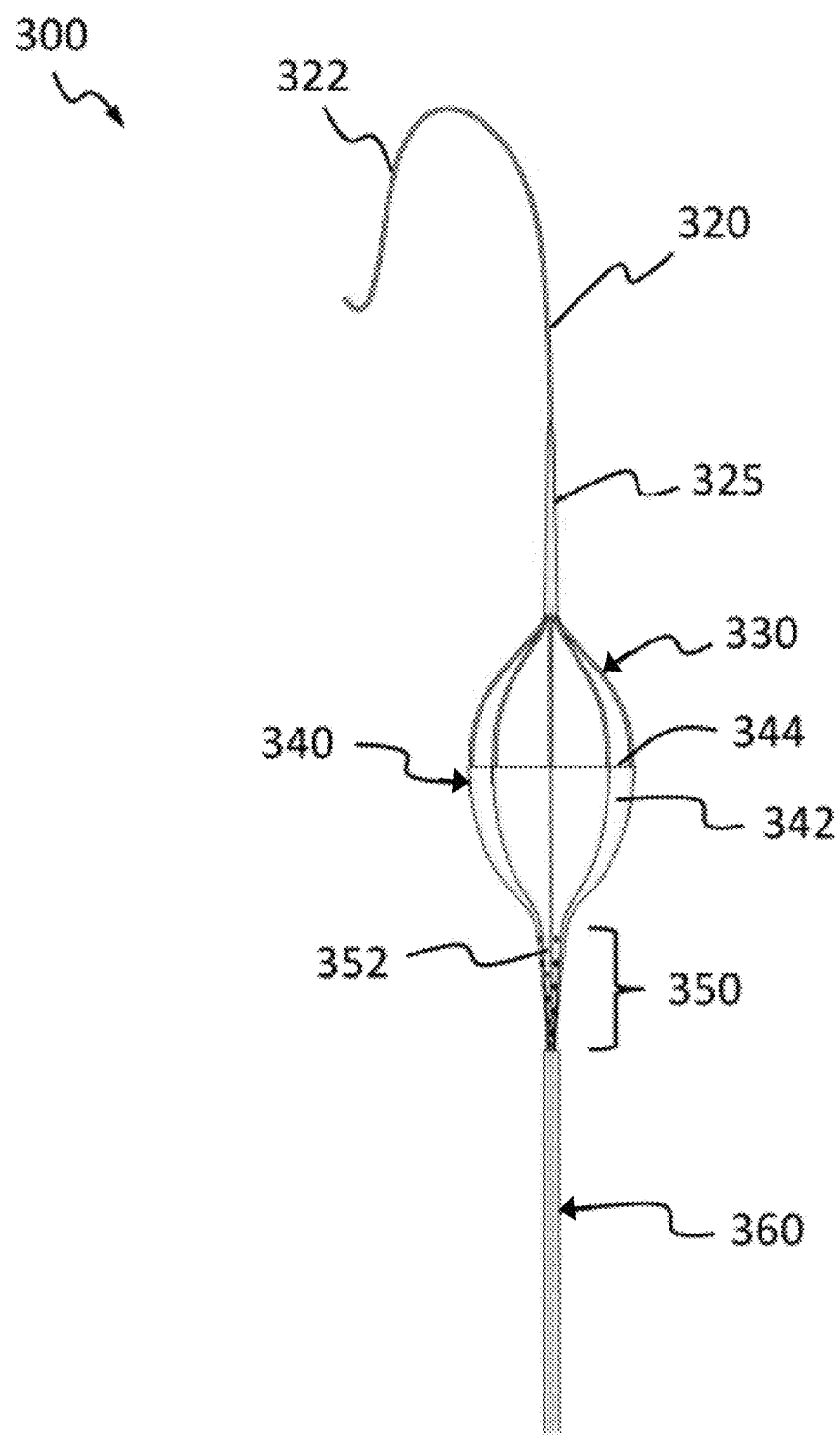
FIG. 18 is an enlarged front elevation view of an endovascular variable aortic control fenestrated cone device according to an embodiment of the present invention.

Referring now to FIG. 18, an EVACC 300 according to a fourth EVACC embodiment having anterograde blood flow controlled or regulated using a fenestrated cone concept hereinafter the EVACC 300 is shown. The EVACC 300 is substantially similar to the previously described EVACC 10 (FIG. 1) with the exception of the occlusion barrier 340, which tapers down to a conically-shaped fenestrated conduit 350, rather than a fenestrated neck 50. As with the EVACC 10 (FIG. 1), advancing or retracting of the conically-shaped fenestrated conduit 350 with respect to the delivery sheath 360 regulates flow by causing perforations 352 to be covered or exposed and the diameter of the conically-shaped portion of the fenestrated conduit 350 to be enlarged or reduced as retracted into the delivery sheath 360.

Figure 19:
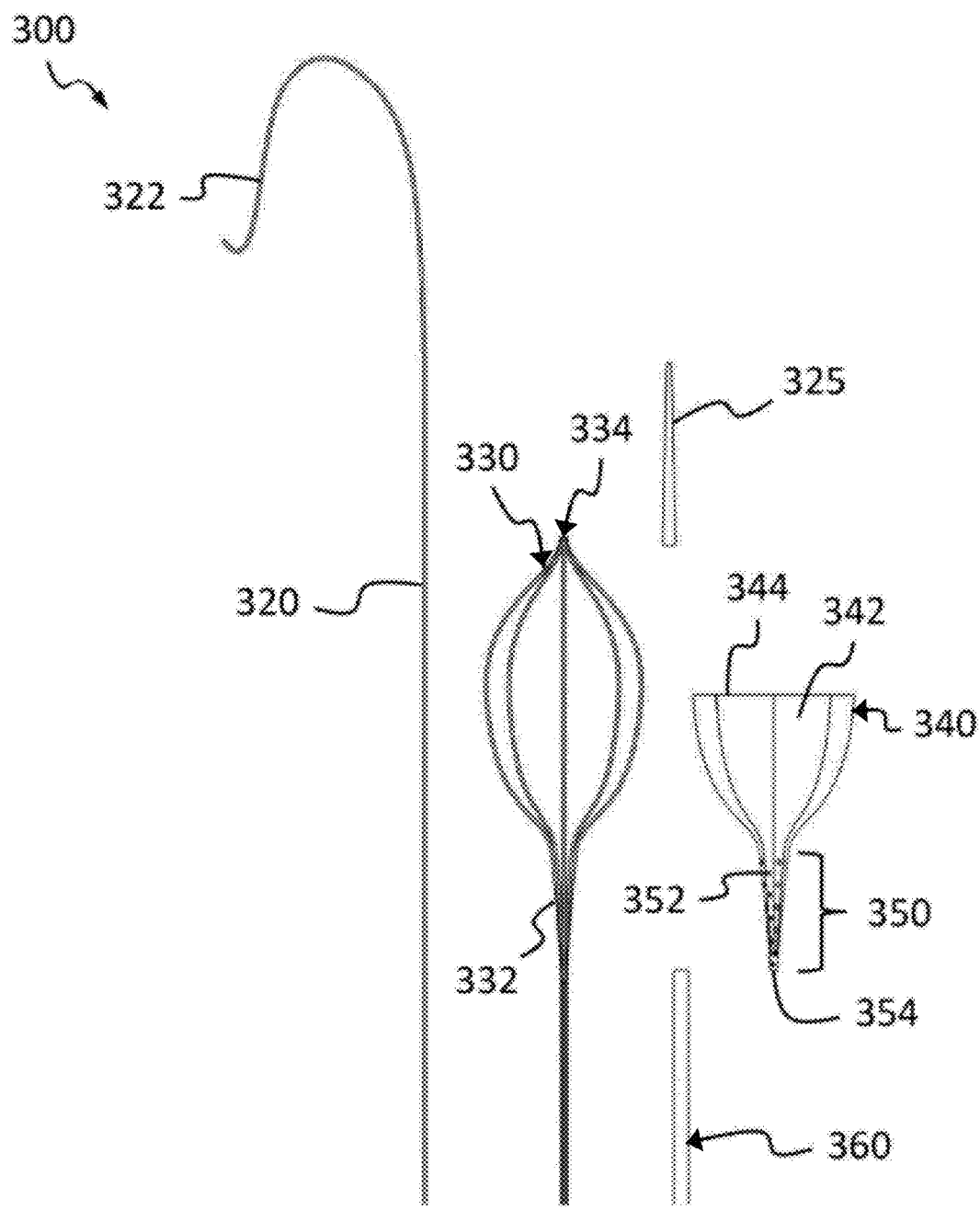
FIG. 19 is an enlarged front elevation view showing components of the device thereof.

FIG. 19 is a component view of the EVACC 300, comprising an endovascular wire 320 having a J-tip 322, a tapered nose cone 325 for receiving the distal end 334 of a wire basket 330, an occlusion barrier 340 having a conically-shaped fenestrated conduit 350 with perforations 352, and a delivery sheath 360. The occlusion barrier 340 comprises a cup-shaped body 342 having an upstream perimeter 344. The wire basket 330 includes a throat assembly 332, which expands to deploy the fenestrated conduit 350. The fenestrated conduit 350 includes a downstream end orifice 354.

Figure 20:
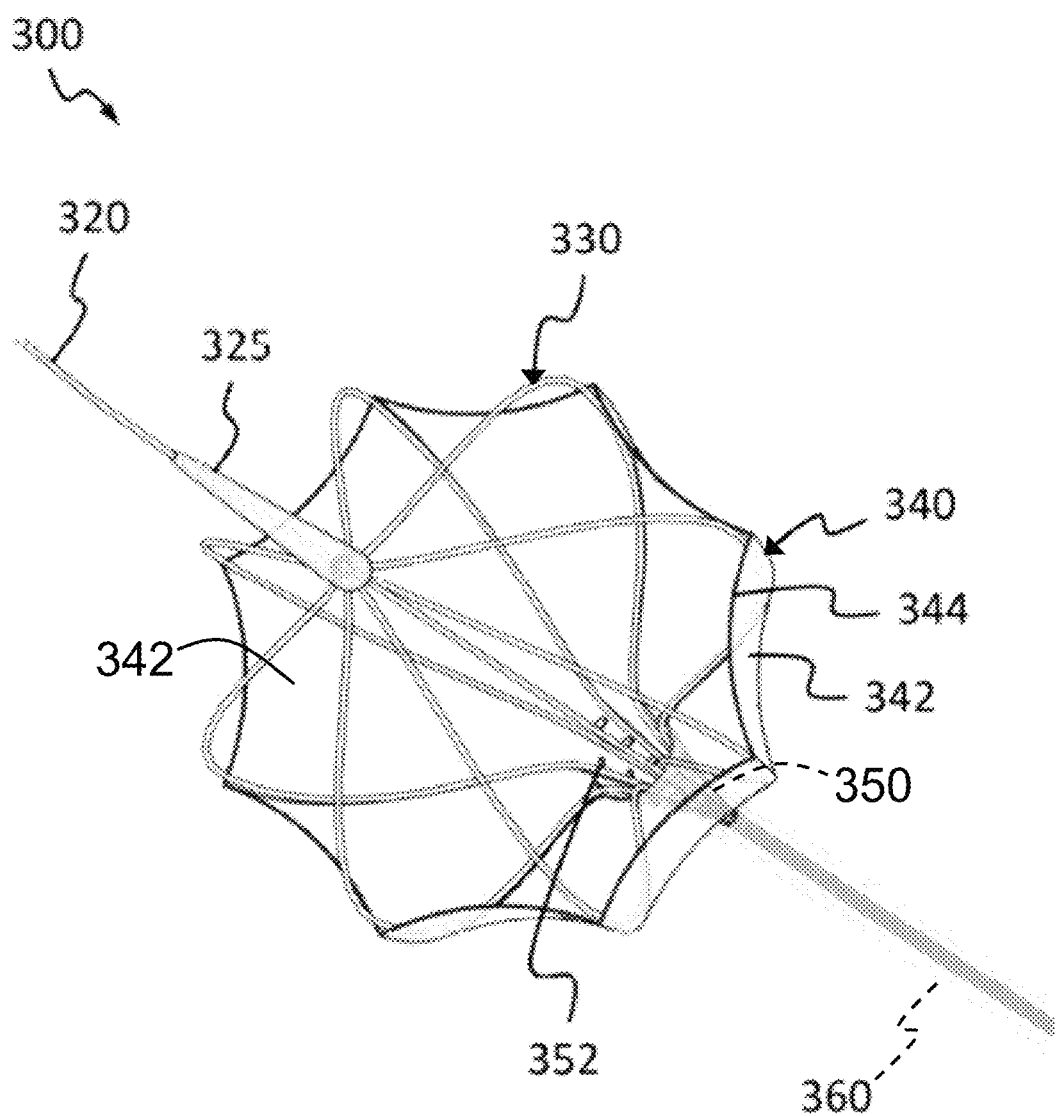
FIG. 20 is an enlarged fragmentary view thereof.

Referring now to FIG. 20, a perspective view from the distal end to the proximal end of the occlusion barrier 340 of the EVACC 300 is illustrated revealing the perforations 352.

Figure 21:
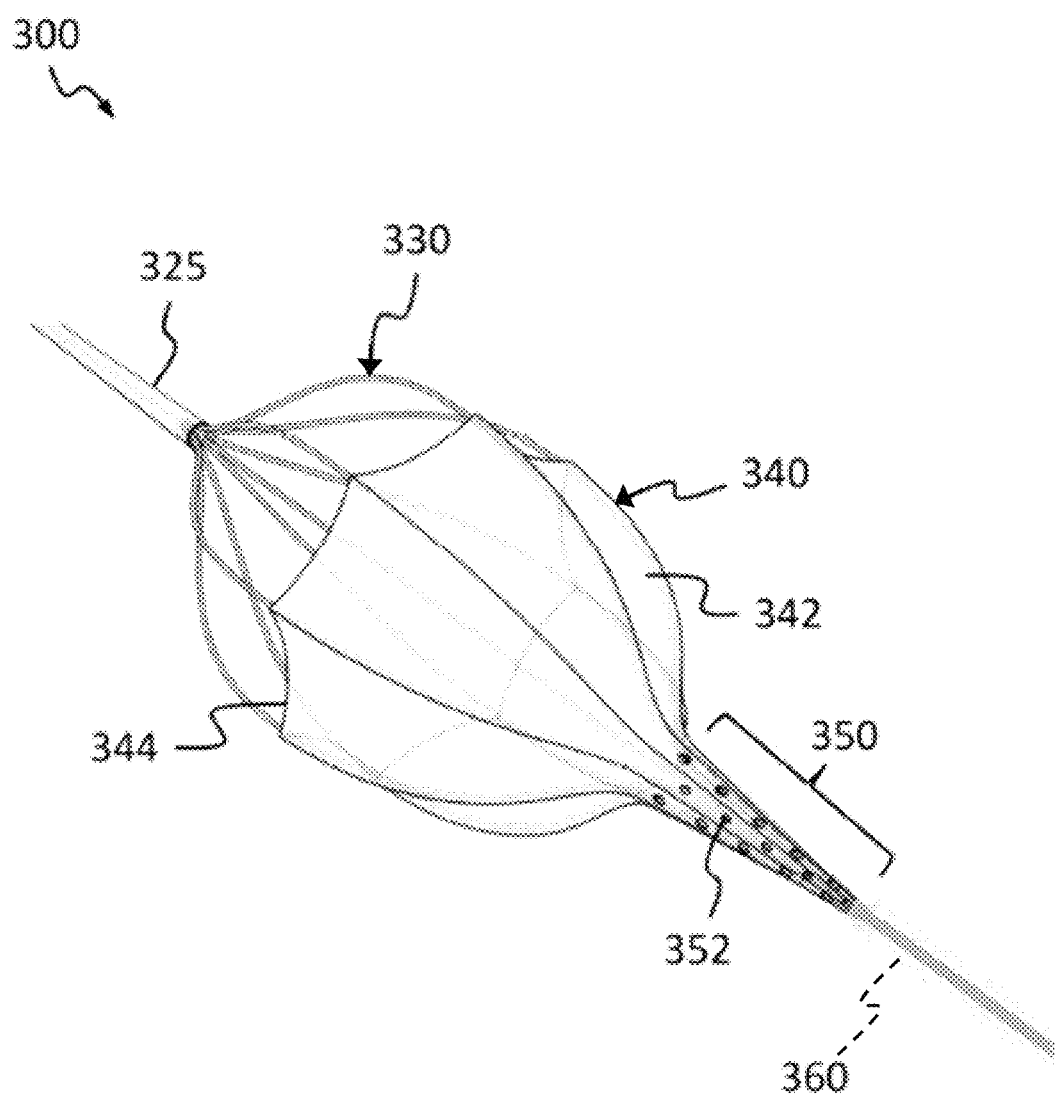
FIG. 21 is a second enlarged fragmentary view thereof.

In FIG. 21, a perspective view from the proximal end to the distal end illustrates the conically-shaped fenestrated conduit 350 and associated perforations 352. Flow is adjustable from a fully occluded state to a partially occluded state by advancing or retracting the delivery sheath 360 over the conically shaped fenestrated conduit 350.

Peripheral Internal Constriction Embodiment (EVACC 400): FIGS. 22-25

Figure 22:
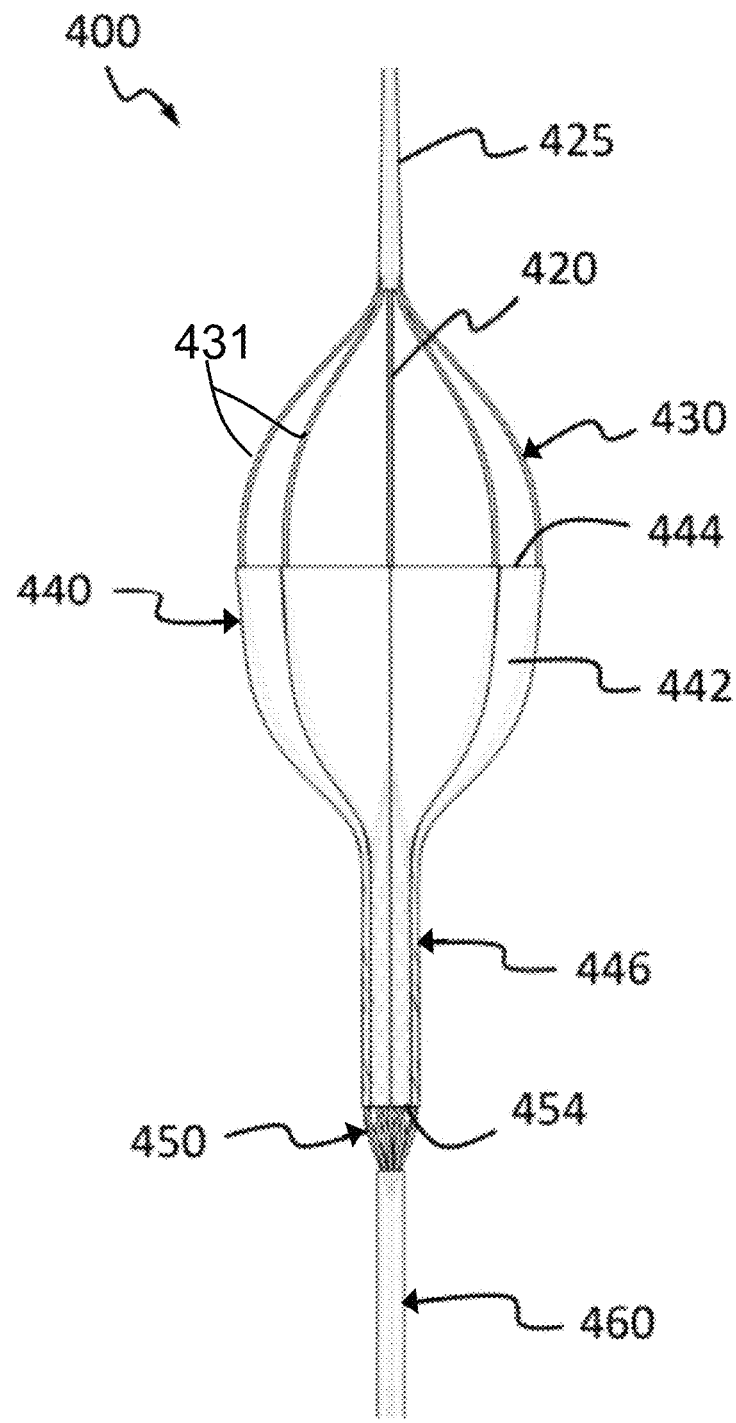
FIG. 22 is an enlarged front elevation view of an endovascular variable aortic control "finger trap" device according to an embodiment of the present invention.

Referring now to FIG. 22, a side elevation view of an EVACC 400 according to a fifth embodiment of the invention is shown, where anterograde blood flow is controlled or regulated using a peripheral internal constriction (PIC) 450. As shown, a central guide wire 420 is configured to move the EVACC 400 through the vascular to a targeted location. A distal tapered nose cone 425 is slidably received onto the central guide wire 420. At its base, the nose cone 425 is sized to receive a distal end 434 of the wire basket 430, where each support wire 431 converges to form a tip at the distal end 434. The wire basket 430 is partially enveloped by an occlusion barrier 440 made of appropriate collapsible and expandable material, such as ePTFE, polyester or other material having similar characteristics. Upon deployment within an artery, the wire basket 430 and the occlusion barrier 440 expand to create a cup-shaped body 442. The cup-shaped body 442 expands to appose the inner arterial wall. The occlusion barrier 440 includes an upper perimeter 444 and an extended neck 446. The PIC 450, which is a wire mesh 451 comprising a cylindrical, helically-wound braid, is positioned within the lumen of the extended neck 446 and the extended neck 446 and PIC 450 are joined to each other. The extended neck 446 includes a downstream orifice 454 that is deployed out the end of the delivery sheath 460 to allow flow when the occlusion barrier 440 is deployed and the extended neck 446 open.

Figure 23:
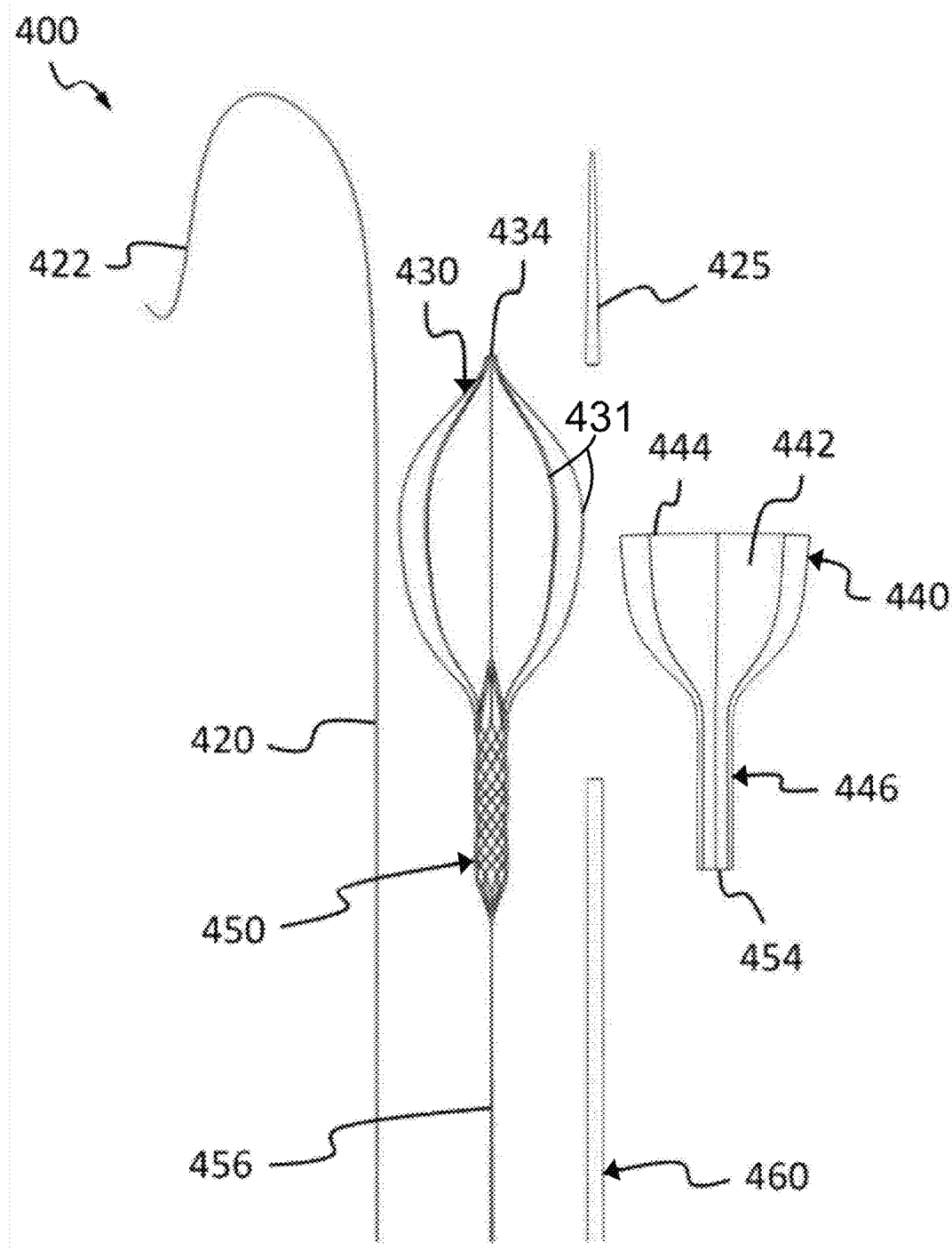
FIG. 23 is an enlarged front elevation view showing components of the device thereof.

Referring now to FIG. 23, the individual components of the EVACC 400 are illustrated and described in greater detail. The notable difference includes the PIC 450 and the extended neck 446 of the occlusion barrier 440. In use, the PIC 450 is lengthened to reduce an inner diameter or shortened to increase the inner diameter. In one aspect, the extended neck 446 may be constructed of ePTFE, polyester, or other appropriate material having sufficient elasticity to accommodate the manipulation of the PIC 450 from a closed state to an open state.

Figure 24:
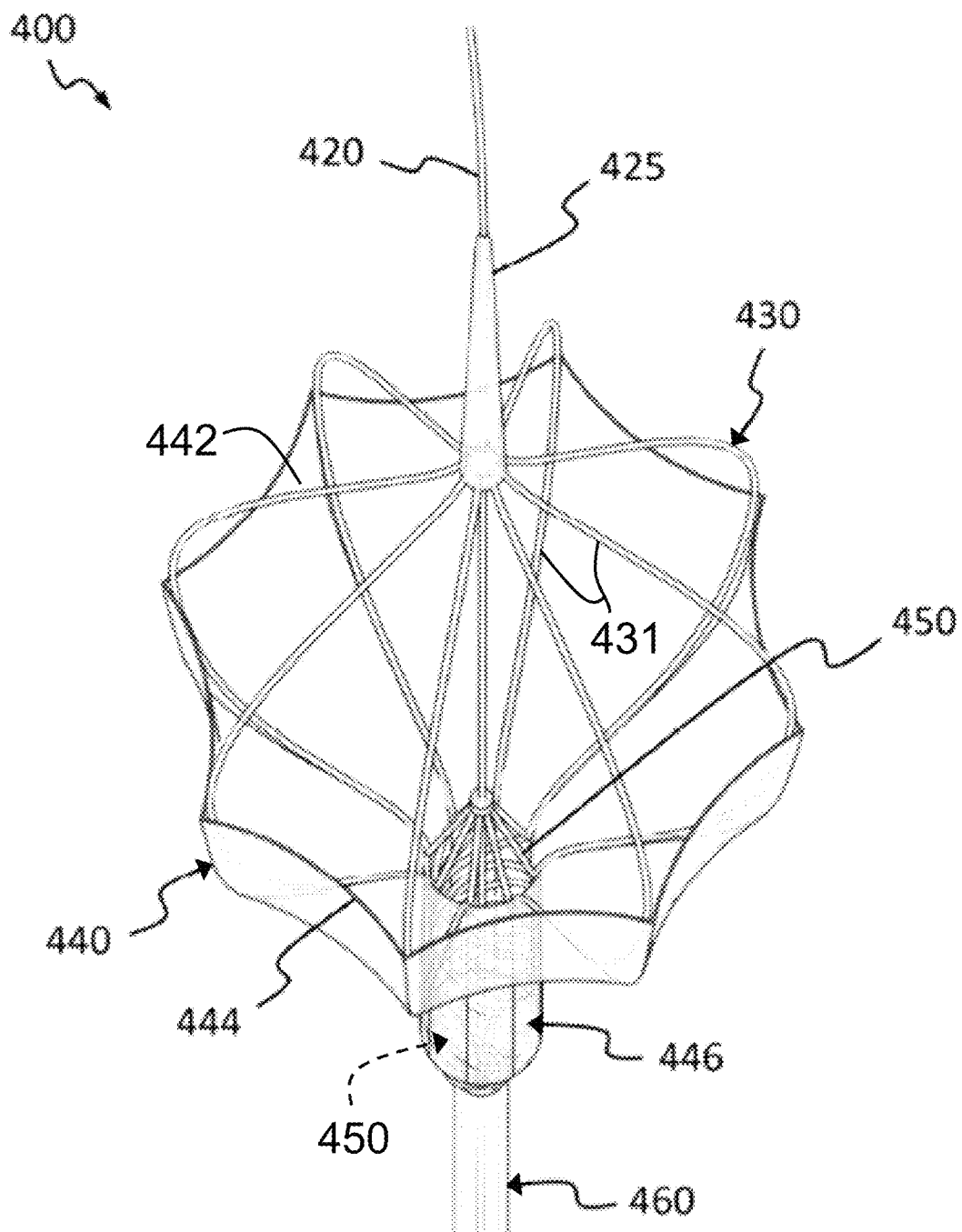
FIG. 24 is an enlarged fragmentary view thereof.

Referring now to FIG. 24, a perspective view from the distal end to the proximal end of occlusion barrier 440 of the EVACC 400 is provided. The PIC 450 is deployed within the lumen of the extended neck 446 of the occlusion barrier 440. The wire basket 430 expands to deploy the occlusion barrier 440, creating the cup-like body 442 and extended neck 446. The perimeter 444 of the occlusion barrier 440 apposes and conforms to the shape of the interior of the blood vessel, thereby funneling flow into the extended neck 446 and through the proximal orifice 454. The distal end 434 of the wire basket 430 is captured within the conical tip 425.

Figure 25:
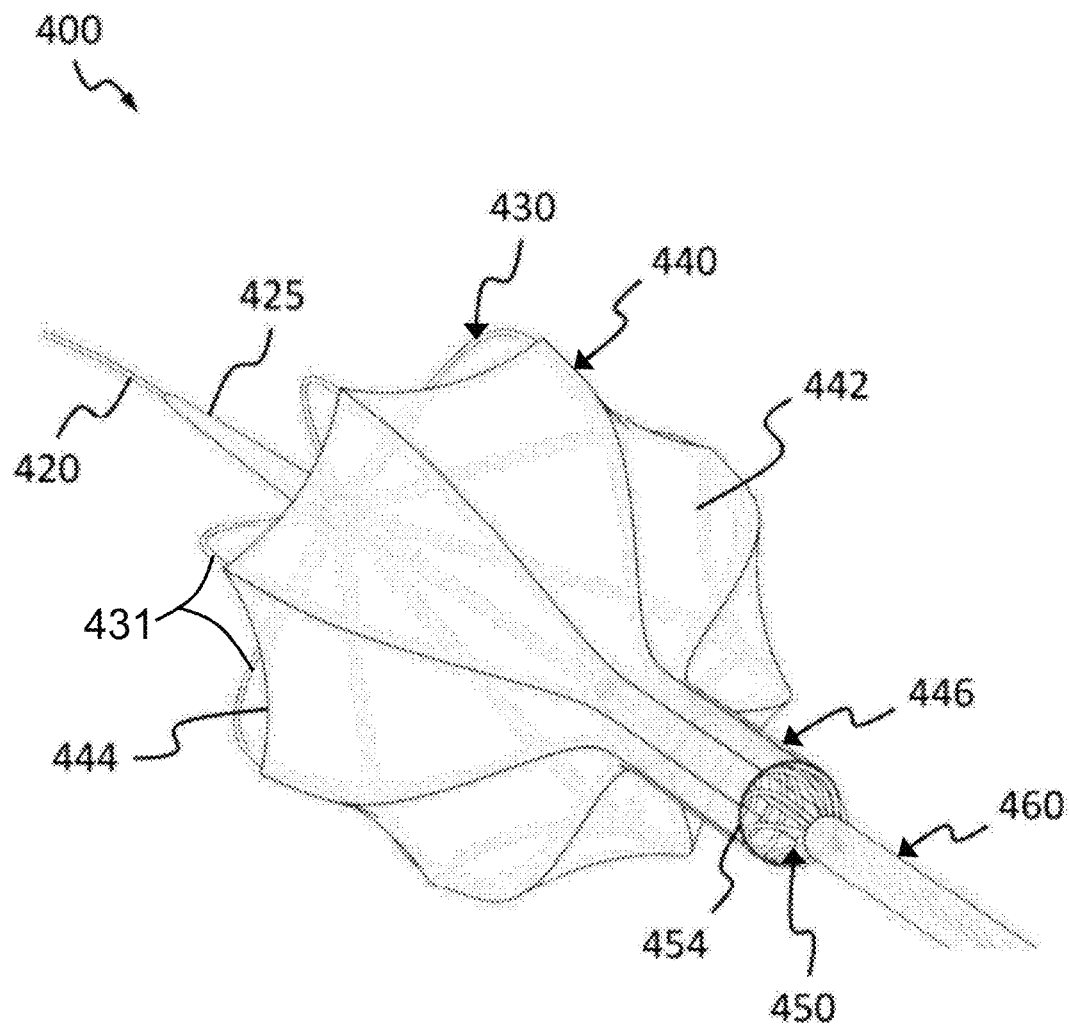
FIG. 25 is a second enlarged fragmentary view thereof.

Turning now to FIG. 25, a perspective view from the proximal end to the distal end of the EVACC 400 in a fully deployed state is provided. Flow control is achieved by the PIC 450 in conjunction with the extended neck 446 and the occlusion barrier orifice 454.

In a fully deployed state, the EVACC 400 is actuated by the retraction or extension of an inner pull wire 456 that causes the PIC 450 to dilate or contract its diameter. The diameter of the proximal orifice 454 will increase or decrease in size as well, in correlation to the lengthening or shortening of the PIC 450. The individual wires 431 of the PIC 430 are threaded together, wherein extending the PIC 430 causes individual wires 431 to rotate and mesh more closely together, thereby increasing resistance to flow caused by the restriction within the extended neck 446. Thus, upstream and downstream blood pressure and flow through the EVACC 400 may be adjusted and controlled. The material used to form the extended neck 446 will have sufficient elasticity to stretch and narrow in correlation with the PIC 450.

Lasso Aperture Embodiment (EVACC 500): FIGS. 26-29

Figure 26:
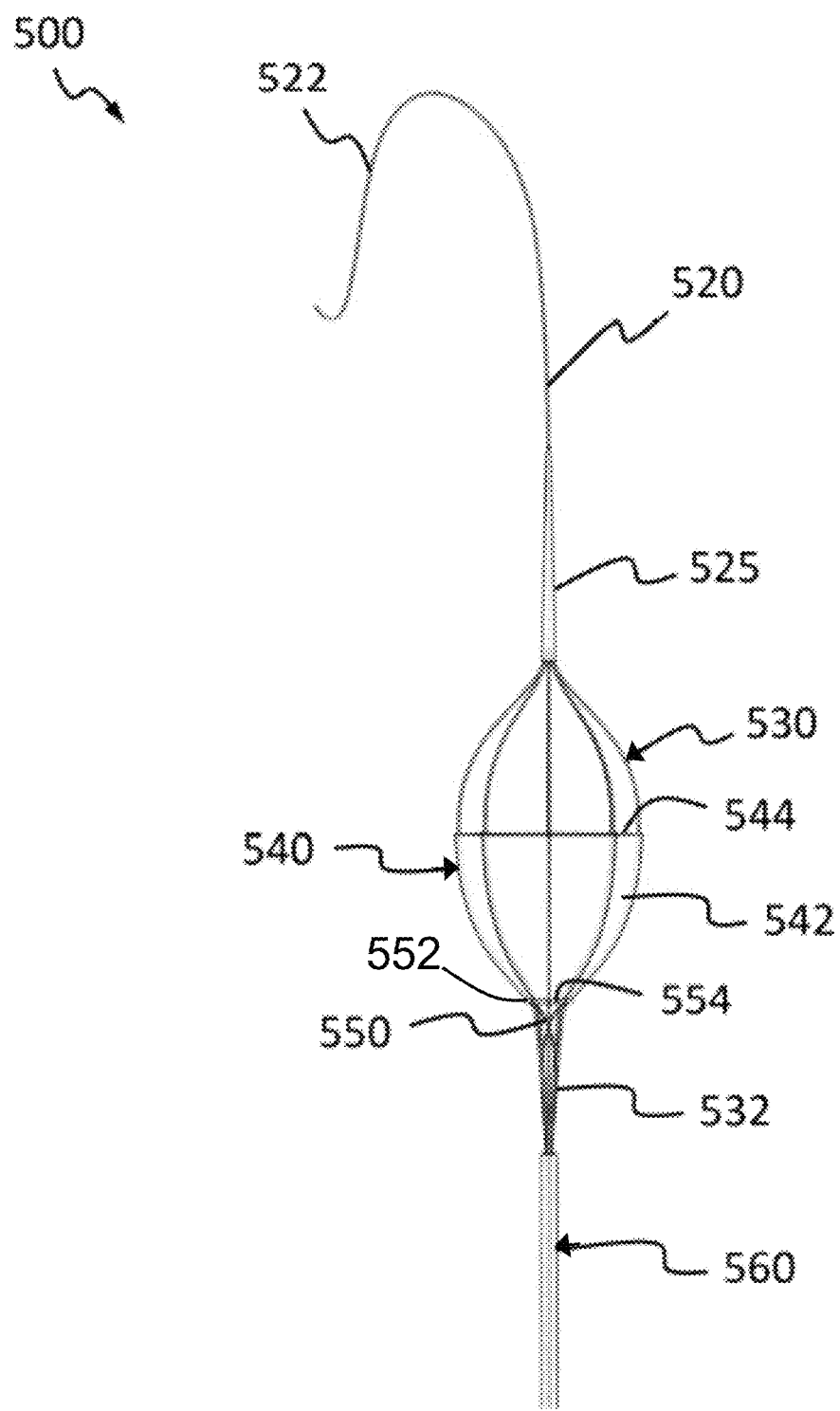
FIG. 26 is an enlarged front elevation view of an endovascular variable aortic control lasso device according to an embodiment of the present invention.

Referring now to FIG. 26, in an EVACC 500 according to a sixth embodiment of the invention having anterograde blood flow controlled or regulated using a lasso wire 550 is shown. A wire basket 530 narrows to a throat 532 that may be variably occluded by the retraction of wires 550 configured to narrow the aperture 554 when tension is placed on the lasso wires 550. The EVACC further includes a central guide wire 520 having a J-tip 522 for guiding the EVACC 500 to a target location within a patient's vasculature. A distal end 534 of the wire basket 530 is captured within a tapered cone 525. The wire basket 530, which may be constructed using shape memory materials, is enveloped by and bonded to an occlusion barrier 540 forming an expandable and collapsible cup-like body 542. The occlusion barrier 540 may be made of ePTFE, polyester or other similar material. The cup-like body 542, when deployed, includes a perimeter 544, which will appose the interior wall of the blood vessel, and a proximal orifice 554 through which flow will be diverted when in an open state. A lasso wire 550 is slidably joined with the proximal orifice 554. Manipulation of the lasso wire 550 causes the proximal orifice 554 to either increase or decrease in diameter, thereby regulating flow through the proximal orifice 554 and establishing a pressure differential across the proximal orifice 554. The occlusion barrier 540 and wire basket 530 is delivered to a specific location in the vascular by the delivery sheath 560.

Figure 27:
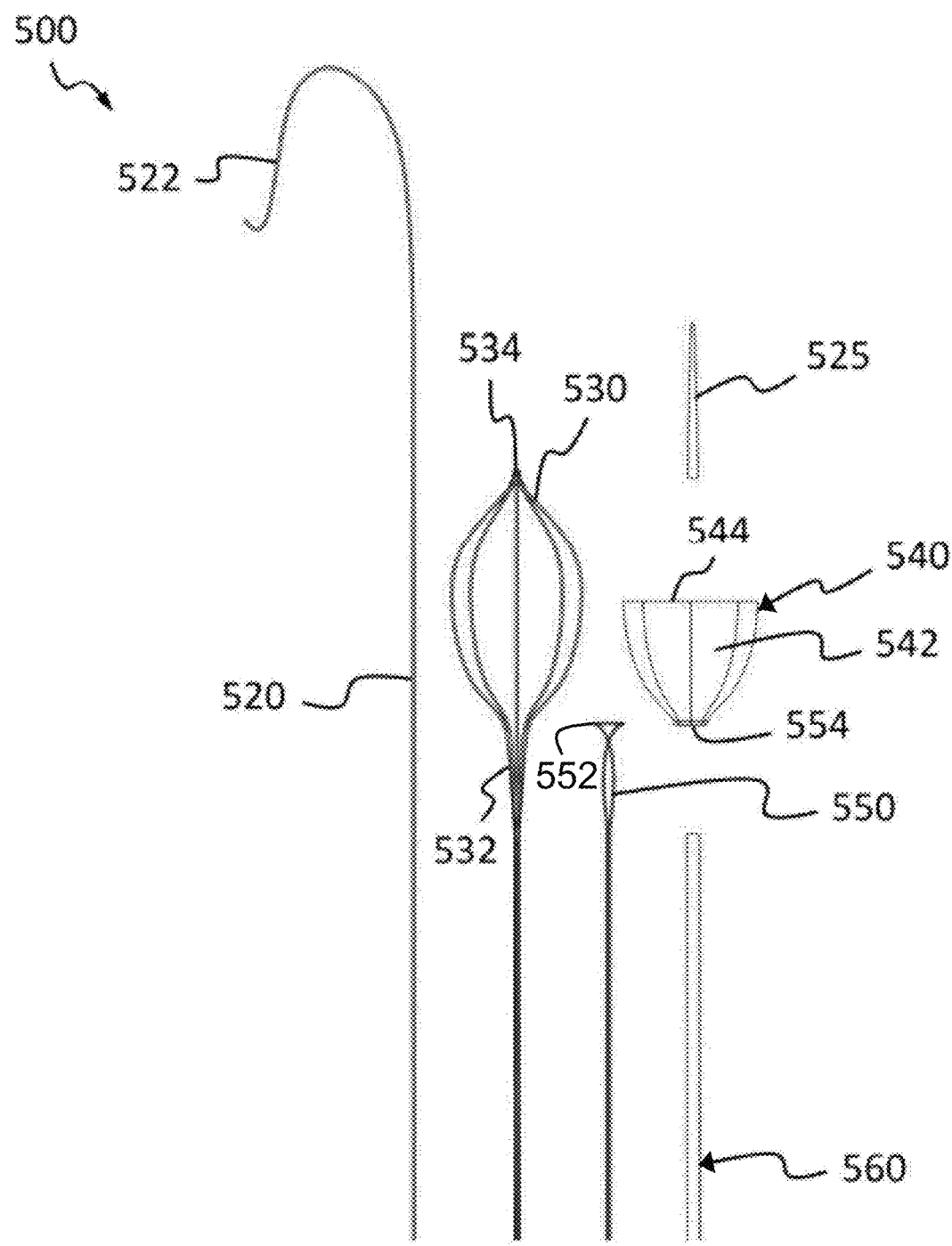
FIG. 27 is an enlarged front elevation view showing components of the device thereof.

Referring now to FIG. 27, an enlarged exploded front elevation view of the individual distal components of the EVACC 500 is provided. The EVACC 500 comprises an endovascular guide wire 520 having a J-tip 522, a tapered nose cone 525 for receiving a distal end 534 of the wire basket 530, a lasso wire 550, an occlusion barrier 540 deployed to form a cup-like body 542 having a perimeter 544 and a downstream orifice 554. A delivery sheath 560 facilitates the ease of advancing the occlusion barrier 540 to a targeted location.

Figure 28:
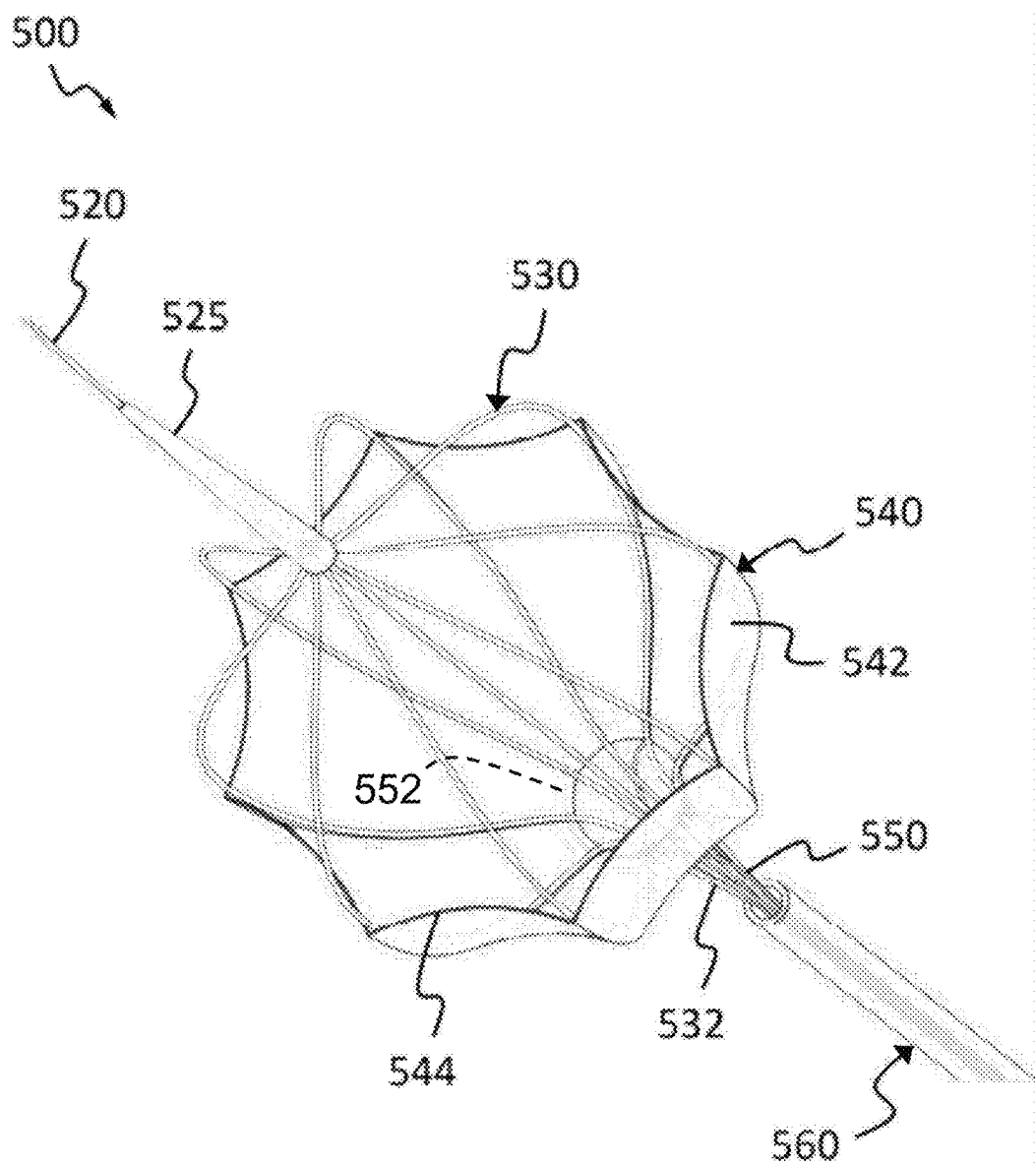
FIG. 28 is an enlarged fragmentary view thereof.

Referring now to FIG. 28, a perspective view from the distal end to the proximal end into the interior of the cup 542 of the EVACC 500 is provided. A lasso wire 550 extends to and is slidably bonded within a rim 552 of the proximal aperture 554. The throat 532 of the EVACC 500 blossoms through the aperture 554 and continues to form the wire basket 530.

Figure 29A:
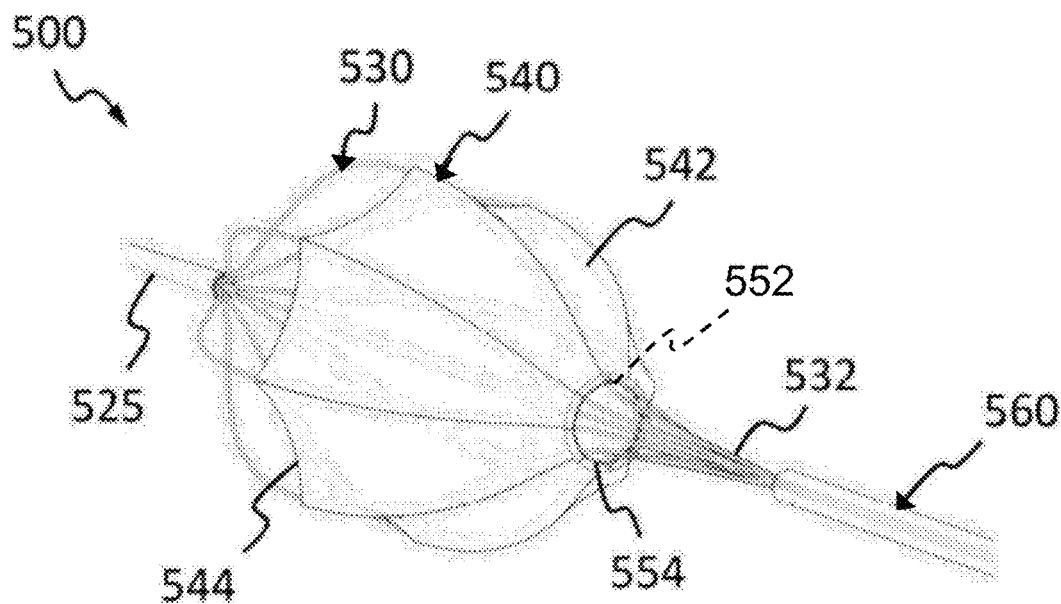
FIG. 29A is a second enlarged fragmentary view thereof.

Referring now to FIG. 29A, a perspective view from the proximal end to the distal end of the EVACC 500 emphasizes the proximal aperture 554 of the occlusion barrier 540 in a fully deployed state, extended out of the delivery sheath 560.

Figure 29B:
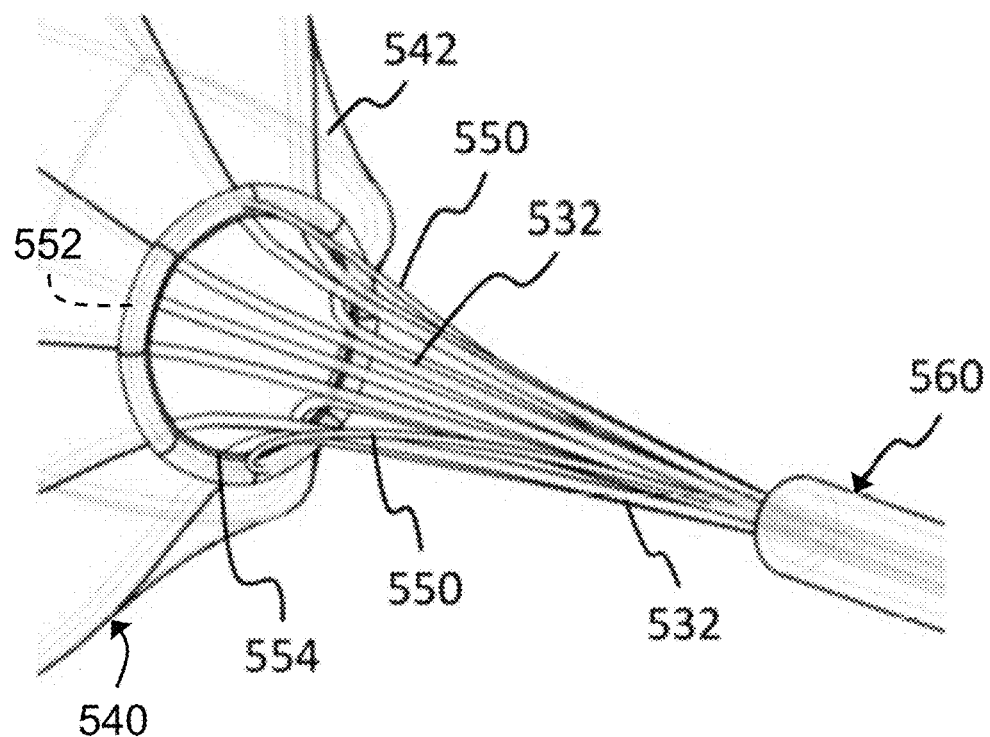
FIG. 29B is a third enlarged fragmentary view thereof.

Referring now to FIG. 29B, an enlarged view of the occlusion barrier 540 of the EVACC 500 in a fully deployed state is shown in greater detail. The cup-like body 542 includes an aperture 554 at a downstream end. The throat 532 expands to fully deploy and open the proximal aperture 554 to allow flow. The lasso wires 550 extended into the aperture 554 such that retraction of the wires 550 cause the aperture 554 to be cinched down to a smaller size, thereby reducing flow through the proximal aperture 554.

Rotating Cups Embodiment (EVACC 600): FIGS. 30-34B

Figure 30:
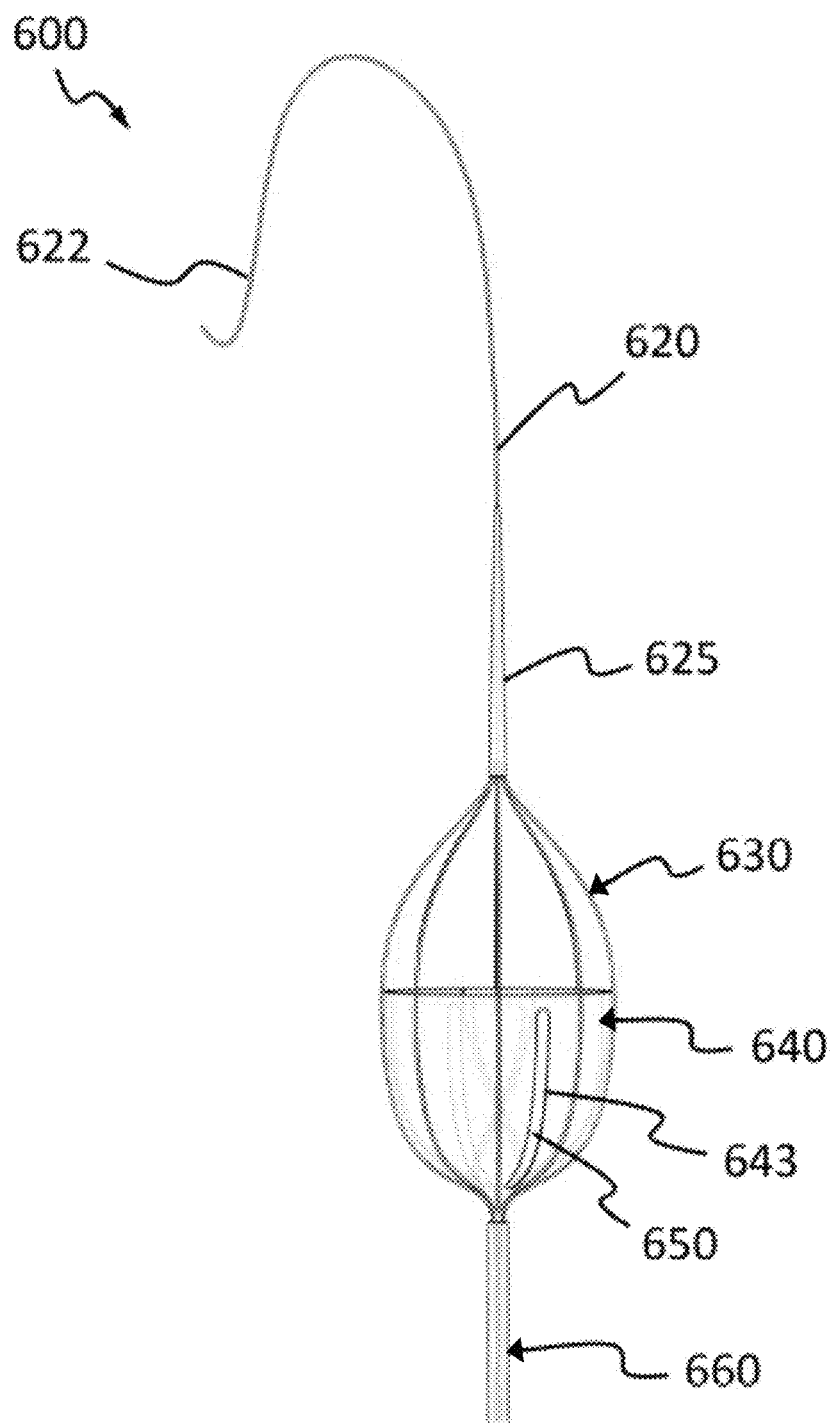
FIG. 30 is an enlarged front elevation view of an endovascular variable aortic control rotating cups device according to an embodiment of the present invention.
Figure 31:
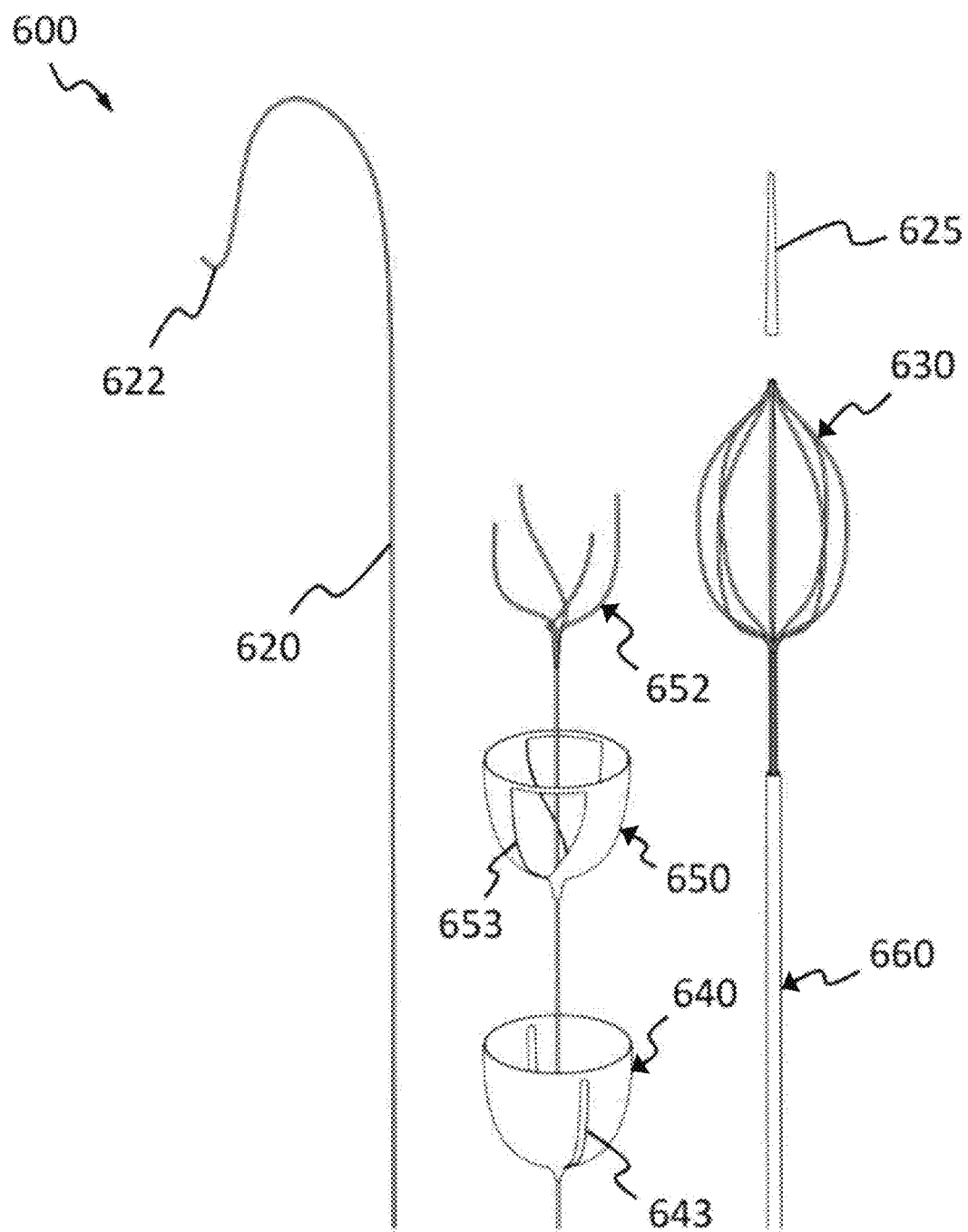
FIG. 31 is an enlarged front elevation view showing components of the device thereof.

Referring now to FIG. 30, in an EVACC 600 according to a sixth alternative embodiment of the invention, where anterograde blood flow is controlled or regulated using a rotating mated cups concept. The EVACC 600 comprises two mating cup-shaped membranes 640, 650 supported by a dual wire basket 630, 652. The first membrane 640 is supported by and bonded to first wire basket 630. The second membrane 640 includes a first set of openings 643 (e.g., two slots) that serve as passageways to allow blood flow when uncovered. The second membrane 650 is supported by and bonded to a separate (second) wire basket 652. The first membrane 650, which includes a second set of openings 653 (e.g., two slots), is rotatable to cover the first set of slots 643 to varying degrees so as to increase or restrict blood flow downstream of the occlusion barrier 640. When the first and second sets of openings 643, 653 coincide flow through the occlusion barrier 640 occurs.

Figure 32A:
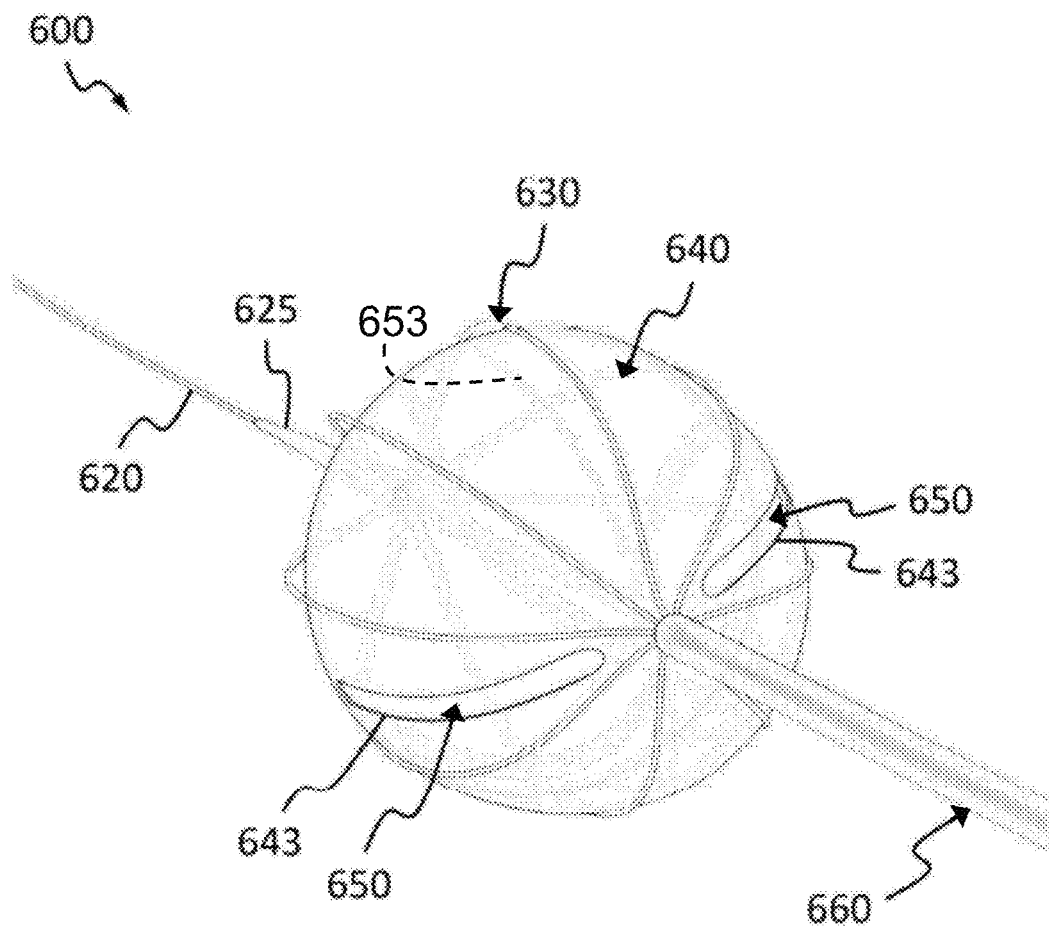
FIG. 32A is an enlarged fragmentary view of the endovascular variable aortic control rotating cups device of FIG. 30 in a closed position.
Figure 32B:
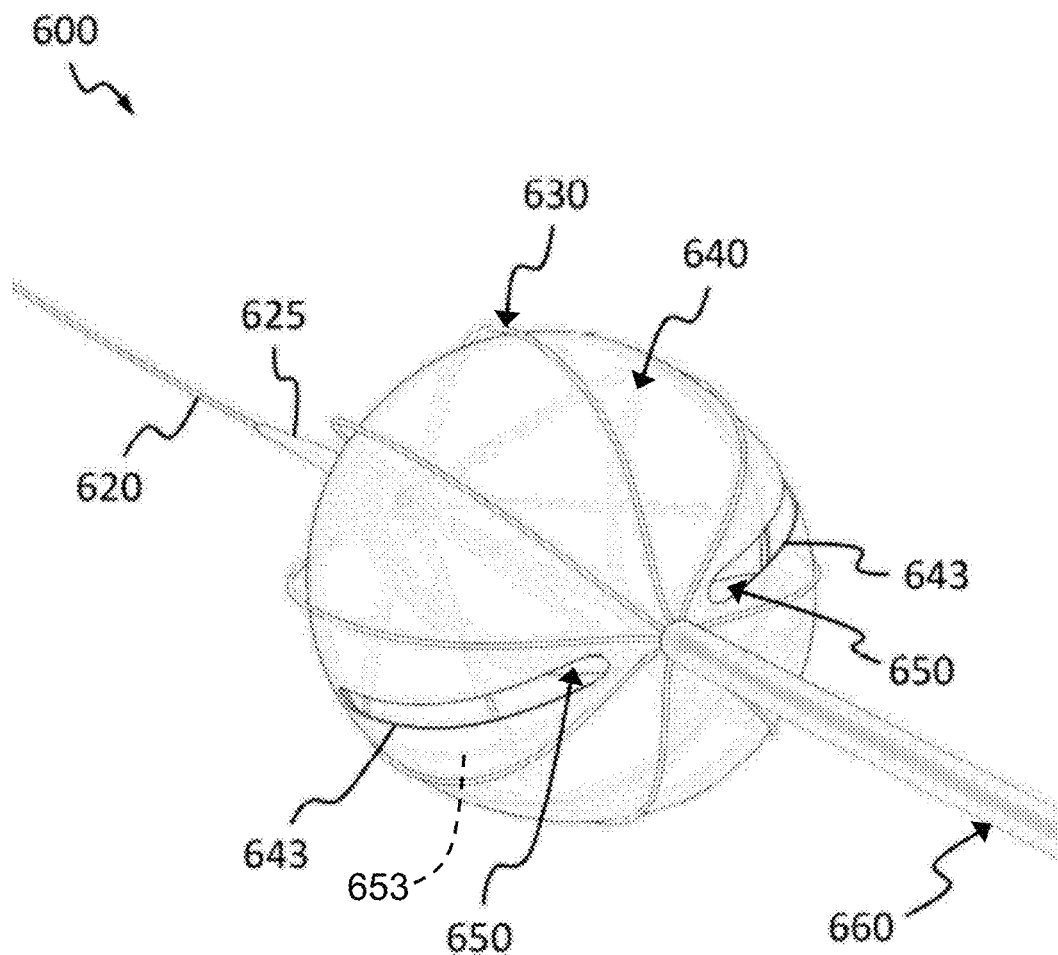
FIG. 32B is the enlarged fragmentary view of the endovascular variable aortic control rotating cups device of FIG. 32A in an open position.
Figure 33A:
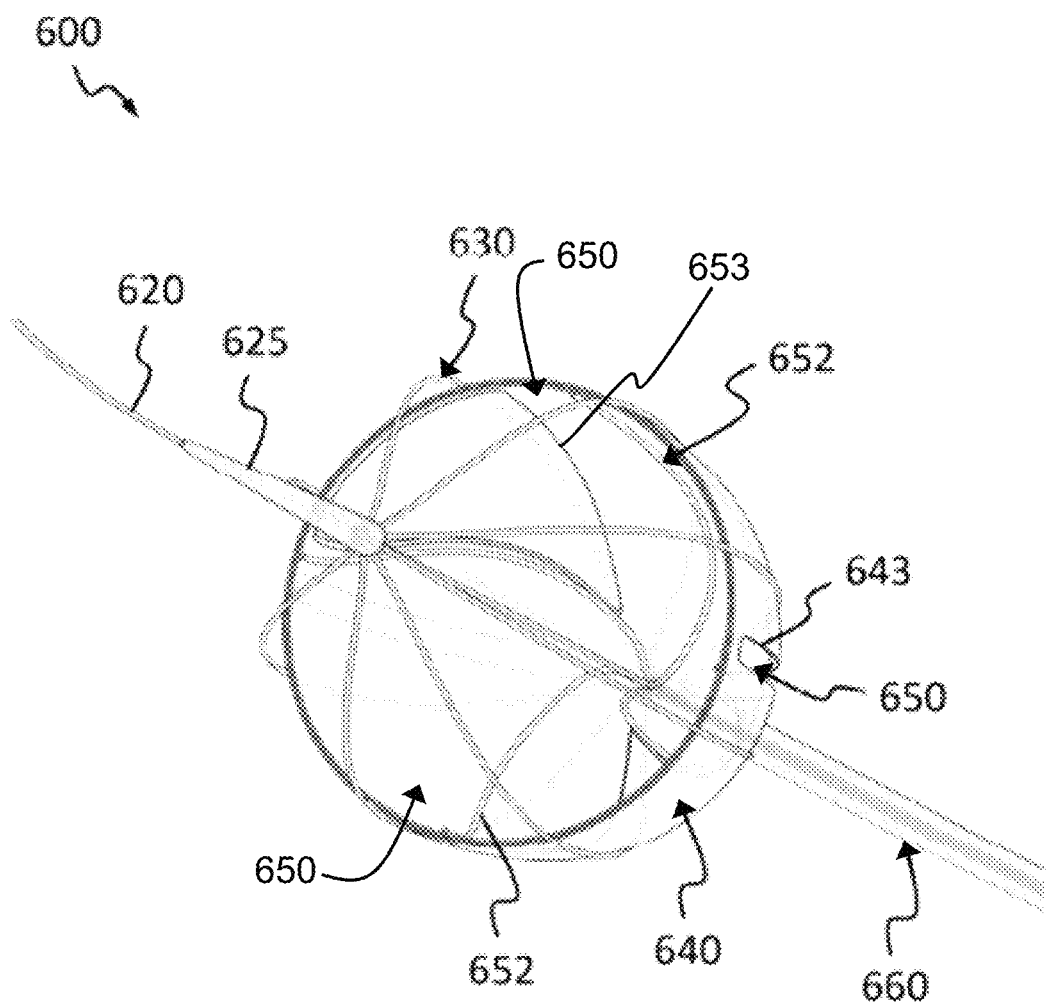
FIG. 33A is a second enlarged fragmentary view of the endovascular variable aortic control rotating cups device of FIG. 30 in a closed position.
Figure 33B:
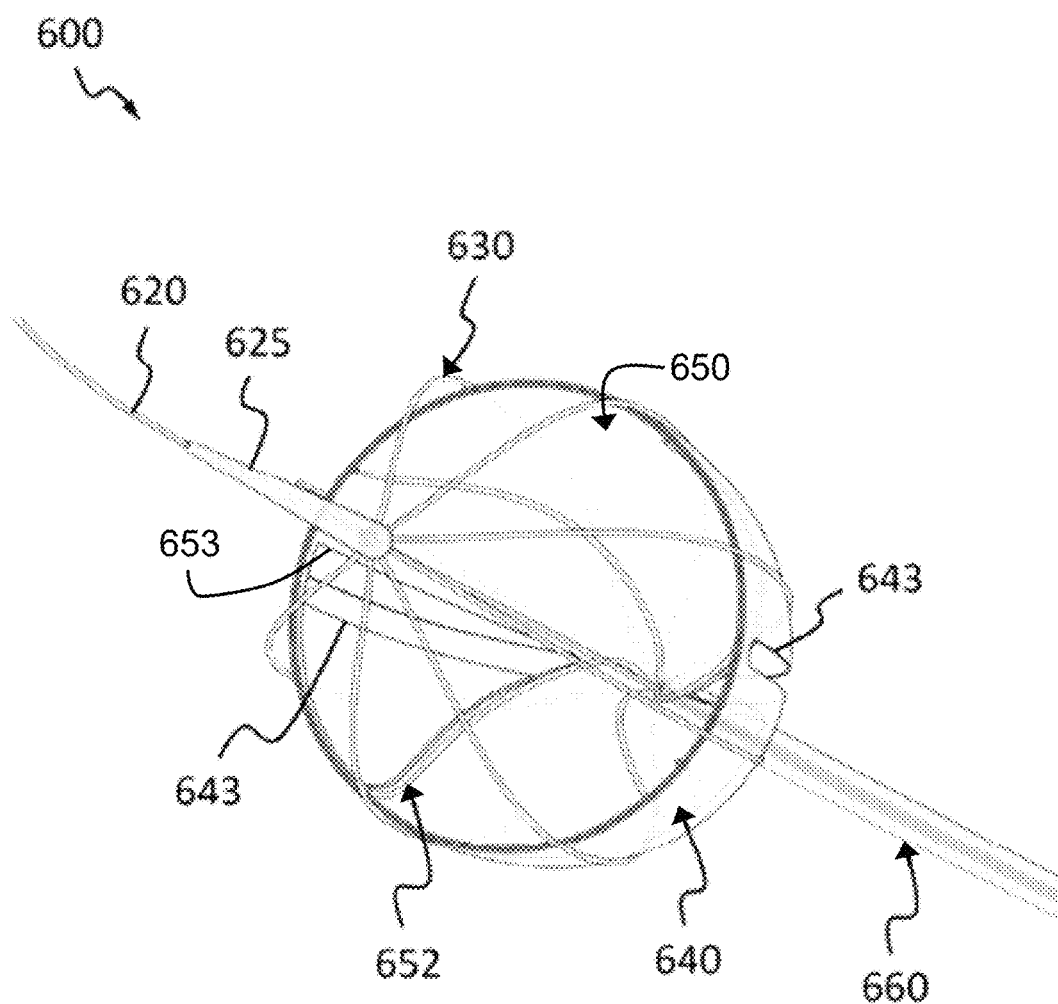
FIG. 33B is the second enlarged fragmentary view of the endovascular variable aortic control rotating cups device of FIG. 32A in an open position.

Referring now to FIG. 32A, an enlarged perspective view from the proximal end of the distal end of the EVACC 600 fully deployed out the delivery sheath 660 illustrates the arrangement of the first wire basket 630 enveloping the first membrane 640. In this state, the first set of openings 643 are covered by the second membrane 650. FIG. 32B is the same view but with the second membrane 650 having been rotated such that the first set of openings 643 are uncovered to allow anterograde flow through the first set of openings 643 and to the downstream vasculature. FIG. 33A is equivalent to FIG. 32A in a closed state, but a perspective view from the distal end to the proximal end; FIG. 33B is equivalent to FIG. 32B in an open state but a perspective view from the distal end to the proximal end.

Figure 34A:
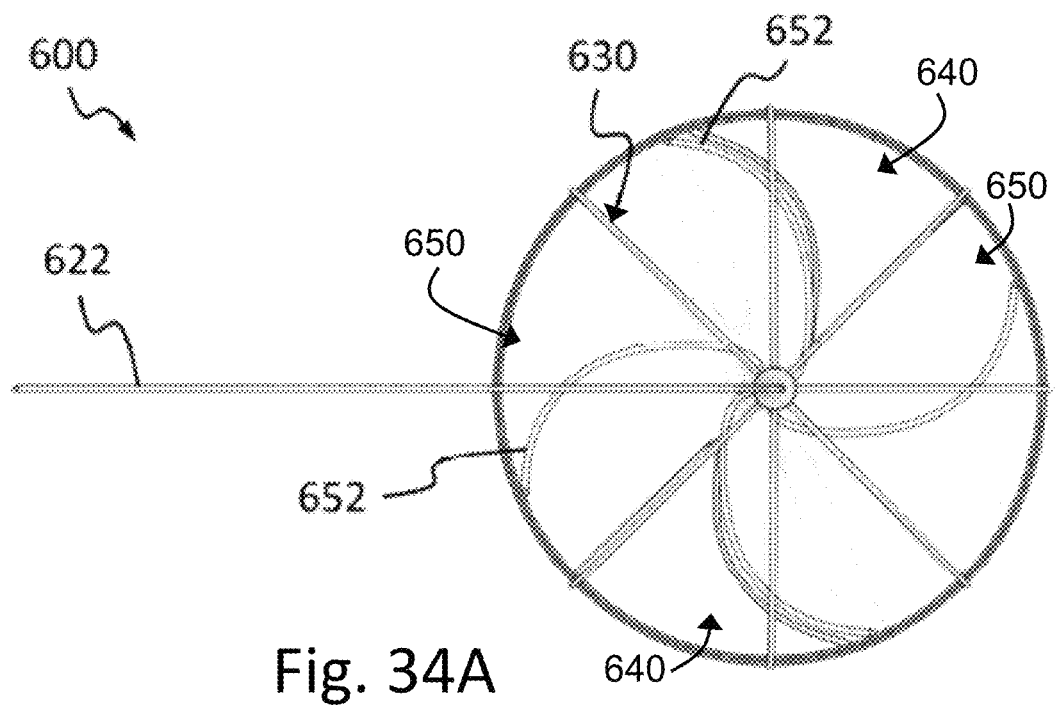
FIG. 34A is a top plan view of the endovascular variable aortic control rotating cups device of FIG. 30 in a closed position.
Figure 34B:
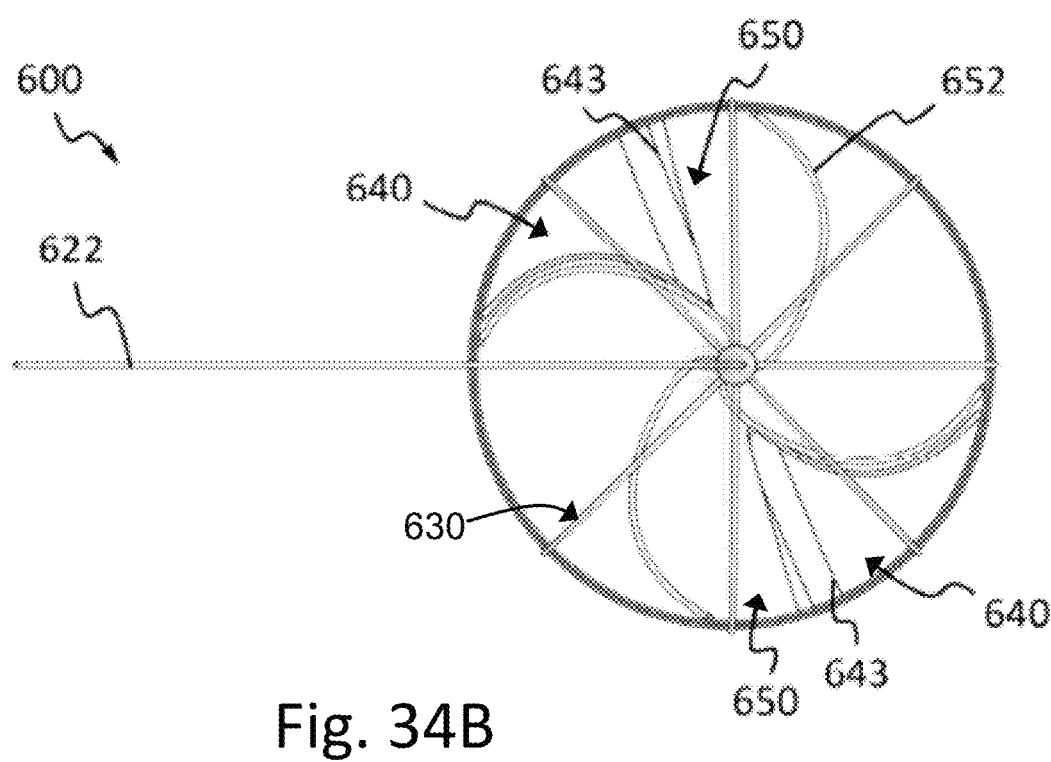
FIG. 34B is a top plan view of the endovascular variable aortic control rotating cups device of FIG. 30 in an open position.

Referring now to FIG. 34A and FIG. 34B, a top plan view of the EVACC 600 emphasizes the mating of the first and second sets of openings 643, 653 of the first and second membranes 640, 650, respectively, and illustrates the J-tip 622. FIG. 34A shows the EVACC 600 in a fully closed state, whereby the flow is fully restricted. FIG. 34B shows the EVACC 600 in an open state, whereby the second membrane 650 is in a rotated position such that the first set of openings 643 of the first membrane 640 are fully uncovered, allowing maximum blood flow.

Figure 35A:
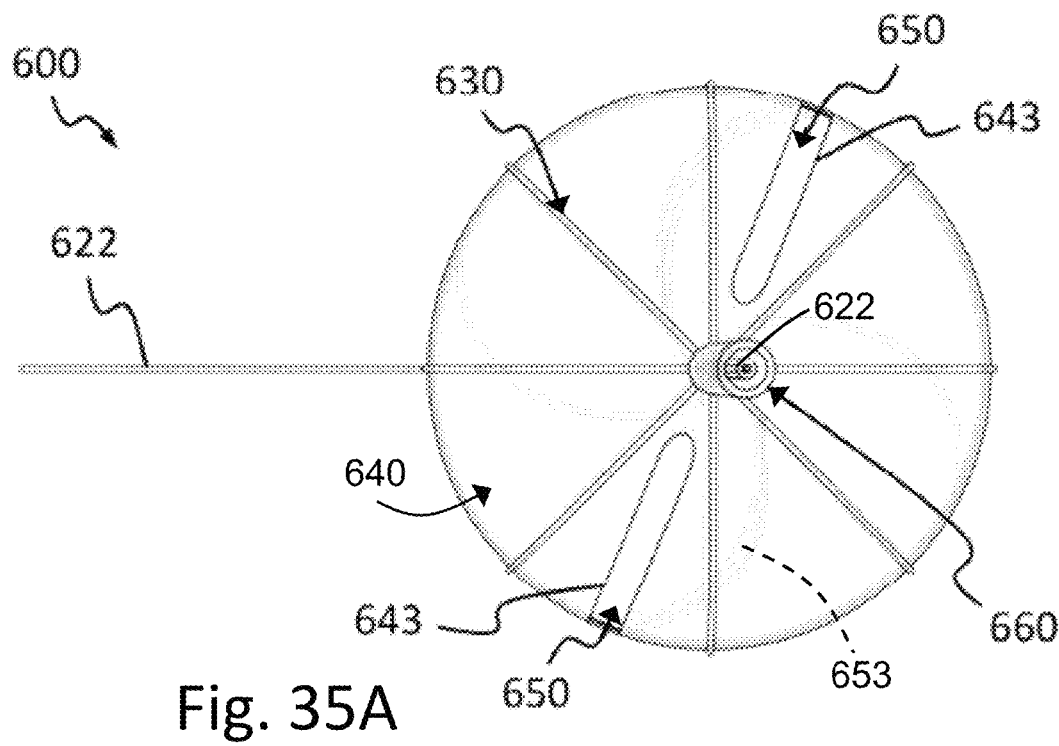
FIG. 35A is a bottom plan view of the endovascular variable aortic control rotating cups device of FIG. 30 in a closed position.
Figure 35B:
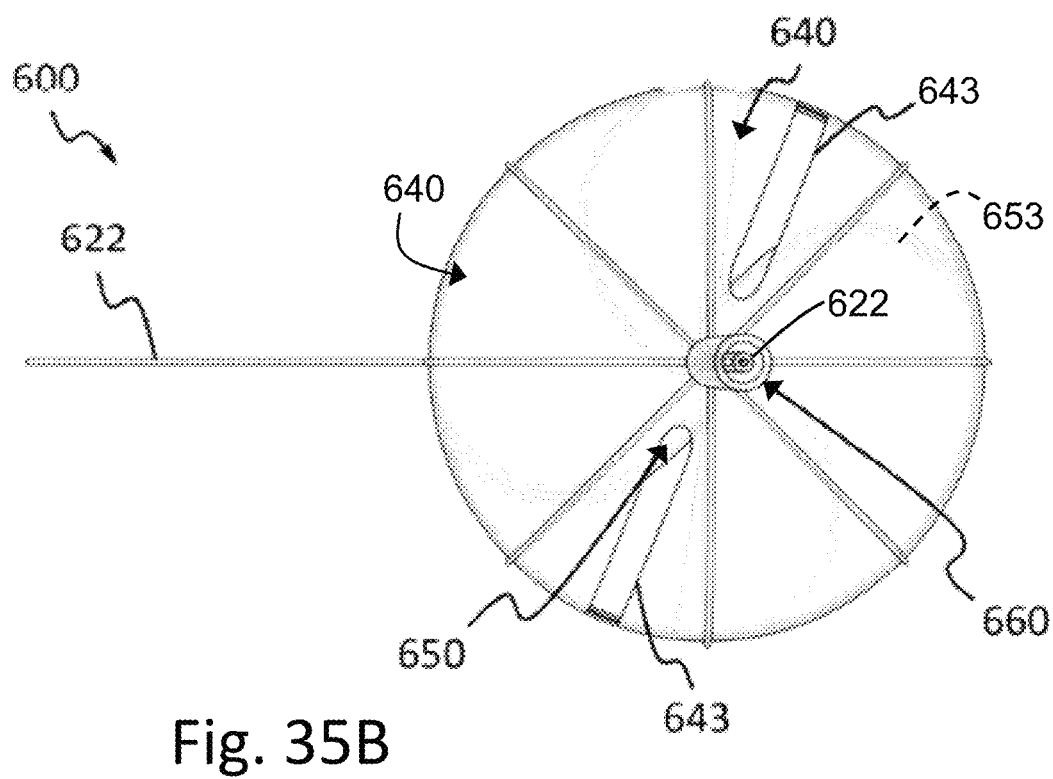
FIG. 35B is a bottom plan view of the endovascular variable aortic control rotating cups device of FIG. 30 in an open position.

Referring now to FIG. 35A and FIG. 35B, a bottom plan view of the EVACC 600 is provided. FIG. 35A shows the EVACC 600 in a fully closed state. The first set of openings 643 of the first membrane 640 are aligned such that flow is blocked by the second membrane 650. FIG. 35B shows the EVACC 600 in a fully open state, where the first set of openings 643 are uncovered from the second membrane 650 such that fluid may pass unrestricted through the EVACC 600.

Deformable Cup Embodiment (EVACC 700): FIGS. 36A-42B

Figure 36A:
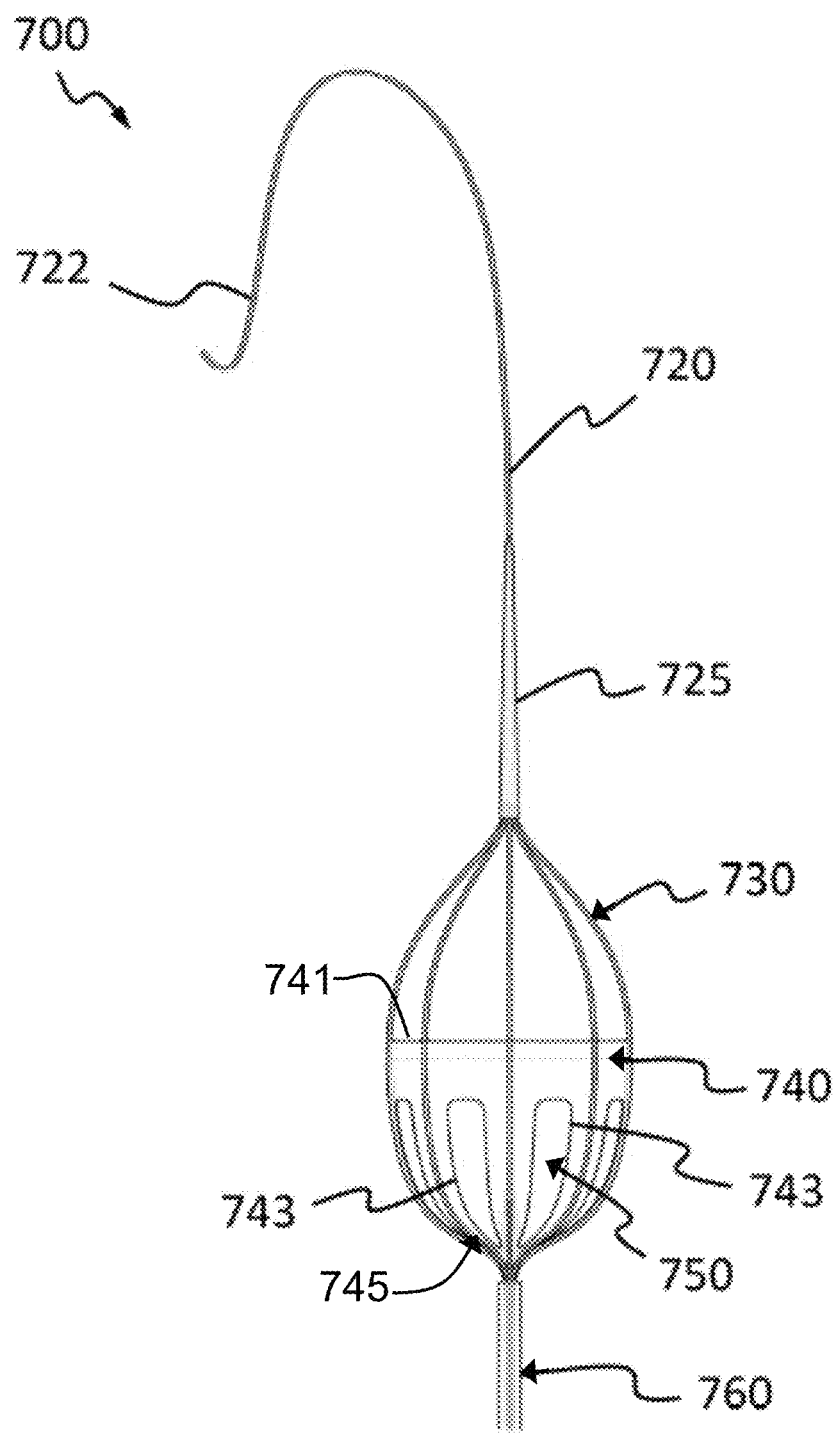
FIG. 36A is an enlarged front elevation view of an endovascular variable aortic control tulip device in a closed position according to an embodiment of the present invention.

Referring now to FIG. 36A, an EVACC 700 according to a seventh alternative embodiment of the invention is shown where anterograde blood flow is controlled or regulated using a deformable mating cups concept. The EVACC 700 comprises two occluding barriers (e.g., cup-shaped membranes) 740, 750 supported by a wire basket 730. The first occluding barrier 740 is positioned downstream of (proximally to) the second occluding barrier 750. The first occluding barrier 740 has multiple interstitial openings 743 around its perimeter. The second occluding barrier 750, which is positioned upstream of the first occluding barrier 740, comprises a flexible membrane that adapts to the shape of the wire basket 730, and thus, the shape of the first occluding barrier 740. In a closed state, the interstitial openings 743 of the first occluding barrier 740 are covered by the second occluding barrier 750 and anterograde blood flow through the EVACC 700 is minimized or stopped.

Figure 36B:
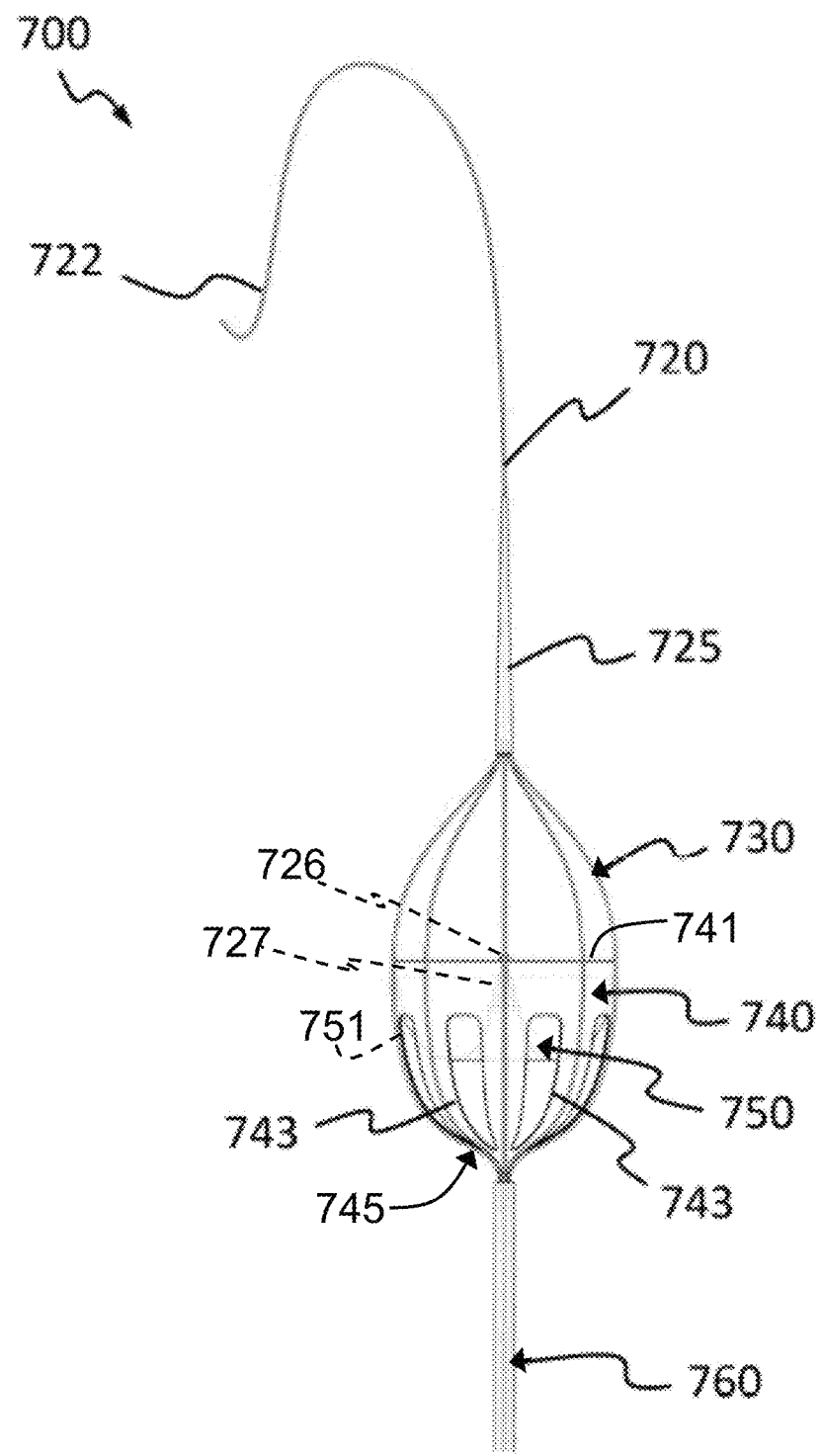
FIG. 36B is an enlarged front elevation view in an open position thereof.

Referring now to FIG. 36B, flow is increased by linear translation of a guide wire 720 to lift a center wire portion 726 of the second occluding barrier 750 off the first occluding barrier 740, causing the interstitial openings 743 of the first occluding barrier 740 to be uncovered. FIG. 36B shows the EVACC 700 in an open state with interstitial openings 743 uncovered. The EVACC 700 includes a central aperture 752 that acts as a choke or restriction on flow. The aperture 752 size may be varied to change the amount of flow. However, the size of the aperture 752 correlates with the size of a bottom center portion of the first occluding barrier 740 such that flow may be effectively stopped when the second occluding barrier 750 is laid flush against the interior of the first occluding barrier 740.

Figure 37:
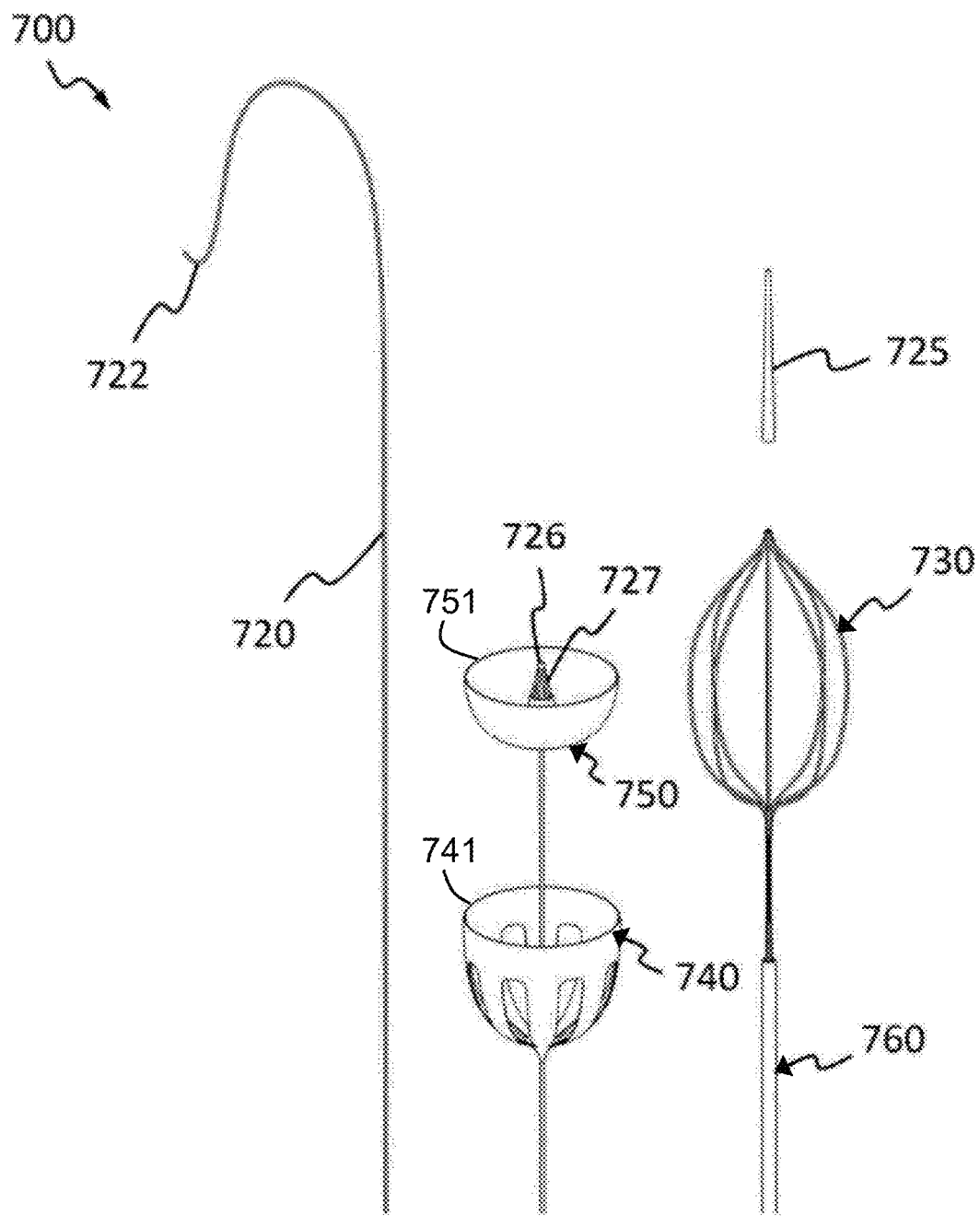
FIG. 37 is an enlarged front elevation view showing components of the device thereof.

Referring now to FIG. 37, a semi-exploded view of components of the EVACC 700 is shown. Central guide wire 720 having J-tip 722 allows the EVACC 700 to be carefully deployed through a patient's vascular to reach a desired occlusion location. Tapered cone 725 is slidably received on the central guide wire 720 and likewise is sized to receive the distal tip 734 of the wire basket 730. The second occluding barrier 750 having a center wire structure 726 and orifice 727 is slidably received on the central guide wire 720. The first occluding barrier 740 is likewise slidably received on the central guide wire 720 to mate with the second occluding barrier 750. Both the first occluding barrier 740 and the second occluding barrier 750 are disposed within the interior of the wire basket 730. The assembly is delivered to a desired location for occlusion via the delivery sheath 760.

Figure 38A:
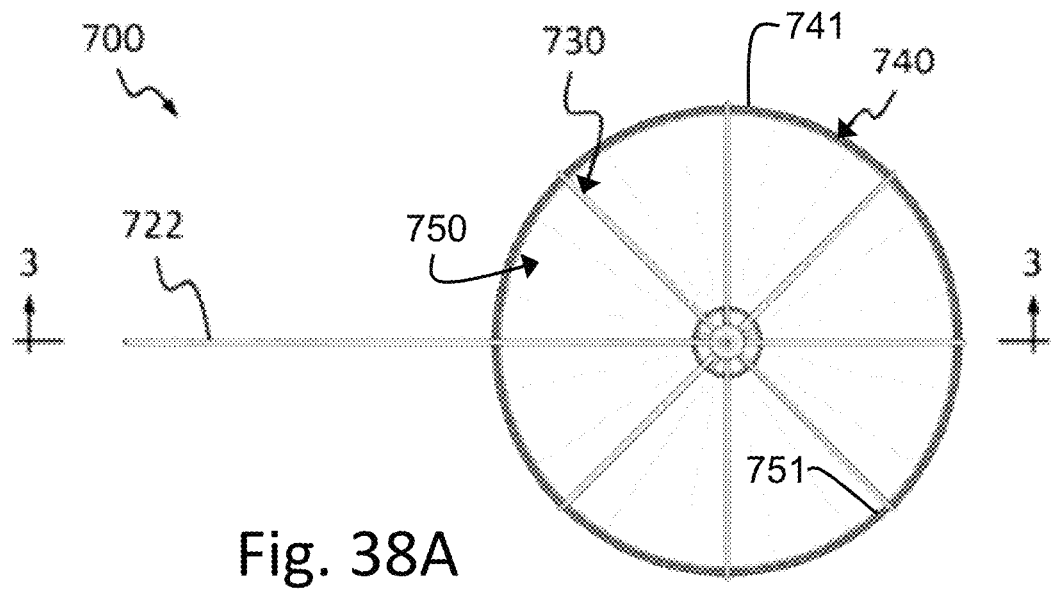
FIG. 38A is a top plan view in a closed position thereof.
Figure 38B:
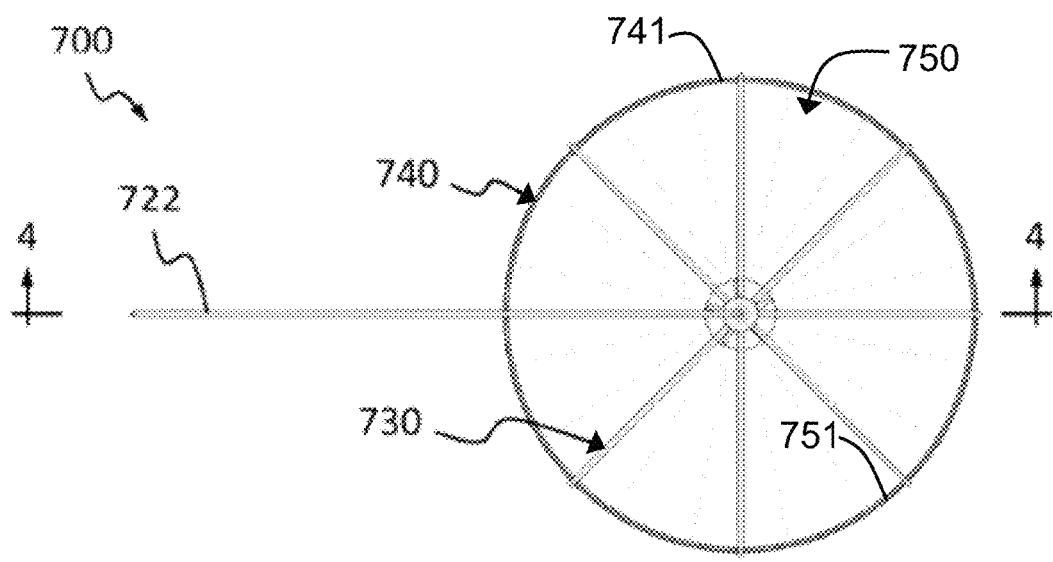
FIG. 38B is a top plan view in an open position thereof.

Referring now to FIG. 38A and FIG. 38B, a top plan view of the EVACC 700 is provided. FIG. 38A shows the EVACC 700 in a closed state, with interstitial openings 743 covered such that flow is restricted. FIG. 38B shows the EVACC 700 in an open state, with the second occluding barrier 750 lifted at its center such that the aperture 752 rises off the first occluding barrier 740. As a result, the interstitial openings 743 are uncovered, allowing blood flow to pass through the aperture 752 and through the interstitial openings 743 to the remainder of the downstream vascular network.

Figure 39A:
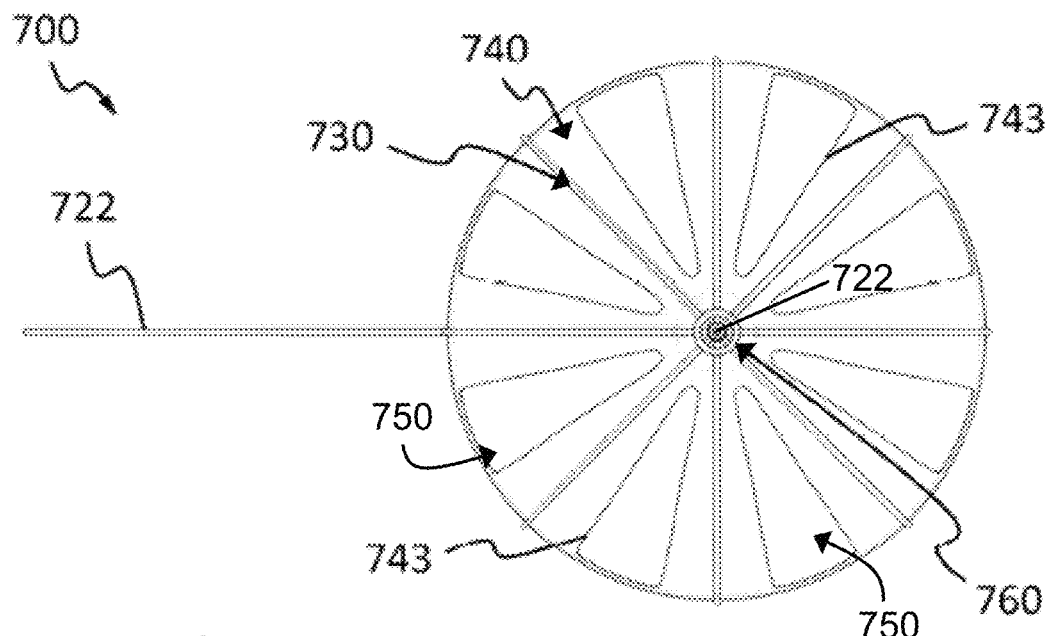
FIG. 39A is a bottom plan in a closed position thereof.
Figure 39B:
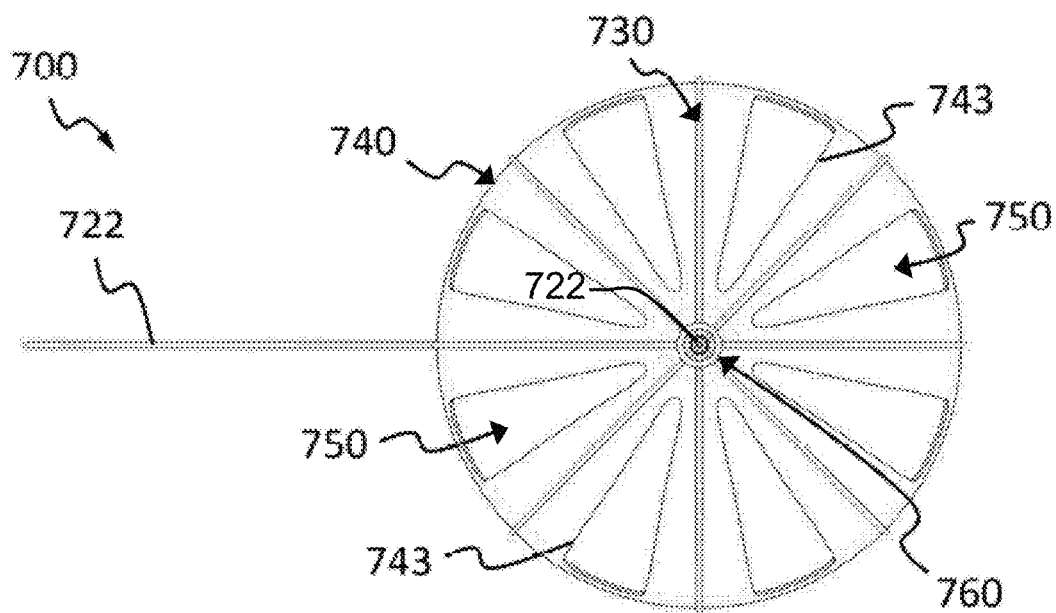
FIG. 39B is a bottom plan view in an open position thereof.

Referring now to FIG. 39A and FIG. 39B, a bottom plan view of the EVACC 700 is provided. FIG. 39A shows the EVACC 700 in a fully closed state. The interstitial openings 743 of the first occluding barrier 740 aligned with the second occluding barrier 740 such that flow is blocked by the second occluding barrier 750. FIG. 39B shows the device 700 in a fully open state, whereby the interstitial openings 743 are uncovered such that blood flow may occur, constrained by the size of the orifice 752.

Figure 40A:
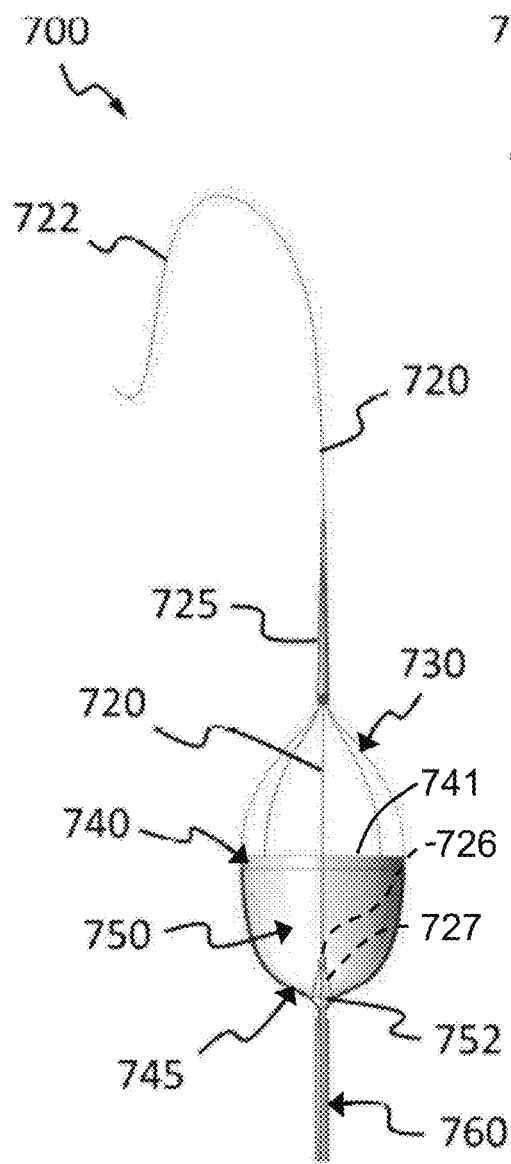
FIG. 40A is a cross-section view of the endovascular variable aortic control tulip device in a closed position shown in FIG. 38A, taken along the cutting plane 3-3.
Figure 40B:
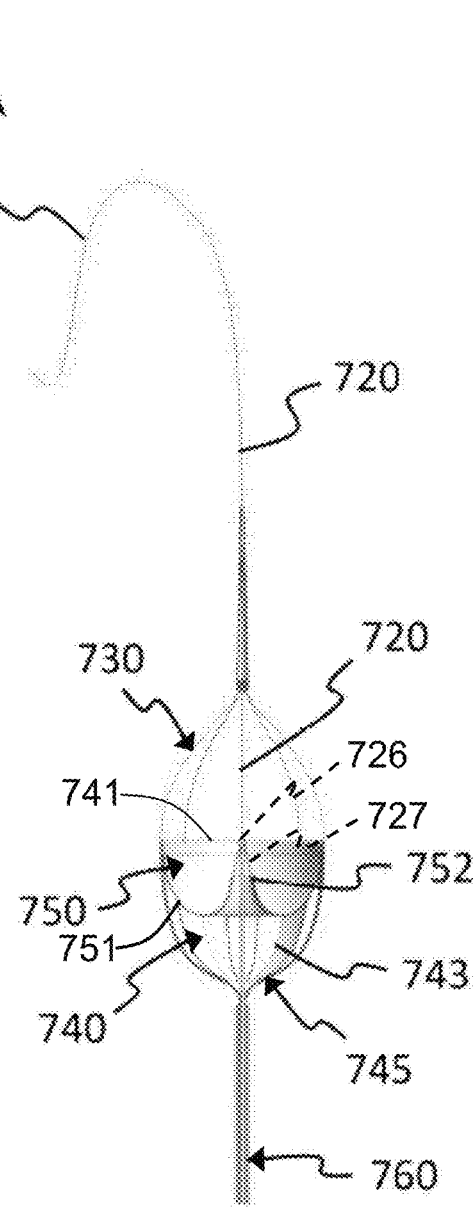
FIG. 40B is a cross-section view of the endovascular variable aortic control tulip device in an open position shown in FIG. 38B, taken along the cutting plane 4-4.

Referring now to FIG. 40A, a cross-sectional view of the EVACC 700 in FIG. 38A taken along section line 3-3 is shown. FIG. 40A shows the EVACC 700 in a fully closed state, in which fluid flow is blocked. Referring now to FIG. 40B, a cross-sectional view of the EVACC 700 in FIG. 38B taken along section line 4-4 is shown. FIG. 40B shows the EVACC 700 in an open state. The wire portion 726 of the second occluding barrier 750 is in a lifted position, causing the interstitial openings 743 between the petals 745 of the first occluding barrier 740 to be uncovered and allowing blood to flow through the aperture 752 and the interstitial openings 743 to the remainder of the vascular.

Figure 41A:
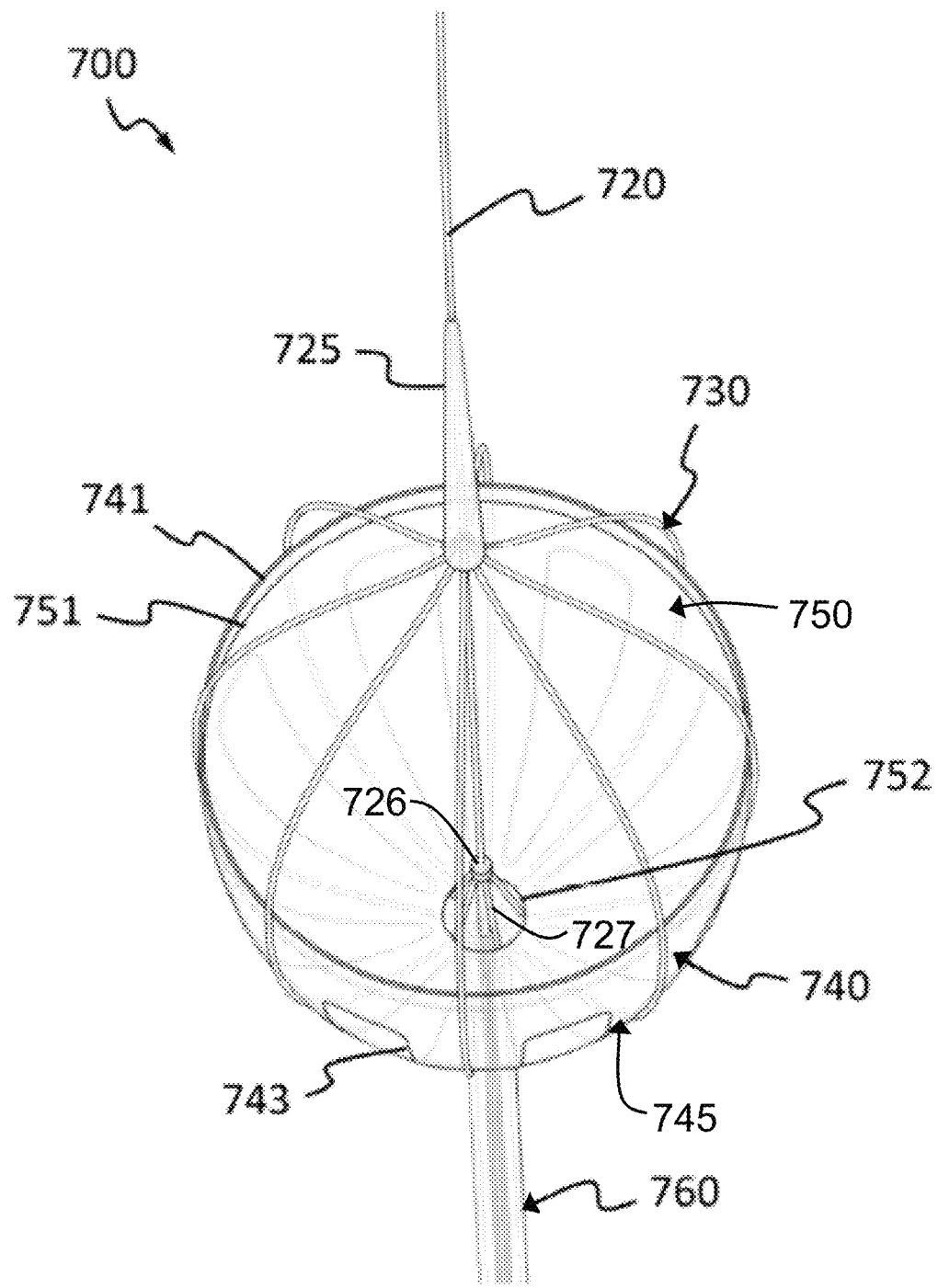
FIG. 41A is an enlarged fragmentary view of an endovascular variable aortic control tulip device in a closed position.
Figure 41B:
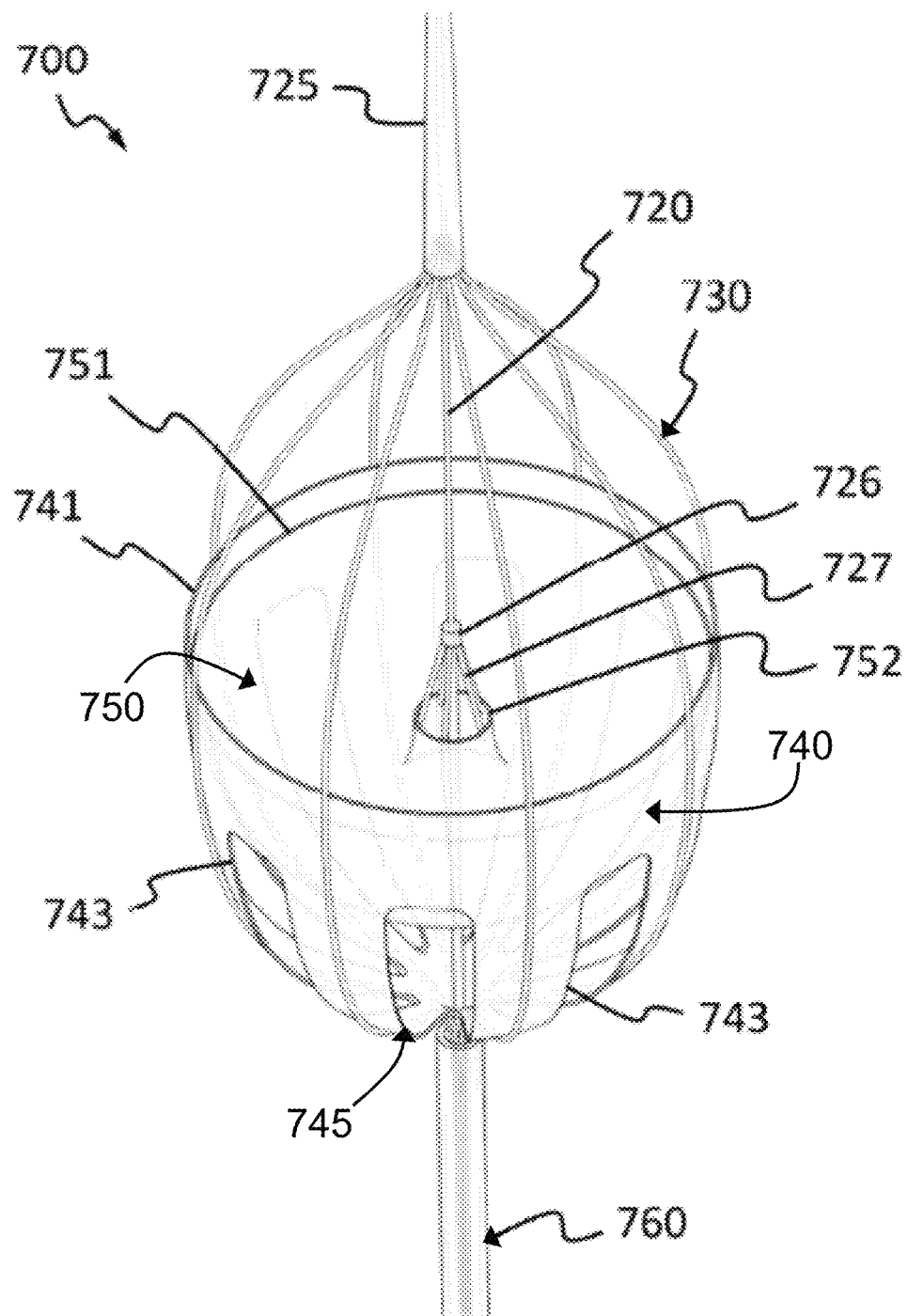
FIG. 41B is a second enlarged fragmentary view in an open position thereof.
Figure 42A:
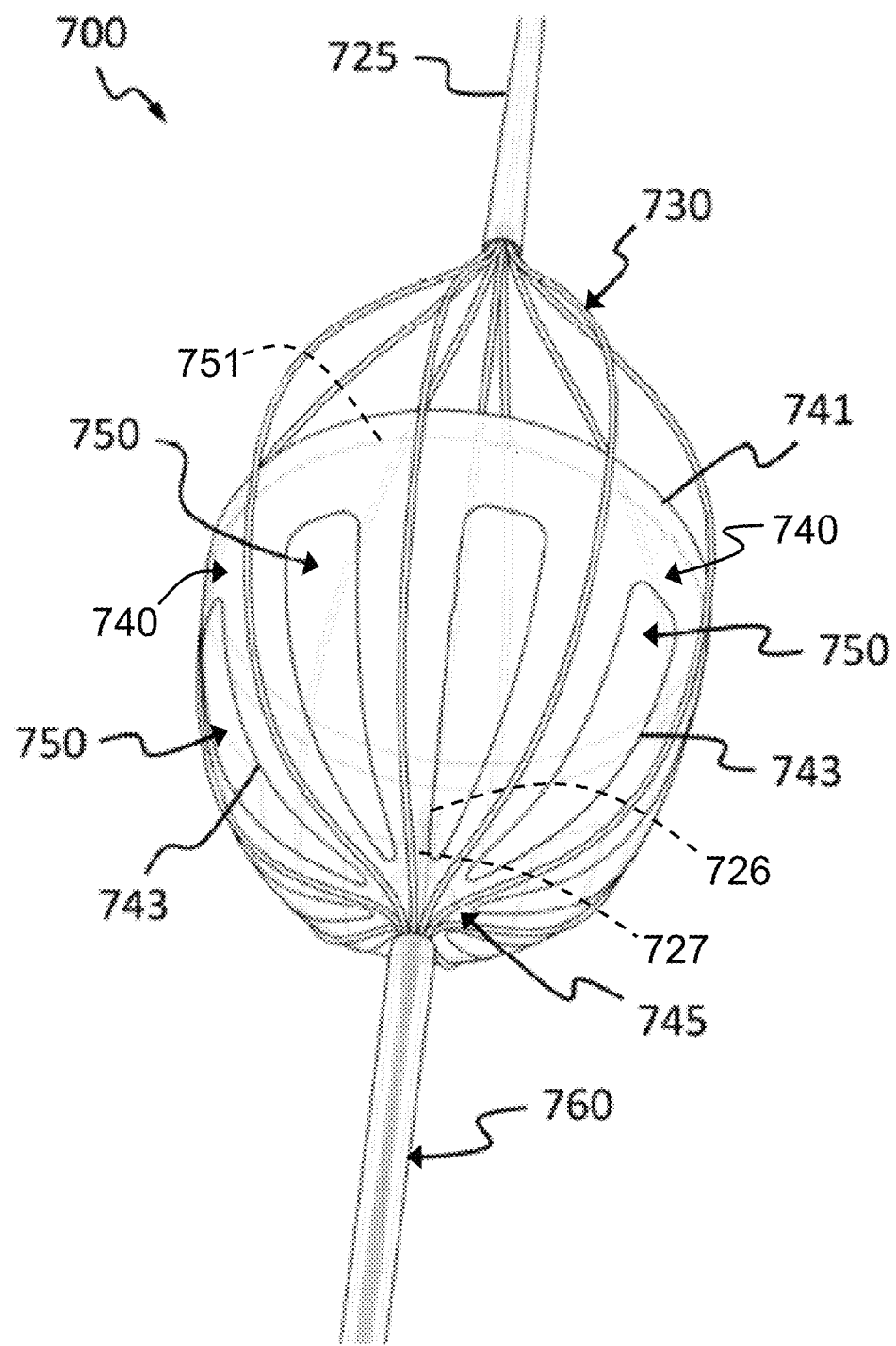
FIG. 42A is a third enlarged fragmentary view in a closed position thereof.
Figure 42B:
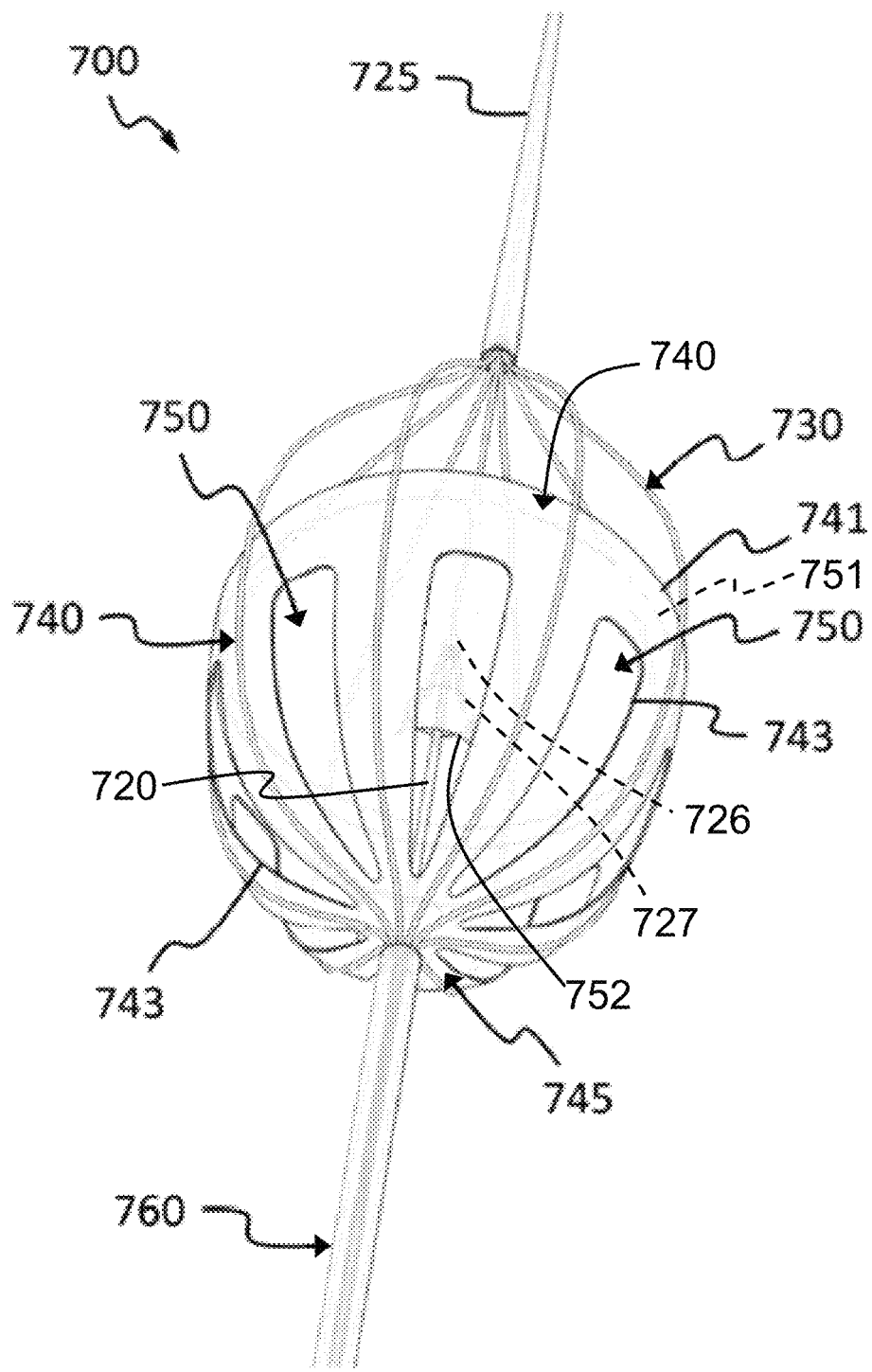
FIG. 42B is a fourth enlarged fragmentary view in an open position thereof.

Referring now to FIG. 41A, an enlarged perspective view of the interior of the EVACC 700 in a fully closed state is shown. FIG. 41B is the same perspective view but with the second occluding barrier 750 raised to allow flow. FIG. 42A and FIG. 42B correspond to FIGS. 41A and 41B, but from the proximal end to distal end perspective view.

Although not specifically shown, applicable to several embodiments described herein, the EVACC may include one or more pressure sensors that communicate blood pressure measurements to an external display, an external control device, or both. The display provides pressure readings to the surgeon to inform the surgeon's operational decisions.

Alternatively, the pressure data may be processed by the external control device, and then used by the control device to determine a desired level of flow restriction. For example, the control device can operate a rotary unit, such as a small stepper motor, to operate the central threaded guide, which may be configured to a) linearly translate the sheath back and forth over perforations in a fenestrated conduit, b) linearly translate a tension wire to constrict or expand a lasso, or c) pressurize or depressurize a captive balloon, for example. Additionally, the EVACC may also incorporate and provide automated control of the degree of flow restriction via an active control algorithm that determines adjustments based on the patient's physiologic status as determined by blood pressure, other relevant metrics, and the assessment of the surgeon. A visual display and associated operational dashboard provides an active touch interface for use by the surgeon or a surgeon's assistant to actively control the operation of the EVACC once deployed. Where an automated control system is provided, the display provides relevant operational parameters and allows automated control to be overridden by the surgeon or assistant. The display may include icons that are selectable by touch, keyboard, mouse, voice, or gesture. The interactive features will allow the surgeon or assistant to quickly select various desired flow and pressure conditions to achieve certain physiologic objectives and set desired operating parameters.

Although driven by a need to address treatment of soldiers injured on the battlefield, the EVACC, in its several embodiments described herein, has applicability that extends beyond military and civilian trauma victims. Any patient with significant risk of hemorrhage will benefit from use of the EVACC to support regulation of distal aortic flow to augment vital perfusion to critical organs. In addition, patients that require increased diversion of blood flow to other portions of their body, such as the brain, can use the device, initially deployed to allow full flow, to gradually restrict downstream flow, and increase flow and pressure to those targeted areas. This approach for augmenting central aortic pressure to perfuse the heart, lungs and brain would extend beyond hemorrhagic shock to include any patient with hypotension and shock that needed augmentation of pressure to keep vital organs alive while other therapeutic measures were undertaken or to support physiology during transport to definitive care.

In addition, although shown and described herein as applicable to use in human subjects, the EVACC is likewise adaptable to use in animal subjects.

The present invention has been particularly shown and described with respect to certain preferred embodiments and features thereof. However, it should be readily apparent to those of ordinary skill in the art that various changes and modifications in form and detail may be made without departing from the spirit and scope of the inventions as set forth herein and the appended claims.

What is claimed is:

1. An endovascular variable aortic occlusion device configured to modulate anterograde blood flow, comprising:
    a longitudinal body having a distal end and a proximal end;
    a first wire basket comprising a memory-shape material, coupled to the distal end of the longitudinal body, and configured to be deployed from a contracted state to an expanded state to engage an inner wall of a patient artery;
    an occlusion barrier comprising a cup-like body configured to surround at least a portion of an exterior surface of the first wire basket with another portion of the exterior surface of the first wire basket not being surrounded by the occlusion barrier, the occlusion barrier being configured to be deployed from a contracted state to an expanded state; and
    at least one adjustable passageway of the occlusion barrier, wherein the at least one adjustable passageway is configured to modulate blood flow through the occlusion barrier.

2. The endovascular variable aortic occlusion device of claim 1, wherein the occlusion barrier includes a proximally-extending conduit coupled to the cup-like body and the at least one adjustable passageway comprises a plurality of orifices in the conduit, the endovascular variable aortic occlusion device further comprising:
    a sheath configured to surround and to move in translational movement with respect to the conduit of the occlusion barrier such that movement of the sheath modulates the blood flow through the plurality of orifices of the occlusion barrier.

3. The endovascular variable aortic occlusion device of claim 1, wherein the cup-like body of the occlusion barrier includes a proximal terminal end and the at least one adjustable passageway is an orifice in the proximal terminal, a diameter of the orifice configured to contract or dilate with the contracted state and the expanded state of the occlusion barrier, respectively.

4. The endovascular variable aortic occlusion device of claim 3, further comprising:
    a sheath configured to surround and to move with respect to in the first wire basket and the occlusion barrier such that movement of the sheath contracts or dilates the diameter of the orifice.

5. The endovascular variable aortic occlusion device of claim 3, further comprising:
    a lasso wire comprising first and second wire portions, each having a distal end and a proximal end, and first and second wire segments on the distal ends of the respective first and second wire portions, wherein the first and second wire segments, together, form a semicircle configured to receive the first wire basket therethrough; and
    an overlapping portion extending from the proximal terminal end of the occlusion barrier, the overlapping portion configured to conform to the first and second wire segments to form the orifice of the occlusion barrier,
    wherein movement of the first wire portion with respect to the second wire portion is configured to change the diameter of the orifice.

6. The endovascular variable aortic occlusion device of claim 3, further comprising:
    a wire mesh having a contracted state and an expanded state, the wire mesh configured to extend through the orifice, wherein moving the wire mesh from the contracted state to the expanded state adjusts the diameter of the orifice.

7. The endovascular variable aortic occlusion device of claim 3, further comprising:
    a conduit portion coupled to the proximal terminal end of the occlusion barrier, the conduit portion comprising an elastomeric wall; and
    a wire mesh having first and second states, the first state having a first diameter and first length and the second state having a second diameter that is smaller than the first diameter and a second length that is greater than the first length, the wire mesh configured to extend through the conduit portion, wherein actuating the wire mesh from the first state to the second state reduces the diameter of the orifice.

8. The endovascular variable aortic occlusion device of claim 1, wherein the memory-shape material is a metal alloy, a polymer, or a combination thereof.

* * * * *